United States Patent
Schindler et al.

(10) Patent No.: US 9,981,950 B2
(45) Date of Patent: May 29, 2018

(54) TRIAZOLES AS NR2B RECEPTOR INHIBITORS

(71) Applicant: Janssen Pharmaceuticals, Inc., Titusville, NJ (US)

(72) Inventors: Rudolf Schindler, Dresden (DE); Hans-Joachim Lankau, Weinböhla (DE); Norbert Höfgen, Ottendorf-Okrilla (DE); Ute Egerland, Radebeul (DE); Barbara Langen, Radebeul (DE); Rita Dost, Dresden (DE); Simon Ward, Lewes Sussex (GB)

(73) Assignee: JANSSEN PHARMACEUTICALS, INC., Titusville, NJ (US)

( * ) Notice: Subject to any disclaimer, the term of this patent is extended or adjusted under 35 U.S.C. 154(b) by 0 days. days.

(21) Appl. No.: 15/503,864

(22) PCT Filed: Aug. 14, 2015

(86) PCT No.: PCT/US2015/045412
§ 371 (c)(1),
(2) Date: Feb. 14, 2017

(87) PCT Pub. No.: WO2016/025917
PCT Pub. Date: Feb. 18, 2016

(65) Prior Publication Data
US 2017/0226087 A1    Aug. 10, 2017

Related U.S. Application Data

(60) Provisional application No. 62/146,656, filed on Apr. 13, 2015, provisional application No. 62/037,831, filed on Aug. 15, 2014.

(51) Int. Cl.
C07D 249/08    (2006.01)
C07D 403/06    (2006.01)

(52) U.S. Cl.
CPC ......... C07D 403/06 (2013.01); C07D 249/08 (2013.01)

(58) Field of Classification Search
None
See application file for complete search history.

(56) References Cited

U.S. PATENT DOCUMENTS

| | | |
|---|---|---|
| 2007/0275965 A1 | 11/2007 | Thomas et al. |
| 2008/0300239 A1 | 12/2008 | Adams et al. |
| 2014/0275011 A1 | 9/2014 | Mastracchio et al. |

FOREIGN PATENT DOCUMENTS

| | | |
|---|---|---|
| EP | 2194045 | 6/2010 |
| WO | 2003082868 A1 | 10/2003 |
| WO | WO 2005/080379 | 9/2005 |
| WO | WO 2008/145616 | 12/2008 |
| WO | 2009058261 A1 | 5/2009 |
| WO | WO 2009/118187 A1 | 10/2009 |
| WO | 2010043396 A1 | 4/2010 |
| WO | WO 2013/130855 | 9/2013 |
| WO | 2014124651 A1 | 8/2014 |
| WO | WO 2016/025917 | 2/2016 |

OTHER PUBLICATIONS

International Search Report and Written Opinion dated Nov. 10, 2015, for Corresponding International Application PCT/US2015/045412.
Addy, et al., Single-Dc3e Administration of MK-0657, an N112B-Selective NMDA Antagonist, Does Not Result in Clinically Meaningful Improvement in Motor Functions in Patients 127ith Moderate ll'arkinson'Disease, Journal of Clinical Pharmacology, 2009, pp. 856-864, vol. 49.
Berge, et al., Pharmaceutical Salts, Journal of Pharmaceutical Sciences, Jan. 1, 1977, pp. 1-19—XP000562636, vol. 166 No. 1, WO.
Buonarati, et al., Role of sulfation and acetylation in the activation of 2-hydroxyamino-1-methyl-6-phenylimidazo [4,5-b]pyridine to intermediates which bind DNA, Mutation Research, Jun. 21, 1990, pp. 185-190, vol. 245.
Lima-Ojeda, et al., Pharmacological blockade of GluN2B—containing NMDA receptors induces antidepressant-like effects lacking psychotomimetic action and neurotoxicity in the perinatal and adult rodent brain, Progress in Neuro-Psychopharmacology & Biological Psychiatry, Apr. 30, 2013, pp. 28-33, vol. 45.
Nutt, et al., Effects of a NR2B Selective NMDA Glutamate Antagonist, CP-101,606, on Dyskinesia and Parkinsonism, Movement Disorders, Aug. 29, 2008, pp. 1860-1866, vol. 23 Issue 13.
Zarate, et al., A Randomized Trail of an N-methyl_D-aspartate Antagonist in Treatment-Resistant Major Depression, Arch Gen Psychiatry, 2006, pp. 856-864, vol. 63.
U.S. Appl. No. 15/503,875.
U.S. Appl. No. 15/205,632.
U.S. Appl. No. 15/428,710.
U.S. Appl. No. 62/404,798.
PCT ISR PCT/US2017/017093, dated Mar. 20, 2017.
PCT ISR PCT/US2015/045413, dated Nov. 27, 2015.
PRC ISR PCT/US2016/41339, dated Sep. 27, 2016.
Andreas Straube., Pharmacology of vertigo/nystagmus/oscillopsia, Current Opinion in Neurology, 2005, pp. 11-14, vol. 18 Issue 1.
Arnold, et al., Glutamate receptor gene (GRIN2B) associated with reduced anterior cingulate glutamatergic concentration in pediatric obsessive-compulsive disorder, Psychiatry Research: Neuroimaging, Feb. 19, 2009, pp. 136-139, vol. 172 issue 2.

(Continued)

Primary Examiner — Alicia L Otton

(57) ABSTRACT

Provided here in are compounds of Formula I having the structure: Also provided herein are compositions comprising compounds of Formula I and methods of using compounds of Formula I for the treatment of disorders, diseases or conditions mediated by GluN2B receptors.

(1)

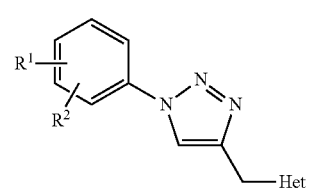

28 Claims, No Drawings

(56) References Cited

OTHER PUBLICATIONS

Berberich, et al., The role of NMDAR subtypes and charge transfer during hippocampal LTP induction, Neuropharmacology, 2007, pp. 77-86, vol. 52 Issue 1.
Berge, et al, Pharmaceutical Salts, Journal of Pharmaceutical Sciences, 1977, pp. 1-19, vol. 66 Issue 1.
Bertolini, et al., A New Rational Hypothesis for the Pharmacophore of the Active Metabolite of Leflunomide, a Potent Immunosuppressive Drug, Journal of Medicinal Chemistry, Jan. 17, 1997, pp. 2011-2016, vol. 40 Issue 13.
Bullock, et al., An Open-Label Study of CP-101,606 in Subjects with a Severe Traumatic Head Injury or Spontaneous Intracerebral Hemorrhage, Annals New York Academy of Sciences, 1999, pp. 51-58, vol. 890.
Chattopadhyay, et al., Fused Tetrazoles as Azide Surrogates in Click Reaction: Efficient Synthesis of N-Heterocycle-Substituted 1,2,3-Triazoles, Organic Letters, Mar. 30, 2010, pp. 2166-2169, vol. 12 Issue 9.
Cull-Candy, et al., NMDA receptor subunits: diversity, development and disease, Current Opinion in Neurobiology, 2001, pp. 327-335, vol. 11 Issue 3.
Dalmau, et al., Anti-NMDA-receptor encephalitis: case series and analysis of the eff ects of antibodies, Lancet Neurol, Dec. 2008, pp. 1091-1098, vol. 7 Issue 12.
Dorval, et al., Association of the glutamate receptor subunit gene GRIN2B with attention-deficit/hyperactivity disorder, Genes, Brain and Behavior, 2007, pp. 444-452, vol. 6 Issue 5.
Farjam, et al., Inhibition of NR2B-Containing N-methyl-D-Aspartate Receptors (NMDARs) in Experimental Autoimmune Encephalomyelitis, a Model of Multiple Sclerosis, Iranian Journal of Pharmaceutical Research, 2014, pp. 695-705, vol. 13 Issue 2.
Fleisher, et al., Improved oral drug delivery: solubility limitations overcome by the use of prodrugs, Advanced Drug Delivery Reviews, 1996, pp. 115-130, vol. 19.
Fuller, et al., Differential expression of the NMDA NR2B receptor subunit in motoneuron populations susceptible and resistant to amyotrophic lateral sclerosis, Neuroscience Letters, Jan. 26, 2006, pp. 157-161, vol. 399 Issue (1-2).
Glenn D. Considine., Van Nostrand's Encyclopedia of Chemistry,, Encyclopedia of Chemistry, 2005, pp. 261, Chapter 5.
Grasselli, et al., Abnormal NMDA receptor function exacerbates experimental autoimmune encephalomyelitis, British Journal of Pharmacology, 2013, pp. 502-517, vol. 168 Issue 2.
Grimwood, et al., NR2B—containing NMDA receptors are upregulated in temporal cortex in schizophrenia, NeuroReport, Feb. 25, 1999, pp. 461-465, vol. 10 Issue 3.
Guitton, et al., Blockade of Cochlear NMDA Receptors Prevents Long-Term Tinnitus during a Brief Consolidation Window after Acoustic Trauma, Neural Plasticity, Dec. 12, 2007, pp. 1-11, Article ID 80904.
Haller, et al., NR2B subunit-specific NMDA antagonist Ro25-6981 inhibits the expression of conditioned fear: a comparison with the NMDA antagonist MK-801 and fluoxetine, Behavioural Pharmacology, 2011, pp. 113-121, vol. 22 Issue 2.
Hanson, et al., Altered GluN2B NMDA receptor function and synaptic plasticity during early pathology in the PS2APP mouse model of Alzheimer's disease, Neurobiology of Disease, 2015, pp. 254-262, vol. 74.
Hu, et al., Expression of immediate-early genes in the dorsal cochlear nucleus in salicylate-induced tinnitus, Eur Arch Otorhinolaryngol, 2016, pp. 325-332, vol. 273 Issue 2.
Jozsef Nagy., The NR2B Subtype of NMDA Receptor: A Potential Target for the Treatment of Alcohol Dependence, Current Drug Targets—CNS & Neurological Disorders, 2004, pp. 169-179, vol. 3 Issue 3.
Jun Wu, et al., Targeting the NMDA Receptor Subunit NR2B for the Treatment of Neuropathic Pain, Neurotherapeutics:, 2009, pp. 693-702, vol. 6 Issue 4.
Kenneth D.Bagshawe., Antibody-Directed Enzyme prodrug Therapy : A Review, Drug Development Research, 1995, pp. 220-230, vol. 34.
Kolb, et al., Click Chemistry: Diverse Chemical Function from a Few Good Reactions, Angew. Chem. Int. Ed, 2001, pp. 2004-2021, vol. 40.
Kowal, et al., Human lupus autoantibodies against NMDA receptors mediate cognitive impairment, PNAS, Dec. 26, 2006, pp. 19854-19859, vol. 103 Issue 52.
Leaderbrand, et al., Co-activation of NR2A and NR2B subunits induces resistance to fear extinction, Neurobiol Learn Mem, 2014, pp. 35-40, vol. 113.
Leaver, et al., Neuroprotective Effects of a Selective N-Methyl-d-Aspartate NR2B Receptor Antagonist in the 6-Hydroxydopamine Rat Model of Parkinson's Disease, Clinical and Experimental Pharmacology and Physiology, May 27, 2008, pp. 1388-1394, vol. 35 Issue 11.
Leyva, et al., Photochemistry of Fluorinated Aryl Azides in Toluene Solution and in Frozen Polycrystals, J. Org. Chem, May 8, 1989, pp. 5938-5945, vol. 54 Issue 25, American Chemical Society.
Li, et al., Enhanced Striatal NR2B—Containing N-Methyl-D-Aspartate Receptor-Mediated Synaptic Currents in a Mouse Model of Huntington Disease, J Neurophysiol, Jun. 3, 2004, pp. 2738-2746, vol. 92 Issue 5.
Li, et al., Glutamate N-methyl-D-aspartate Receptor Antagonists Rapidly Reverse Behavioral and Synaptic Deficits Caused by Chronic Stress Exposure, Biol Psychiatry, 2011, pp. 754-761, vol. 69 Issue 8.
Li, et al., Soluble Ab Oligomers Inhibit Long-Term Potentiation through a Mechanism Involving Excessive Activation of Extrasynaptic NR2B—Containing NMDA Receptors, The Journal of Neuroscience, May 4, 2011, pp. 6627-6638, vol. 31 Issue 18.
Martucci, et al., N-methyl-d-aspartate receptor NR2B subunit gene GRIN2B in schizophrenia and bipolar disorder: Polymorphisms and mRNA levels, Schizophrenia Research, Mar 20, 2006, pp. 214-221, vol. 84 Issue (2-3).
Massey, et al., Differential Roles of NR2A and NR2B—Containing NMDA Receptors in Cortical Long-Term Potentiation and Long-Term Depression, The Journal of Neuroscience, Sep. 8, 2004, pp. 7821-7828, vol. 24 Issue 36.
Miller, et al., GluN2B—containing NMDA receptors regulate depression-like behavior and are critical for the rapid antidepressant actions of ketamine, eLife, Oct. 23, 2014, pp. 1-22, vol. 3.
Morissette, et al., Prevention of Levodopa-Induced Dyskinesias by a Selective NR1A/2B N-Methyl-D-aspartate Receptor Antagonist in Parkinsonian Monkeys: Implication of Preproenkephalin, Movement Disorders, 2006, pp. 9-17, vol. 21 Issue 1.
Naskar, et al., Saving the Nerve from Glaucoma: Memantine to Caspaces, Seminars in Ophthalmology, Sep. 1999, pp. 152-158, vol. 14 Issue 3.
Naspolini, et al., Traxoprodil decreases pentylenetetrazol-induced seizures, Epilepsy Research, Jan. 24, 2012, pp 12-19, vol. 100 Issue (1-2).
Nicholas Bodor., Novel Approaches to the Design of Safer Drugs: Soft Drugs and Site-Specific Chemical Delivery Systems, Advances in Drug Research, 1984, pp. 256-331, vol. 13.
Orgogozo, et al., Efficacy and Safety of Memantine in Patients With Mild to Moderate Vascular Dementia A Randomized, Placebo-Controlled Trial (MMM 300), Stroke, 2002, pp. 1834-1839, vol. 33.
Paoletti, et al., NMDA receptor subunit diversity: impact on receptor properties, synaptic plasticity and disease, Nature Reviews | Neuroscience, Jun. 2013, pp. 383-400, vol. 14 Issue 6.
Paulekuhn, et al., Trends in Active Pharmaceutical Ingredient Salt Selection based on Analysis of the Orange Book Database, Journal of Medicinal Chemistry, Aug. 20, 2007, pp. 6665-6672, vol. 50 Issue 26.
Peeters, et al., Effects of Pan- and Subtype-Selective N-Methyl-D-aspartate Receptor Antagonists on Cortical Spreading Depression in the Rat: Therapeutic Potential for Migraine, The Journal of Pharmacology and Experimental Therapeutics, Jan. 24, 2007, pp. 564-572, vol. 321 Issue 2.
Porsolt etal., Behavioural Despair in Mice: A Primary Screening Test for Antidepressants, Arch int Pharmacodyn, 1977, pp. 327-336, vol. 229.

(56) References Cited

OTHER PUBLICATIONS

Preskorn, et al., An Innovative Design to Establish Proof of Concept of the Antidepressant Effects of the NR2B Subunit Selective N-Methyl-D-Aspartate Antagonist, CP-101,606, in Patients Wth Treatment-Refractory Major Depressive Disorder, Journal of Clinical Psychopharmacology, Dec. 2008, pp. 631-637, vol. 28 Issue 6.
Remington., Remington Pharmaceutical Sciences., Pharmaceutical Sciences., 1985, pp. 1418, vol. 76.
Robinson, et al., Discovery of the Hemifumarate and (r-L-Alanyloxy)methyl Ether as Prodrugs of an Antirheumatic Oxindole: Prodrugs for the Enolic OH Group, Journal of Medicinal Chemistry, 1996, pp. 10-18, vol. 39 Issue 1.
Shan, et al., Prodrug Strategies Based on Intramolecular Cyclization Reactions, Journal of Pharmaceutical Sciences, Jul. 1997, pp. 765-767, vol. 86 Issue 7.
Shen, et al., Heroin relapse requires long-term potentiation-like plasticity mediated by NMDA2b-containing receptors, PNAS, Nov. 29, 2011, pp. 19407-19412, vol. 108 Issue 48.
Starck, et al., Drug therapy for acquired pendular nystagmus in multiple sclerosis, J Neurol, 1997, pp. 9-16, vol. 244 Issue 1.
Steece-Collier, et al., Antiparkinsonian Actions of CP-101,606, an Antagonist of NR2B Subunit-Containing N-Methyl-D-Aspartate Receptors, Experimental Neurology, Feb. 4, 2000, pp. 239-243, vol. 163 Issue 1.
Susan Duty., Targeting Glutamate Receptors to Tackle the Pathogenesis, Clinical Symptoms and Levodopa-Induced Dyskinesia Associated with Parkinson's Disease, CNS Drugs, Oct. 31, 2012, pp. 1017-1032, vol. 26 Issue 12.
Tang, et al., Disturbed Ca2+ signaling and apoptosis of medium spiny neurons in Huntington's disease, PNAS, Feb. 15, 2005, pp. 2602-2607, vol. 102 Issue 7.
Tang, et al., Genetic enchancement of learning and memory in mice, Nature, Sep. 2, 1999, pp. 63-69, vol. 401 Issue 6748.
Traynelis, et al., Glutamate Receptor Ion Channels: Structure, Regulation, and Function, Pharmacol Rev, 2010, pp. 405-496, vol. 62 Issue 3.
Wang, et al., Targeting the NMDA receptor subunit NR2B for treating or preventing age-related memory decline, Expert Opin. Ther. Targets, 2014, pp. 1121-1130, vol. 18 Issue 10.
Watanabe, et al., Distinct Distributions of Five N-Methyl-D-Aspartate Receptor Channel Subunit mRNAs in the Forebrain, The Journal of Comparative Neurology, Jul. 30, 1993, pp. 377-390, vol. 338 Issue 3.
Weickert, et al., Molecular evidence of N-methyl-D-aspartate receptor hypofunction in schizophrenia, Molecular Psychiatry, 2013, pp. 1185-1192, vol. 18.
Won, et al., Autistic-like social behaviour in Shank2-mutant mice improved by restoringNMDA receptor function, Nature, Jun. 14, 2012, pp. 261-265, vol. 486.
Yang, et al., Reduced brain infarct volume and improved neurological outcome by inhibition of the NR2B subunit of NMDA receptors by using CP101,606-27 alone and in combination with rt-PA in a thromboembolic stroke model in rats, J. Neurosurg, Feb. 2003, pp. 397-403, vol. 98 Issue 2.
Yuan, et al., Context-Dependent GluN2B-Selective Inhibitors of NMDA Receptor Function Are Neuroprotective with Minimal Side Effects, Neuron, Mar. 18, 2015, pp. 1305-1318, vol. 85 Issue 6.
STN Registry database entry for CAS RN 1394745-67-5, Entered STN Sep. 18, 2012, Accessed Sep. 8, 2017.
Ito, et al., "A Medium-term Rat Liver Bioassay for Rapid in Vivo Detection of Carcinogenic Potential of Chemicals" Cancer Science, vol. 94(1), pp. 3-8, 2003.

TRIAZOLES AS NR2B RECEPTOR INHIBITORS

CROSS REFERENCE TO RELATED APPLICATIONS

This application is a national phase of International Application No. PCT/US2015/045412 filed on Aug. 14, 2015, which claims the benefit of U.S. Provisional Application No. 62/146,656, which was filed on Apr. 13, 2015; and U.S. Provisional Application No. 62/037,831, which was filed on Aug. 15, 2014, each of which is incorporated herein by reference in its entirety.

TECHNICAL FIELD

The invention relates to 1,2,3-triazole derivatives and the use of these compounds for the treatment of various diseases and conditions.

BACKGROUND OF THE INVENTION

Glutamate is one of the major excitatory neurotransmitters that is widely spread in the brain. First indication of its role as an excitatory messenger was in the 1950's when it was observed that intravenous administration of glutamate induces convulsions. However, the detection of the whole glutamatergic neurotransmitter system with its various receptors did not take place before the 1970's and 1980's when numerous antagonists were developed or, as in the case of PCP and ketamine, were identified as antagonists. Finally, in the 1990's molecular biology provided the tools for the classification of the glutamatergic receptors.

Glutamate is a main excitatory neurotransmitter in the mammalian central nervous system and N-methyl-D-aspartate (NMDA) receptors are a subtype of ionotropic glutamate receptors that mediate excitatory synaptic transmission in the brain. NMDA receptors are ubiquitously distributed throughout the brain and play a key role in synaptic plasticity, synaptogenesis, excitotoxicity, memory acquisition and learning. NMDA receptors are distinct from other major subtypes of ionotropic glutamate receptors (AMPA and kainate receptors) in that they are blocked by $Mg^{2+}$ at resting membrane potentials, are highly $Ca^{2+}$ permeable, and require co-activation by two distinct neurotransmitters: glutamate and glycine (or D-serine) (Traynelis S F et al., Pharmacol Rev. 2010; 62(3):405-96). The influx of $Ca^{2+}$ through NMDA receptors triggers signaling cascades and regulates gene expression that is critical for different forms of synaptic plasticity including both long-term potentiation of synapse efficacy (LTP) (Berberich S et al., Neuropharmacology 2007; 52(1):77-86) and long-term depression (LTD) (Massey, P V et al., J Neurosci. 2004 8; 24(36):7821-8).

The vast majority of the mammalian NMDA receptors form a heterotetramer made of two obligatory GluN1 units and two variable GluN2 receptor subunits encoded by the GRIN1 gene and one of four GRIN2 genes, respectively. One or both GluN2 subunits can be potentially replaced by a GluN3A or a GluN3B subunit. The GRIN1 gene product has 8 splice variants while there are 4 different GRIN2 genes (GRIN2A-D) encoding four distinct GluN2 subunits. The glycine binding site is present on the GluN1 subunit and the glutamate binding site is present on the GluN2 subunit.

The GluNR2 subunits play a dominant role in determining the functional and pharmacological properties of the NMDA receptor assembly and exhibit distinct distribution in different areas of the brain. For instance, GluN2B subunits are expressed primarily in the forebrain in the adult mammalian brain (Paoletti P et al., Nat Rev Neurosci. 2013; 14(6):383-400; Watanabe M et al., J Comp Neurol. 1993; 338(3):377-90) and are implicated in learning, memory processing, mood, attention, emotion and pain perception (Cull-Candy S et al., Curr Opin Neurobiol. 2001; 11(3):327-35).

Compounds that modulate GluN2B-containing NMDA receptor function can be useful in treatment of many neurological and psychiatric disorders including but not limited to bipolar disorder, major depressive disorder (Miller O H et al., eLife. 2014; 3:e03581; Li N et al., Biol Psychiatry. 2011; 69(8):754-61), treatment-resistant depression (Preskorn S H et al. J Clin Psychopharmacol. 2008; 28(6):631-7) and other mood disorders (e.g., postpartum depression, seasonal affective disorder and the like), Alzheimer's disease (Hanson J E et al., Neurobiol Dis. 2015; 74:254-62; Li S et al., J Neurosci. 2011; 31(18):6627-38), Parkinson's disease (Duty S, CNS Drugs. 2012; 26(12):1017-32; Steece-Collier K et al., Exp Neurol. 2000; 163(1):239-43; Leaver K R et al. Clin Exp Pharmacol Physiol. 2008; 35(11): 1388-94), Huntington's chorea (Tang T S et al., Proc Natl Acad Sci USA. 2005; 102(7):2602-7; Li L et al., J Neurophysiol. 2004; 92(5): 2738-46), multiple sclerosis (Grasselli G et al., Br J Pharmacol. 2013; 168(2):502-17; Farjam M et al., Iran J Pharm Res. 2014; 13(2):695-705), cognitive impairment (Wang D et al. 2014, Expert Opin Ther Targets Expert Opin Ther Targets. 2014; 18(10):1121-30), head injury (Bullock M R et al., Ann N Y Acad Sci. 1999; 890:51-8), spinal cord injury, stroke (Yang Y et al., J Neurosurg. 2003; 98(2):397-403), epilepsy (Naspolini A P et al., Epilepsy Res. 2012 June; 100 (1-2):12-9), movement disorders (e.g. dyskinesias) (Morissette M et al., Mov Disord. 2006; 21(1):9-17), various neurodegenerative diseases (e.g. amyotrophic lateral sclerosis (Fuller P I et al., Neurosci Lett. 2006; 399 (1-2):157-61) or neurodegeneration associated with bacterial or chronic infections), pain (e.g. chronic, cancer, post-operative and neuropathic pain (Wu L J and Zhuo M, Neurotherapeutics. 2009; 6(4):693-702), diabetic neuropathy, migraine (Peeters M et al., J Pharmacol Exp Ther. 2007; 321(2):564-72), cerebral ischemia (Yuan H et al., Neuron. 2015; 85(6):1305-18), schizophrenia (Grimwood S et al., Neuroreport. 1999; 10(3):461-5), encephalitis (Dalmau J. et al., Lancet Neurol. 2008; 7(12): 1091-8), autism and autism spectrum disorders (Won H. et al., Nature. 2012; 486(7402):261-5), memory and learning disorders (Tang, Y. P. et al., Nature. 1999; 401(6748):63-9), obsessive compulsive disorder (Arnold P D et al., Psychiatry Res. 2009; 172(2):136-9), attention deficit hyperactivity disorder (ADHD) (Dorval K M et al., Genes Brain Behav. 2007; 6(5):444-52), and addictive illnesses (e.g. alcohol addiction, drug addiction) (Nagy J, 2004, Curr Drug Targets CNS Neurol Disord. 2004; 3(3): 169-79; Shen H et al., Proc Natl Acad Sci USA. 2011; 108(48):19407-12).

SUMMARY OF THE INVENTION

Provided herein are compounds which inhibit the NR2B receptor.

In one aspect, provided herein are compounds, and pharmaceutically acceptable salts, solvates, or N-oxides thereof, having the structure of Formula (I):

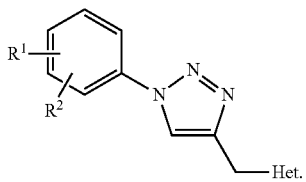

(I)

The present invention also provides a pharmaceutical composition comprising a therapeutically effective amount of a compound of Formula (I), or a pharmaceutically acceptable salt, solvate, or N-oxide thereof for use in medicine, and optionally a pharmaceutically acceptable carrier. The pharmaceutical composition may be used in human or veterinary medicine.

The present invention further provides a method of treating disorders associated with NMDA hyperactivity, most preferably with NR2B hyperactivity, the method comprising administering to a patient in need thereof a therapeutically effective amount of a compound of Formula (I), or a pharmaceutically acceptable salt, solvate, or N-oxide thereof.

The present invention also provides a method of treating a central nervous system disorder in a patient in need thereof comprising, administering to said patient a therapeutically effective amount of a compound of Formula (I), or a pharmaceutically acceptable salt, solvate, or N-oxide thereof.

The present invention also provides a compound for use in any of the methods described herein. The present invention further provides use of a compound for the preparation of a medicament for use in any of the methods described herein.

The details of one or more embodiments of the invention are set forth in the accompanying drawings and the description below. Other features, objects, and advantages of the invention will be apparent from the description and drawings, and from the claims.

DETAILED DESCRIPTION

Exemplary Compounds and Compositions

The present invention provides, inter alia, a compound of Formula (I):

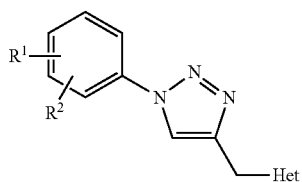

(I)

or pharmaceutically acceptable salts, solvates, or N-oxides thereof; wherein:

Het represents one of the following heterocyclic ring structures:

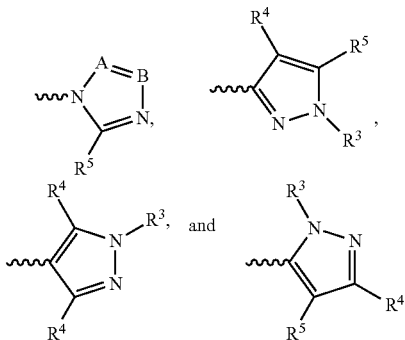

wherein A represents N or C—$R^4$: and B represents N or C—$R^4$, with the provision that at least one of A and B represents C—$R^4$, $R^1$ and $R^2$ in each case independently represent, hydrogen, halogen, $C_{1-6}$ alkyl, straight or branched, optionally substituted with at least one substituent, e.g. 1, 2 or 3 substituents, selected from hydroxy, halogen, $C_{1-3}$ alkoxy optionally substituted with at least one halogen atom, e.g. with 1, 2 or 3 halogen atoms, and $C_{3-6}$ cycloalkyl, optionally substituted with at least one halogen atom, e.g. with 1, 2 or 3 halogen atoms, $C_{3-6}$ cycloalkyl, optionally substituted with at least one substituent, e.g. 1, 2 or 3 substituents, selected from hydroxy, halogen, $C_{1-3}$ alkyl optionally substituted with at least one halogen atom, e.g. with 1, 2 or 3 halogen atoms, and $C_{1-3}$ alkoxy optionally substituted with at least one halogen atom, e.g. with 1, 2 or 3 halogen atoms, $C_{1-6}$ alkoxy, optionally substituted with at least one substituent, e.g. 1, 2 or 3 substituents selected from hydroxy, halogen, $C_{1-3}$ alkoxy optionally substituted with at least one halogen atom, e.g. with 1, 2 or 3 halogen atoms, and $C_{3-6}$ cycloalkyl, optionally substituted with at least one halogen atom, e.g. with 1, 2 or 3 halogen atoms, —O—$C_{3-6}$ cycloalkyl, optionally substituted with at least one substituent, e.g. 1, 2 or 3 substituents selected from hydroxy, halogen, $C_{1-3}$ alkyl optionally substituted with at least one halogen atom, e.g. with 1, 2 or 3 halogen atoms, and $C_{1-3}$ alkoxy, optionally substituted with at least one halogen atom, e.g. with 1, 2 or 3 halogen atoms, —S—$C_{1-3}$ alkyl, optionally substituted with at least one halogen atom, e.g. with 1, 2 or 3 halogen atoms, —$SO_2$—$C_{1-3}$ alkyl, optionally substituted with at least one halogen atom, e.g. with 1, 2 or 3 halogen atoms, and

—$SF_5$, or $R^1$ and $R^2$ together can form a 5 to 7 member carbocycle, optionally substituted with at least one substituent, e.g. 1, 2 or 3 substituents selected from hydroxy, halogen, $C_{1-3}$ alkyl optionally substituted with at least one halogen atom, e.g. with 1, 2 or 3 halogen atoms, and $C_{1-3}$ alkoxy optionally substituted with at least one halogen atom, e.g. with 1, 2 or 3 halogen atoms, or a 5 to 7 member heterocycle containing one to three heteroatoms which can be O, S or N, optionally substituted with at least one substituent, e.g. 1, 2 or 3 substituents, selected from hydroxy, halogen, $C_{1-3}$ alkyl optionally substituted with at least one halogen atom, e.g. with 1, 2 or 3 halogen atoms, and $C_{1-3}$ alkoxy optionally substituted with at least one halogen atom, e.g. with 1, 2 or 3 halogen atoms, $R^3$ represents hydrogen, $C_{1-5}$ alkyl, straight or branched, optionally substituted with at least one substituent, e.g. with 1, 2 or 3 substituents, selected from
halogen atoms,
hydroxy,
$C_{1-3}$ alkoxy, optionally substituted with at least one halogen atom, e.g. with 1, 2 or 3 halogen atoms, and
$C_{3-6}$ cycloalkyl optionally substituted with at least one halogen atom, e.g. with 1, 2 or 3 halogen atoms, $C_{3-6}$ cycloalkyl, optionally substituted with at least one substituent, e.g. 1, 2 or 3 substituents selected from hydroxy, halogen, $C_{1-3}$ alkyl optionally substituted with at least one halogen atom, e.g. with 1, 2 or 3 halogen atoms, and $C_{1-3}$ alkoxy optionally substituted with at least one halogen atom, e.g. with 1, 2 or 3 halogen atoms, and O—$C_{3-6}$ cycloalkyl, optionally substituted with at least one substituent, e.g. 1, 2 or 3 substituents selected from hydroxy, halogen, $C_{1-3}$ alkyl optionally substituted with at least one halogen atom, e.g. with 1, 2 or 3 halogen atoms, and $C_{1-3}$ alkoxy optionally substituted with at least one halogen atom, e.g. with 1, 2 or 3 halogen atoms, $R^4$ and $R^5$ in each case independently represent
hydrogen,
amino, including $C_{1-6}$ alkylamino and di($C_{1-6}$) alkylamino,
halogen,
$C_{1-5}$ alkyl, straight or branched, optionally substituted with at least one substituent, e.g. with 1, 2 or 3 substituents, selected from
halogen atoms,
hydroxy,
$C_{1-3}$ alkoxy, optionally substituted with at least one halogen atom, e.g. with 1, 2 or 3 halogen atoms, and
$C_{3-6}$ cycloalkyl optionally substituted with at least one halogen atom, e.g. with 1, 2 or 3 halogen atoms,
$C_{1-5}$ alkoxy, straight or branched, optionally substituted with at least one substituent, e.g. 1, 2 or 3 substituents, selected from hydroxy, halogen, $C_{1-3}$ alkoxy optionally substituted with at least one halogen atom, e.g. with 1, 2 or 3 halogen atoms, and $C_{3-6}$ cycloalkyl, optionally substituted with at least one halogen atom, e.g. with 1, 2 or 3 halogen atoms,
$C_{3-6}$ cycloalkyl, optionally substituted with at least one substituent, e.g. 1, 2 or 3 substituents selected from hydroxy, halogen, $C_{1-3}$ alkyl optionally substituted with at least one halogen atom, e.g. with 1, 2 or 3 halogen atoms, and $C_{1-3}$ alkoxy optionally substituted with at least one halogen atom, e.g. with 1, 2 or 3 halogen atoms, and
O—$C_{3-6}$ cycloalkyl, optionally substituted with at least one substituent, e.g. 1, 2 or 3 substituents selected from hydroxy, halogen, $C_{1-3}$ alkyl optionally substituted with at least one halogen atom, e.g. with 1, 2 or 3 halogen atoms, and $C_{1-3}$ alkoxy optionally substituted with at least one halogen atom, e.g. with 1, 2 or 3 halogen atoms.

In specific embodiments, one of $R^1$ and $R^2$ does not represent hydrogen, or both of $R^1$ and $R^2$ do not represent hydrogen. When different from hydrogen, $R^1$ and $R^2$ are preferably located at a meta- or at the para-position of the phenyl ring for example, the phenyl ring may contain substituents $R^1$ and/or $R^2$ different from H at position 3, 4, 3 and 4, or 3 and 5, and the substituents at all other positions are H.

In other embodiments, $R^1$ and $R^2$ independently from each other represent:

F, Cl, Br, $C_{1-4}$ alkyl, straight or branched, optionally substituted with at least one halogen atom, e.g. with 1, 2 or 3 halogen atoms, e.g. methyl, difluoromethyl, trifluoromethyl, 1,1-difluoroethyl, $C_{3-6}$ cycloalkyl, optionally substituted with at least one halogen atom, e.g. with 1, 2 or 3 halogen atoms, e.g. cyclopropyl, cyclobutyl, cyclopentyl, $C_{1-3}$ alkoxy, optionally substituted with at least one halogen atom, e.g. with 1, 2 or 3 halogen atoms, e.g. methoxy, difluoromethoxy, trifluoromethoxy, 1,1-difluoroethoxy, $C_{1-3}$ alkoxy-$C_{1-3}$ alkyl, optionally substituted with at least one halogen atom, e.g. with 1, 2 or 3 halogen atoms, e.g. 2-methoxyethyl, $C_{3-6}$ cycloalkyl-$C_{1-3}$ alkyl, optionally substituted with at least one halogen atom, e.g. with 1, 2 or 3 halogen atoms, e.g cyclopropylmethyl, and $C_{3-6}$ cycloalkyl-$C_{1-3}$ alkoxy, optionally substituted with at least one halogen atom, e.g. with 1, 2 or 3 halogen atoms, e.g. cyclopropylmethoxy.

In one embodiment Het may represent

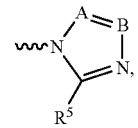

wherein A represents N or C—$R^4$; B represents C—$R^4$; $R^4$ and $R^5$ in each case independently represent
hydrogen,
amino,
—F, Cl,
$C_{1-3}$ alkyl, straight or branched, optionally substituted with at least one halogen atom, e.g. with 1, 2 or 3 halogen atoms, hydroxy, and/or $C_{1-3}$ alkoxy, optionally substituted with at least one halogen atom, e.g. with 1, 2 or 3 halogen atoms,
$C_{1-3}$ alkoxy, straight or branched, optionally substituted with at least one halogen atom, e.g. with 1, 2 or 3 halogen atoms,
$C_{3-6}$ cycloalkyl, optionally substituted with at least one halogen atom, e.g. with 1, 2 or 3 halogen atoms, and
$C_{3-6}$ cycloalkyl-$C_{1-3}$ alkyl, optionally substituted with at least one halogen atom, e.g. with 1, 2 or 3 halogen atoms.

In this embodiment, $R^4$ and $R^5$ are each independently selected from hydrogen, methyl, ethyl, n-propyl, iso-propyl, n-butyl, tert-butyl, trifluoromethyl, 2-fluoroethyl, 2-hydroxyethyl, cyclopropyl, cyclobutyl, cyclopentyl, and hydroxymethyl.

In other embodiments Het may represent:

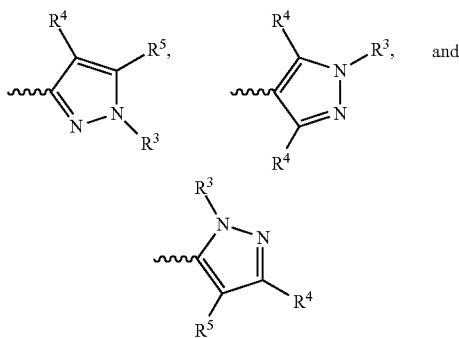

R³ represents
  hydrogen,
  C$_{1-3}$ alkyl, straight or branched, optionally substituted with at least one halogen atom, e.g. with 1, 2 or 3 halogen atoms, hydroxy, and/or C$_{1-3}$ alkoxy, optionally substituted with at least one halogen atom, e.g. with 1, 2 or 3 halogen atoms,
  C$_{3-6}$ cycloalkyl, optionally substituted with at least one halogen atom, e.g. with 1, 2 or 3 halogen atoms, and
  C$_{3-6}$ cycloalkyl-C$_{1-3}$ alkyl, optionally substituted with at least one halogen atom, e.g. with 1, 2 or 3 halogen atoms, and R⁴ and R⁵ independently from each other represent
  hydrogen,
  amino,
  F, Cl,
  C$_{1-3}$ alkyl, straight or branched, optionally substituted with at least one halogen atom, e.g. with 1, 2 or 3 halogen atoms, hydroxy, and/or C$_{1-3}$ alkoxy, optionally substituted with at least one halogen atom, e.g. with 1, 2 or 3 halogen atoms,
  C$_{1-3}$ alkoxy, straight or branched, optionally substituted with at least one halogen atom, e.g. with 1, 2 or 3 halogen atoms,
  C$_{3-6}$ cycloalkyl, optionally substituted with at least one halogen atom, e.g. with 1, 2 or 3 halogen atoms, and
  C$_{3-6}$ cycloalkyl-C$_{1-3}$ alkyl, optionally substituted with at least one halogen atom, e.g. with 1, 2 or 3 halogen atoms.

In some embodiments, R³, R⁴ and/or R⁵ are e.g. selected from hydrogen, methyl, ethyl, n-propyl, isopropyl, n-butyl, tert-butyl, trifluoromethyl, 2-fluoroethyl, 2-hydroxyethyl, cyclopropyl, cyclobutyl, and cyclopentyl.

Specific non-limiting compounds of the present invention are:
1-(4-Chloro-phenyl)-4-(3,5-dimethyl-[1,2,4]triazol-1-ylmethyl)-1H-[1,2,3]triazole
1-(4-Chloro-phenyl)-4-(5-propyl-[1,2,4]triazol-1-ylmethyl)-1H-[1,2,3]triazole
1-(4-Chloro-phenyl)-4-(3-propyl-[1,2,4]triazol-1-ylmethyl)-1H-[1,2,3]triazole
1-(4-Chloro-phenyl)-4-(3-isopropyl-[1,2,4]triazol-1-ylmethyl)-1H-[1,2,3]triazole
1-(4-Chloro-phenyl)-4-(5-ethyl-[1,2,4]triazol-1-ylmethyl)-1H-[1,2,3]triazole
1-(4-Chloro-phenyl)-4-(3-ethyl-[1,2,4]triazol-1-ylmethyl)-1H-[1,2,3]triazole
1-(4-Chloro-phenyl)-4-(5-isopropyl-[1,2,4]triazol-1-ylmethyl)-1H-[1,2,3]triazole
1-(4-Chloro-phenyl)-4-(5-methyl-[1,2,4]triazol-1-ylmethyl)-1H-[1,2,3]triazole
1-(4-Chloro-phenyl)-4-(3-methyl-[1,2,4]triazol-1-ylmethyl)-1H-[1,2,3]triazole
1-(4-Chloro-phenyl)-4-(3,5-dicyclopropyl-[1,2,4]triazol-1-ylmethyl)-1-[1,2,3]triazole
1-(4-Chloro-phenyl)-4-(5-cyclobutyl-[1,2,4]triazol-1-ylmethyl)-1H-[1,2,3]triazole
1-(4-Chloro-phenyl)-4-(3-cyclobutyl-[1,2,4]triazol-1-ylmethyl)-1H-[1,2,3]triazole
1-(4-Chloro-phenyl)-4-(3-cyclopropyl-[1,2,4]triazol-1-ylmethyl)-1H-[1,2,3]triazole
1-(4-Chloro-phenyl)-4-(5-cyclopentyl-[1,2,4]triazol-1-ylmethyl)-1H-[1,2,3]triazole
1-(4-Chloro-phenyl)-4-(3-cyclopentyl-[1,2,4]triazol-1-ylmethyl)-1H-[1,2,3]triazole
1-(4-Chloro-phenyl)-4-(5-cyclopropyl-[1,2,4]triazol-1-ylmethyl)-1H-[1,2,3]triazole
1-(4-Chloro-phenyl)-4-(3-trifluoromethyl-[1,2,4]triazol-1-ylmethyl)-1H-[1,2,3]triazole
1-(4-Chloro-phenyl)-4-(2-propyl-imidazol-1-ylmethyl)-1H-[1,2,3]triazole
4-(5-tert-Butyl-[1,2,4]triazol-1-ylmethyl)-1-(4-chloro-phenyl)-1H-[1,2,3]triazole
4-(3-tert-Butyl-[1,2,4]triazol-1-ylmethyl)-1-(4-chloro-phenyl)-1H-[1,2,3]triazole
1-(4-Chloro-phenyl)-4-(5-cyclobutyl-3-methyl-[1,2,4]triazol-1-ylmethyl)-1H-[1,2,3]triazole
1-(4-Chloro-phenyl)-4-(3-cyclobutyl-5-methyl-[1,2,4]triazol-1-ylmethyl)-1H-[1,2,3]triazole
1-(4-Chloro-phenyl)-4-(2-isopropyl-imidazol-1-ylmethyl)-1H-[1,2,3]triazole
1-(4-Chloro-phenyl)-4-(2-methyl-imidazol-1-ylmethyl)-1H-[1,2,3]triazole
1-(4-Chloro-phenyl)-4-(2-ethyl-imidazol-1-ylmethyl)-1H-[1,2,3]triazole
4-(2-amino-imidazol-1-ylmethyl)-1-(3-fluoro-4-difluoromethyl-phenyl)-1H-[1,2,3]triazole
4-(2-amino-imidazol-1-ylmethyl)-1-(4-chloro-3-difluoromethyl-phenyl)-1H-[1,2,3]triazole
4-(2-amino-imidazol-1-ylmethyl)-1-(4-fluoro-3-difluoromethyl-phenyl)-1H-[1,2,3]triazole
4-(2-Chloro-imidazol-1-ylmethyl)-1-(4-chloro-phenyl)-1H-[1,2,3]triazole
4-(2-Butyl-imidazol-1-ylmethyl)-1-(4-chloro-phenyl)-1H-[1,2,3]triazole
4-(2-Hydroxymethyl-imidazol-1-ylmethyl)-1-(4-chloro-phenyl)-1H-[1,2,3]triazole
1-(4-Chloro-phenyl)-4-(2-cyclopropyl-imidazol-1-ylmethyl)-1H-[1,2,3]triazole
4-(2-tert-Butyl-imidazol-1-ylmethyl)-1-(4-chloro-phenyl)-1H-[1,2,3]triazole
1-(4-Chloro-phenyl)-4-(3-methyl-[1,2,4]triazol-4-ylmethyl)-1H-[1,2,3]triazole
1-(3,4-Dichloro-phenyl)-4-(2-methyl-imidazol-1-ylmethyl)-1H-[1,2,3]triazole
1-(3,4-Dichloro-phenyl)-4-(2-ethyl-imidazol-1-ylmethyl)-1H-[1,2,3]triazole
1-(3,4-Dichloro-phenyl)-4-(2-propyl-imidazol-1-ylmethyl)-1H-[1,2,3]triazole
1-(3,4-Dichloro-phenyl)-4-(2-isopropyl-imidazol-1-ylmethyl)-1H-[1,2,3]triazole
4-(2-Cyclopropyl-imidazol-1-ylmethyl)-1-(3,4-dichloro-phenyl)-1H-[1,2,3]triazole
4-(2-Butyl-imidazol-1-ylmethyl)-1-(3,4-dichloro-phenyl)-1H-[1,2,3]triazole 4-(2-tert-Butyl-imidazol-1-ylmethyl)-1-(3,4-dichloro-phenyl)-1H-[1,2,3]triazole
4-(2-Cyclobutyl-imidazol-1-ylmethyl)-1-(3,4-dichloro-phenyl)-1H-[1,2,3]triazole
4-[2-(2-Hydroxyethyl)-imidazol-1-ylmethyl]-1-(3,4-dichloro-phenyl)-1H-[1,2,3]triazole
1-(3,4-Dichloro-phenyl)-4-[2-(2-fluoro-ethyl)-imidazol-1-ylmethyl]-1H-[1,2,3]triazole
1-(3-Chloro-4-fluoro-phenyl)-4-(2-ethyl-imidazol-1-ylmethyl)-1H-[1,2,3]triazole
1-(3-Chloro-4-fluoro-phenyl)-4-(2-propyl-imidazol-1-ylmethyl)-1H-[1,2,3]triazole
1-(3-Chloro-4-fluoro-phenyl)-4-(2-cyclopropyl-imidazol-1-ylethyl)-1H-[1,2,3]triazole
4-(2-Butyl-imidazol-1-ylmethyl)-1-(3-chloro-4-fluoro-phenyl)-1H-[1,2,3]triazole
4-(3,5-Dimethyl-[1,2,4]triazol-1-ylmethyl)-1-phenyl-1H-[1,2,3]triazole
4-(5-Hydroxymethyl-3-methyl-[1,2,4]triazol-1-ylmethyl)-1-phenyl-1H-[1,2,3]triazole
4-(3-Hydroxymethyl-5-methyl-[1,2,4]triazol-1-ylmethyl)-1-phenyl-1H-[1,2,3]triazole
1-(2,4-Dichloro-phenyl)-4-(2-methyl-imidazol-1-ylmethyl)-1H-[1,2,3]triazole
1-(4-Chloro-3-fluoro-phenyl)-4-(2-methyl-imidazol-1-ylmethyl)-1H-[1,2,3]triazole
1-(3-Chloro-4-fluoro-phenyl)-4-(2-methyl-imidazol-1-ylmethyl)-1H-[1,2,3]triazole
1-(4-Fluoro-2-methoxy-phenyl)-4-(2-methyl-imidazol-1-ylmethyl)-1H-[1,2,3]triazole
1-(3-Fluoro-4-methyl-phenyl)-4-(2-methyl-imidazol-1-ylmethyl)-1H-[1,2,3]triazole
1-(4-Fluoro-3-methyl-phenyl)-4-(2-methyl-imidazol-1-ylmethyl)-1H-[1,2,3]triazole
1-(4-Chloro-3-methyl-phenyl)-4-(2-methyl-imidazol-1-ylmethyl)-1H-[1,2,3]triazole
1-(4-Chloro-3-trifluoromethyl-phenyl)-4-(2-methyl-imidazol-1-ylmethyl)-1H-[1,2,3]triazole
4-(2-Methyl-imidazol-1-ylmethyl)-1-(3-trifluoromethoxy-phenyl)-1H-[1,2,3]triazole
4-(2-Methyl-imidazol-1-ylmethyl)-1-(3-trifluoromethyl-phenyl)-1H-[1,2,3]triazole
4-(2-Methyl-imidazol-1-ylmethyl)-1-(4-trifluoromethyl-phenyl)-1H-[1,2,3]triazole
4-(2-Cyclopropyl-imidazol-1-ylmethyl)-1-(2,4-dichloro-phenyl)-1H-[1,2,3]triazole
1-(4-Chloro-3-fluoro-phenyl)-4-(2-cyclopropyl-imidazol-1-ylmethyl)-1H-[1,2,3]triazole
4-(2-Cyclopropyl-imidazol-1-ylmethyl)-1-(4-fluoro-2-methoxy-phenyl)-1H-[1,2,3]triazole
4-(2-Cyclopropyl-imidazol-1-ylmethyl)-1-(3-fluoro-4-methyl-phenyl)-1H-[1,2,3]triazole
4-(2-Cyclopropyl-imidazol-1-ylmethyl)-1-(4-fluoro-3-methyl-phenyl)-1H-[1,2,3]triazole
1-(4-Chloro-3-methyl-phenyl)-4-(2-cyclopropyl-imidazol-1-ylmethyl)-1H-[1,2,3]triazole
1-(4-Chloro-3-trifluoromethyl-phenyl)-4-(2-cyclopropyl-imidazol-1-ylmethyl)-1H-[1,2,3]triazole
4-(2-Cyclopropyl-imidazol-1-ylmethyl)-1-(3-trifluoromethoxy-phenyl)-1H-[1,2,3]triazole
4-(2-Cyclopropyl-imidazol-1-ylmethyl)-1-(3-trifluoromethyl-phenyl)-1H-[1,2,3]triazole
4-(2-Cyclopropyl-imidazol-1-ylmethyl)-1-(4-trifluoromethyl-phenyl)-1H-[1,2,3]triazole
1-(4-Chloro-3-methyl-phenyl)-4-(2-ethyl-imidazol-1-ylmethyl)-1H-[1,2,3]triazole
1-(4-Chloro-3-methyl-phenyl)-4-(2-isopropyl-imidazol-1-ylmethyl)-1H-[1,2,3]triazole
4-(2-Ethyl-imidazol-1-ylmethyl)-1-(3-trifluoromethoxy-phenyl)-1H-[1,2,3]triazole
4-(2-Isopropyl-imidazol-1-ylmethyl)-1-(3-trifluoromethoxy-phenyl)-1H-[1,2,3]triazole
1-(4-Chloro-3-methyl-phenyl)-4-[2-(2-hydroxy-ethyl)-imidazol-1-ylmethyl]-1H-[1,2,3]triazole
1-(4-Chloro-3-methyl-phenyl)-4-[2-(2-fluoro-ethyl)-imidazol-1-ylmethyl]-1H-[1,2,3]triazole
1-(3-Cyclopropyl-phenyl)-4-(2-methyl-imidazol-1-ylmethyl)-1H-[1,2,3]triazole
1-(3-Methanesulfonyl-phenyl)-4-(2-methyl-imidazol-1-ylmethyl)-1H-[1,2,3]triazole
1-(3-Cyclopropyl-phenyl)-4-[2-(2-hydroxy-ethyl)-imidazol-1-ylmethyl]-1H-[1,2,3]triazole
4-[2-(2-Hydroxy-ethyl)-imidazol-1-ylmethyl]-1-(3-methanesulfonyl-phenyl)-1H-[1,2,3]triazole
4-[2-(2-Fluoro-ethyl)-imidazol-1-ylmethyl]-1-(3-methanesulfonyl-phenyl)-1H-[1,2,3]triazole
1-(3-Difluoromethyl-4-fluoro-phenyl)-4-(2-methyl-imidazol-1-ylmethyl)-1H-[1,2,3]triazole
4-(2-Cyclopropyl-imidazol-1-ylmethyl)-1-(3-difluoromethyl-4-fluoro-phenyl)-1H-[1,2,3]triazole
1-(3-Difluoromethyl-4-fluoro-phenyl)-4-(2-ethyl-imidazol-1-ylmethyl)-1H-[1,2,3]triazole
1-(3-Difluoromethyl-4-fluoro-phenyl)-4-(2-isopropyl-imidazol-1-ylmethyl)-1H-[1,2,3]triazole
1-(3-Difluoromethyl-4-fluoro-phenyl)-4-(2-propyl-imidazol-1-ylmethyl)-1H-[1,2,3]triazole
1-(3-Difluoromethyl-4-fluoro-phenyl)-4-(2-butyl-imidazol-1-ylmethyl)-1H-[1,2,3]triazole
1-(3-Difluoromethyl-4-fluoro-phenyl)-4-(2-tert.butyl-imidazol-1-ylmethyl)-1H-[1,2,3]triazole
1-(3-Difluoromethyl-4-fluoro-phenyl)-4-[2-(2-hydroxy-ethyl)-imidazol-1-ylmethyl]-1H-[1,2,3]triazole
1-(4-Chloro-3-difluoromethyl-phenyl)-4-(2-methyl-imidazol-1-ylmethyl)-1H-[1,2,3]triazole
1-(4-Chloro-3-difluoromethyl-phenyl)-4-(2-cyclopropyl-imidazol-1-ylmethyl)-1H-[1,2,3]triazole
1-(4-Chloro-3-difluoromethyl-phenyl)-4-(2-ethyl-imidazol-1-ylmethyl)-1H-[1,2,3]triazole
1-(4-Chloro-3-difluoromethyl-phenyl)-4-(2-isopropyl-imidazol-1-ylmethyl)-1H-[1,2,3]triazole
1-(4-Chloro-3-difluoromethoxy-phenyl)-4-(2-methyl-imidazol-1-ylmethyl)-1H-[1,2,3]triazole
1-(4-Chloro-3-difluoromethoxy-phenyl)-4-(2-cyclopropyl-imidazol-1-ylmethyl)-1H-[1,2,3]triazole
4-(2-tert-Butyl-imidazol-1-ylmethyl)-1-(4-chloro-3-difluoromethoxy-phenyl)-1H-[1,2,3]triazole
1-(4-Chloro-3-difluoromethoxy-phenyl)-4-(2-ethyl-imidazol-1-ylmethyl)-1H-[1,2,3]triazole
1-(4-Chloro-3-difluoromethoxy-phenyl)-4-(2-isopropyl-imidazol-1-ylmethyl)-1H-[1,2,3]triazole
1-(4-Chloro-3-difluoromethoxy-phenyl)-4-[2-(2-hydroxy-ethyl)-imidazol-1-ylmethyl]-1H-[1,2,3]triazole
1-(4-Chloro-3-difluoromethoxy-phenyl)-4-[2-(2-fluoro-ethyl)-imidazol-1-ylmethyl]-1H-[1,2,3]triazole
1-(3-Difluoromethoxy-4-fluoro-phenyl)-4-(2-methyl-imidazol-1-ylmethyl)-1H-[1,2,3]triazole
1-(3-Difluoromethoxy-4-fluoro-phenyl)-4-[2-(2-hydroxy-ethyl)-imidazol-1-ylmethyl]-1H-[1,2,3]triazole
1-(3-Difluoromethyl-5-fluoro-phenyl)-4-(2-methyl-imidazol-1-ylmethyl)-1H-[1,2,3]triazole
1-(3-Difluoromethyl-5-fluoro-phenyl)-4-[2-(2-hydroxy-ethyl)-imidazol-1-ylmethyl]-1H-[1,2,3]triazole 1-(3-Difluoromethyl-5-fluoro-phenyl)-4-[2-(2-fluoro-ethyl)-imidazol-1-ylmethyl]-1H-[1,2,3]triazole 1-[3-(1,1-Difluoro-ethyl)-4-fluoro-phenyl]-4-(2-methyl-imidazol-1-ylmethyl)-1H-[1,2,3]triazole 1-[3-(1,1-Difluoro-ethyl)-4-fluoro-phenyl]-4-[2-(2-hydroxy-ethyl)-imidazol-1-ylmethyl]-1H-[1,2,3]triazole 4-(2-Methyl-imidazol-1-ylmethyl)-1-(4-pentafluoro-sulfane-phenyl)-1H-[1,2,3]triazole 4-(2-hydroxy-ethyl-imidazol-1-ylmethyl)-1-(4-pentafluoro-sulfane-phenyl)-1H-[1,2,3]triazole 1-(3-Chloro-4-fluoro-phenyl)-4-(2-methyl-2H-pyrazol-3-ylmethyl)-1H-[1,2,3]triazole 1-(4-Chloro-3-difluoromethoxy-phenyl)-4-(2-amino-imidazol-1-ylmethyl)-1H-[1,2,3]triazole 4-(2-amino-imidazol-1-ylmethyl)-1-(3-fluoro-5-difluoromethyl-phenyl)-1H-[1,2,3]triazole The present invention also provides a pharmaceutical composition comprising a therapeutically effective amount of a compound of Formula (I), or a pharmaceutically acceptable salt, solvate, or N-oxide thereof for use in medicine, and optionally a pharmaceutically acceptable carrier. The pharmaceutical composition may be used in human or veterinary medicine.

Certain Definitions

The term "alkyl" refers to a straight- or branched-chain alkyl group having from 1 to 12 carbon atoms in the chain. In some embodiments, an alkyl group is a $C_1$-$C_6$ alkyl group. In some embodiments, an alkyl group is a $C_1$-$C_4$ alkyl group. Examples of alkyl groups include methyl (Me) ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. In some embodiments, alkyl refers to straight or branched chain hydrocarbon groups. Specific examples in these embodiments are methyl, ethyl, propyl (e.g., n-propyl and isopropyl), butyl (e.g., n-butyl and t-butyl) hexyl and the like.

The term "haloalkyl" refers to a straight- or branched-chain alkyl group having from 1 to 12 carbon atoms in the chain and having at least one of the hydrogens replaced with a halogen. In some embodiments, a haloalkyl group is a $C_1$-$C_6$ haloalkyl group. In some embodiments, a haloalkyl group is a $C_1$-$C_4$ haloalkyl group. One exemplary substitutent is fluoro. Preferred substituted alkyl groups of the invention include trihalogenated alkyl groups such as trifluoromethyl groups. Haloalkyl includes and is not limited to $CF_3$, $CH_2F$, —$CHF_2$, —$CH_2Cl$, —$CH_2$—$CF_3$, and the like. In specific examples, the term (halo)alkyl refers to alkyl substituted by at least one halogen atom. Examples of these embodiments include fluoromethyl, difluoromethyl, trifluoromethyl, 2-fluoroethyl.

"Cycloalkyl" refers to monocyclic, non-aromatic hydrocarbon groups having from 3 to 7 carbon atoms. Examples of cycloalkyl groups include, for example, cyclopropyl, cyclobutyl, cyclopentyl, cyclohexyl, and the like.

The term "cyclic group" includes fully saturated, partially unsaturated and aromatic carbocyclic or heterocyclic rings, including aromatic ("aryl" or "heteroaryl") or nonaromatic cyclic groups, for example, 5 to 7 membered monocyclic ring systems, which may have at least one heteroatom in at least one carbon atom-containing ring. A heterocyclic group containing a heteroatom may have 1, 2, or 3 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. In some embodiments, one or more carbon atoms of the heterocyclic ring are oxidized to form a carbonyl group. The cyclic group may be unsubstituted or carry one or more substituents, e.g. halogen, $C_{1-6}$ (halo)alkyl, $C_{1-6}$ (halo)alkoxy, OH, etc.

The term "alkoxy" includes a straight chain or branched alkyl group with a terminal oxygen linking the alkyl group to the rest of the molecule. In some embodiments, an alkoxy group is a C1-C6 alkoxy group. In some embodiments, an alkoxy group is a $C_1$-$C_4$ alkoxy group. Alkoxy includes methoxy, ethoxy, propoxy, isopropoxy, butoxy, t-butoxy, pentoxy and so on. In specific embodiments, the term alkoxy, employed alone or in combination with other terms, refers to a group of formula —O-alkyl. Example alkoxy groups in these embodiments include methoxy, ethoxy, propoxy (e.g. n-propoxy and isopropoxy), t-butoxy, hexyloxy and the like. The term (halo)alkoxy refers to alkoxy substituted by at least one halogen atom. Examples of (halo)alkoxy groups include fluoromethoxy, difluoromethoxy, and trifluoromethoxy.

The term "heterocycle" represents" a mono- or bi-cyclic hydrocarbon ring structure optionally containing heteroatoms selected from O, S, and N. Heterocyclyl rings can have 2 to 10 carbon atoms in the ring.

The term "halogen" represents chlorine, fluorine, bromine, or iodine. The term "halo" represents chloro, fluoro, bromo, or iodo. In specific embodiments, halo refers to fluorine, chlorine, bromine and iodine, particularly to fluorine, chlorine and bromine, more particularly to fluorine and chlorine.

"Benzyl" and —$CH_2$-phenyl are used interchangeably.

"GluN2B receptors" refers to NMDA receptors containing the GluN2B or NR2B subunit.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans. In specific embodiments, "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) may form salts which are also within the scope of this invention. Reference to a compound of the Formula (I) herein is understood to include reference to salts thereof, unless otherwise indicated. In various embodiments, the term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise an acid moiety such as a carboxyl group). Also included herein are quaternary ammonium salts such as alkylammonium salts. Salts of the compounds of the Formula (I) may be formed, for example, by reacting a compound I with an amount of acid or base, such as an equivalent amount, in a medium such as one in which the salt precipitates or in an aqueous medium followed by lyophilisation.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoate, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts (formed, for example, where the R substituents comprise an acidic moiety such as a carboxyl group) include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines, N-methyl-D-glucamines, N-methyl-D-glucamides, t-butyl amines, and salts with amino acids such as arginine, lysine and the like. The basic nitrogen-containing groups may be quaternized with agents such as lower alkyl halides (e.g., methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like.

In specific embodiments "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418 and *Journal of Pharmaceutical Science*, 66, 2 (1977), each of which is incorporated herein by reference in its entirety.

"Pharmaceutically acceptable vehicle" refers to a diluent, adjuvant, excipient or carrier with which a compound of the invention is administered. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

"Subject" includes humans. The terms "human," "patient," and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

In treatment methods according to the invention, a therapeutically effective amount of a pharmaceutical agent according to the invention is administered to a subject suffering from or diagnosed as having such a disease, disorder, or condition. A "therapeutically effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subjects previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

"Compounds of the present invention," "compounds of the invention" and equivalent expressions, are meant to embrace compounds of the Formula (I) as described herein, which expression includes the pharmaceutically acceptable salts, the solvates, e.g., hydrates, where the context so permits, or the N-oxides thereof. Similarly, reference to intermediates, whether or not they themselves are claimed, is meant to embrace their salts, solvates, and N-oxides, where the context so permits.

Furthermore, in the case of the compounds of the invention which contain an asymmetric carbon atom, the invention relates to the D form, the L form and D, L mixtures and also, where more than one asymmetric carbon atom is present, to the diastereomeric forms. Those compounds of the invention which contain asymmetric carbon atoms, and which as a rule accrue as racemates, can be separated into the optically active isomers in a known manner, for example using an optically active acid. However, it is also possible to use an optically active starting substance from the outset, with a corresponding optically active or diastereomeric compound then being obtained as the end product.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Exemplary prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

Also included are solvates and hydrates of the compounds of Formula (I) and solvates and hydrates of their pharmaceutically acceptable salts.

The term "compound" as used herein is meant to include all stereoisomers, geometric isomers, tautomers, and isotopes of the structures depicted, unless otherwise indicated.

As used herein, the term "isotopic variant" refers to a compound that contains unnatural proportions of isotopes at one or more of the atoms that constitute such compound. For example, an "isotopic variant" of a compound can be radiolabeled, that is, contain one or more non-radioactive or radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. Radiolabeled compounds of the invention can be used in diagnostic methods such as single-photon emission computed tomography (SPECT). The radioactive isotopes tritium, i.e. $^3$H, and carbon-14, i.e. $^{14}$C, are particularly useful for their ease of incorporation and ready means of detection. Further, compounds may be prepared that are substituted with positron emitting isotopes, such as $^{11}$C, $^{18}$F, $^{15}$O and $^{13}$N, and would be useful in positron emission topography (PET) studies for examining substrate receptor occupancy.

All isotopic variants of the compounds of the invention, radioactive or not, are intended to be encompassed within the scope of the invention. In one aspect, provided herein are deuterated or tritiated analogs of compounds of Formula I.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of π electrons and an atom (usually HI). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

Compounds of the invention may also exist as "rotamers," that is, conformational isomers that occur when the rotation leading to different conformations is hindered, resulting in a rotational energy barrier to be overcome to convert from one conformational isomer to another.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

In some embodiments, the compound can be provided as a prodrug. The term "prodrug", as employed herein, denotes a compound which, upon administration to a subject, undergoes chemical conversion by metabolic or chemical processes to yield a compound of the Formula (I), or a salt and/or solvate thereof.

In some embodiments, the compounds of the invention, and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof.

As used herein, the phrase "optionally substituted" means unsubstituted or substituted. As used herein, the term "substituted" means that a hydrogen atom is removed and replaced by a substituent. It is understood that substitution at a given atom is limited by valency.

The compounds according to the invention have been found to have pharmacologically important properties which can be used therapeutically. The compounds of the invention can be used alone, in combination with each other or in combination with other active compounds. Compounds of Formula (I) may be inhibitors of NMDA (N-methyl-D-aspartate)-receptors, more particularly subtype specific inhibitors of NMDA NR2B receptors. It is therefore a part of the subject-matter of this invention that the compounds of the invention and their salts and also pharmaceutical preparations which comprise these compounds or their salts, can be used for treating or preventing disorders associated with, accompanied by and/or covered by NR2B receptor hyperactivity and/or disorders in which inhibiting NR2B receptors is of value.

In various embodiments, the compounds of the invention are inhibitors of the NR2B receptor with $IC_{50}$ values <10 µM, preferably ≤1 µM and more preferably ≤100 nM.

Exemplary Methods of Treatment

The compounds of the invention including their salts, solvates and hydrates, can be used for the treatment of central nervous system disorders of mammals including a human.

More particularly, the invention relates to the treatment of neurologic and psychiatric disorders including, but not limited to: (1) mood disorders and mood affective disorders; (2) neurotic, stress-related and somatoform disorders including anxiety disorders; (3) disorders of psychological development; (4) behavioral syndromes associated with physiological disturbances and physical factors; (5) extrapyramidal and movement disorders; (6) episodic and paroxysmal disorders, epilepsy; (7) pain; (8) forms of neurodegeneration; (9) cerebrovascular diseases, acute and chronic; and any sequelae of cerebrovascular diseases.

Examples of mood disorders and mood affective disorders that can be treated according to the present invention include, but are not limited to, bipolar disorder I depressed, hypomanic, manic and mixed form; bipolar disorder II; depressive disorders, such as single depressive episode or recurrent major depressive disorder, minor depressive disorder, depressive disorder with postpartum onset, depressive disorders with psychotic symptoms; persistent mood disorders, such as cyclothymia, dysthymia, euthymia; and premenstrual dysphoric disorder.

Examples of disorders belonging to the neurotic, stress-related and somatoform disorders that can be treated according to the present invention include, but are not limited to, anxiety disorders, general anxiety disorder, panic disorder with or without agoraphobia, specific phobia, social phobia, chronic anxiety disorders; obsessive compulsive disorder; reaction to sever stress and adjustment disorders, such as post traumatic stress disorder (PTSD); other neurotic disorders such as depersonalization-derealization syndrome.

Examples of disorders of psychological development that can be treated according to the present invention include, but are not limited to pervasive developmental disorders, including but not limited to Asperger's syndrome and Rett's syndrome, autistic disorders, childhood autism and overactive disorder associated with mental retardation and stereotyped movements, specific developmental disorder of motor function, specific developmental disorders of scholastic skills.

Examples of behavioral syndromes associated with physiological disturbances and physical factors according to the present invention include, but are not limited to mental and behavioural disorders associated with the puerperium, including but not limited to postnatal and postpartum depression; eating disorders, including but not limited to anorexia nervosa and bulimia nervosa.

Examples of extrapyramidal and movement disorders that can be treated according to the present invention include, but are not limited to Parkinson's disease; second Parkinsonism, such as postencephalitic Parkinsonism; Parkinsonism comprised in other disorders; Lewis body disease; degenerative diseases of the basal ganglia; other extrapyramidal and movement disorders including but not limited to tremor, essential tremor and drug-induced tremor, myoclonus, chorea and drug-induced chorea, drug-induced tics and tics of organic origin, drug-induced acute dystonia, drug-induced tardive dyskinesia, L-dopa-induced dyskinesia; neuroleptic-induced movement disorders including but not limited to neuroleptic malignant syndrome (NMS), neuroleptic induced parkinsonism, neuroleptic-induced early onset or acute dyskinesia, neuroleptic-induced acute dystonia, neuroleptic-induced acute akathisia, neuroleptic-induced tardive dyskinesia, neuroleptic-induced tremor; restless leg syndrome, Stiff-man syndrome.

Further examples of movement disorders with malfunction and/or degeneration of basal ganglia that can be treated according to the present invention include, but are not limited to dystonia including but not limited to focal dystonia, multiple-focal or segmental dystonia, torsion dystonia, hemispheric, generalised and tardive dystonia (induced by psychopharmacological drugs). Focal dystonia include cervical dystonia (torticolli), blepharospasm (cramp of the eyelid), appendicular dystonia (cramp in the extremities, like the writer's cramp), oromandibular dystonia and spasmodic dysphonia (cramp of the vocal cord);

Examples for episodic and paroxysmal disorders that can be treated according to the present invention include, but are not limited to epilepsy, including localization-related (focal) (partial) idiopathic epilepsy and epileptic syndromes with seizures of localized onset, localization-related (focal)(partial) symptomatic epilepsy and epileptic syndromes with simple partial seizures, localization-related (focal)(partial) symptomatic epilepsy and epileptic syndromes with complex partial seizures, generalized idiopathic epilepsy and epileptic syndromes including but not limited to myoclonic epilepsy in infancy, neonatal convulsions (familial), childhood absence epilepsy (pyknolepsy), epilepsy with grand mal seizures on awakening, absence epilepsy, myoclonic epilepsy (impulsive petit mal) and nonspecific atonic, clonic, myoclonic, tonic, tonic-clonic epileptic seizures.

Further examples of epilepsy that can be treated according to the present invention include, but are not limited to epilepsy with myoclonic absences, myoclonic-astatic seizures, infantile spasms, Lennox-Gastaut syndrome, Salaam attacks, symptomatic early myoclonic encephalopathy, West's syndrome, petit and grand mal seizures; status epilepticus.

Examples of pain include, but are not limited to pain disorders related to psychological factors, such as persistent somatoform disorders; acute, chronic and chronic intractable pain, headache; acute and chronic pain related to physiological processes and physical disorders including but not limited to back pain, tooth pain, abdominal pain, low back pain, pain in joints; acute and chronic pain that is related to diseases of the musculoskeletal system and connective tissue including, but not limited to rheumatism, myalgia, neuralgia and fibromyalgia; acute and chronic pain that is related to nerve, nerve root and plexus disorders, such as trigeminal pain, postzoster neuralgia, phantom limb syndrome with pain, carpal tunnel syndrome, lesion of sciatic nerve, diabetic mononeuropathy; acute and chronic pain that is related to polyneuropathies and other disorders of the peripheral nervous system, such as hereditary and idiopathic neuropathy, inflammatory polyneuropathy, polyneuropathy induced by drugs, alcohol or toxic agents, polyneuropathy in neoplastic disease, diabetic polyneuropathy.

Examples of diseases that include forms of neurodegeneration include, but are not limited to, acute neurodegeneration, such as intracranial brain injuries, such as stroke, diffuse and local brain injuries, epidural, subdural and subarachnoid haemorrhage, and chronic neurodegeneration, such as Alzheimer's disease, Huntington's disease, and ALS.

Examples of cerebrovascular diseases include, but are not limited to, subarachnoid haemorrhage, intracerebral haemorrhage and other nontraumatic intracranial haemorrhage, cerebral infarction, stroke, occlusion and stenosis or precerebral and cerebral arteries, not resulting in cerebral infarction, dissection of cerebral arteries, cerebral aneurysm, cerebral atherosclerosis, progressive vascular leukoencephalopathy, hypertensive encephalopathy, non-pyogenic thrombosis of intracranial venous system, cerebral arteritis, cerebral amyloid angiopathy and sequelae of cerebrovascular diseases.

In some embodiments, administration of a compound of the invention, or pharmaceutically acceptable salt thereof, is effective in preventing the disease; for example, preventing a disease, condition or disorder in an individual who may be predisposed to the disease, condition or disorder but does not yet experience or display the pathology or symptomatology of the disease.

Exemplary Pharmaceutical Compositions

The present invention further provides pharmaceutical compositions comprising a therapeutically effective amount of a compound of Formula I or pharmaceutically acceptable salt, solvate, or N-oxide thereof, for use in medicine, e.g. in human or veterinary medicine. In some embodiments, the composition further comprises a pharmaceutically acceptable carrier.

An effective dose of the compounds according to the invention, or their salts, solvates or prodrugs thereof is used, in addition to physiologically acceptable carriers, diluents and/or adjuvants for producing a pharmaceutical composition. The dose of the active compounds can vary depending on the route of administration, the age and weight of the patient, the nature and severity of the diseases to be treated, and similar factors. The daily dose can be given as a single dose, which is to be administered once, or be subdivided into two or more daily doses, and is as a rule 0.001-5000 mg. Particular preference is given to administering daily doses of 0.1-3000 mg, e.g. 1-2000 mg.

Suitable administration forms are oral, parenteral, intravenous, transdermal, topical, inhalative, intranasal and sublingual preparations. Particular preference is given to using oral, parenteral, e.g. intravenous or intramuscular, intranasal preparations, e.g. dry powder or sublingual, of the compounds according to the invention. The customary galenic preparation forms, such as tablets, sugar-coated tablets, capsules, dispersible powders, granulates, aqueous solutions, alcohol-containing aqueous solutions, aqueous or oily suspensions, syrups, juices or drops, can be used.

Solid medicinal forms can comprise inert components and carrier substances, such as calcium carbonate, calcium phosphate, sodium phosphate, lactose, starch, mannitol, alginates, gelatine, guar gum, magnesium stearate, aluminium stearate, methyl cellulose, talc, highly dispersed silicic acids, silicone oil, higher molecular weight fatty acids, (such as stearic acid), gelatine, agar agar or vegetable or animal fats and oils, or solid high molecular weight polymers (such as polyethylene glycol); preparations which are suitable for oral administration can comprise additional flavourings and/or sweetening agents, if desired.

Liquid medicinal forms can be sterilized and/or, where appropriate, comprise auxiliary substances, such as preservatives, stabilizers, wetting agents, penetrating agents, emulsifiers, spreading agents, solubilizers, salts, sugars or sugar alcohols for regulating the osmotic pressure or for buffering, and/or viscosity regulators.

Examples of such additives are tartrate and citrate buffers, ethanol and sequestering agents (such as ethylenediaminetetraacetic acid and its non-toxic salts). High molecular weight polymers, such as liquid polyethylene oxides, microcrystalline celluloses, carboxymethyl celluloses, polyvinylpyrrolidones, dextrans or gelatine, are suitable for regulating the viscosity. Examples of solid carrier substances are starch, lactose, mannitol, methyl cellulose, talc, highly dispersed silicic acids, high molecular weight fatty acids (such as stearic acid), gelatine, agar agar, calcium phosphate, magnesium stearate, animal and vegetable fats, and solid high molecular weight polymers, such as polyethylene glycol.

Oily suspensions for parenteral or topical applications can be vegetable, synthetic or semisynthetic oils, such as liquid fatty acid esters having in each case from 8 to 22 C atoms in the fatty acid chains, for example palmitic acid, lauric acid, tridecanoic acid, margaric acid, stearic acid, arachidic acid, myristic acid, behenic acid, pentadecanoic acid, linoleic acid, elaidic acid, brasidic acid, erucic acid or oleic acid, which are esterified with monohydric to trihydric alcohols having from 1 to 6 C atoms, such as methanol, ethanol, propanol, butanol, pentanol or their isomers, glycol or glycerol. Examples of such fatty acid esters are commercially available miglyols, isopropyl myristate, isopropyl palmitate, isopropyl stearate, PEG 6-capric acid, caprylic/capric acid esters of saturated fatty alcohols, polyoxyethylene glycerol trioleates, ethyl oleate, waxy fatty acid esters, such as artificial ducktail gland fat, coconut fatty acid isopropyl ester, oleyl oleate, decyl oleate, ethyl lactate, dibutyl phthalate, diisopropyl adipate, polyol fatty acid esters, inter alia. Silicone oils of differing viscosity, or fatty alcohols, such as isotridecyl alcohol, 2octyldodecanol, cetylstearyl alcohol or oleyl alcohol, or fatty acids, such as oleic acid, are also suitable. It is furthermore possible to use vegetable oils, such as castor oil, almond oil, olive oil, sesame oil, cotton seed oil, groundnut oil or soybean oil.

Suitable solvents, gelatinizing agents and solubilizers are water or water-miscible solvents. Examples of suitable substances are alcohols, such as ethanol or isopropyl alcohol, benzyl alcohol, 2octyldodecanol, polyethylene glycols, phthalates, adipates, propylene glycol, glycerol, di or tripropylene glycol, waxes, methyl cellosolve, cellosolve, esters, morpholines, dioxane, dimethyl sulphoxide, dimethylformamide, tetrahydrofuran, cyclohexanone, etc.

Cellulose ethers which can dissolve or swell both in water or in organic solvents, such as hydroxypropylmethyl cellulose, methyl cellulose or ethyl cellulose, or soluble starches, can be used as film-forming agents.

Mixtures of gelatinizing agents and film-forming agents are also perfectly possible. In this case, use is made, in particular, of ionic macromolecules such as sodium carboxymethyl cellulose, polyacrylic acid, polymethacrylic acid and their salts, sodium amylopectin semiglycolate, alginic acid or propylene glycol alginate as the sodium salt, gum arabic, xanthan gum, guar gum or carrageenan. The following can be used as additional formulation aids: glycerol, paraffin of differing viscosity, triethanolamine, collagen, allantoin and novantisolic acid. Use of surfactants, emulsifiers or wetting agents, for example of Na lauryl sulphate, fatty alcohol ether sulphates, di-Na—N-lauryl-β-iminodipropionate, polyethoxylated castor oil or sorbitan monooleate, sorbitan monostearate, polysorbates (e.g. Tween), cetyl alcohol, lecithin, glycerol monostearate, polyoxyethylene stearate, alkylphenol polyglycol ethers, cetyltrimethylammonium chloride or mono/dialkylpolyglycol ether orthophosphoric acid monoethanolamine salts can also be required for the formulation. Stabilizers, such as montmorillonites or colloidal silicic acids, for stabilizing emulsions or preventing the breakdown of active substances such as antioxidants, for example tocopherols or butylhydroxyanisole, or preservatives, such as phydroxybenzoic acid esters, can likewise be used for preparing the desired formulations.

Preparations for parenteral administration can be present in separate dose unit forms, such as ampoules or vials. Use is preferably made of solutions of the active compound, preferably aqueous solution and, in particular, isotonic solutions and also suspensions. These injection forms can be made available as ready-to-use preparations or only be prepared directly before use, by mixing the active compound, for example the lyophilisate, where appropriate containing other solid carrier substances, with the desired solvent or suspending agent.

Intranasal preparations can be present as aqueous or oily solutions or as aqueous or oily suspensions. They can also be present as lyophilisates which are prepared before use using the suitable solvent or suspending agent.

Inhalable preparations can present as powders, solutions or suspensions. Preferably, inhalable preparations are in the form of powders, e.g. as a mixture of the active ingredient with a suitable formulation aid such as lactose.

The preparations are produced, aliquoted and sealed under the customary antimicrobial and aseptic conditions.

As indicated above, the compounds of the invention may be administered as a combination therapy with further active agents, e.g. therapeutically active compounds useful in the treatment of central nervous system disorders. Exemplary compounds useful in the present invention include, but are not limited to:

tricyclic antidepressants, e.g. Imipramine, Desipramine, Clomipramine, Amitriptyline;

tetracyclic antidepressants, e.g. Mianserin;

serotonin/noradrenaline reuptake inhibitors (SNRI), e.g. Venlafaxine;

selective serotonin reuptake inhibitors (SSRI), e.g. Citalopram, Fluoxetine, Paroxetine;

selective noradrenaline reuptake inhibitors, e.g. Reboxetine;

monoaminoxidase inhibitors, e.g. Tranylcypromine, Moclobemid; and other antidepressants, e.g. Oxitriptan, Agomelatine.

For a combination therapy, the active ingredients may be formulated as compositions containing several active ingredients in a single dose form and/or as kits containing individual active ingredients in separate dose forms. The active ingredients used in combination therapy may be co-administered or administered separately.

While the foregoing specification teaches the principles of the present invention, with examples provided for the purpose of illustration only, it will be understood that the practice of the invention encompasses all of the usual variations, adaptations and/or modifications as come within the scope of the following claims and their equivalents.

EXAMPLES

Chemical names were generated using ChemDraw Ultra 12.0 (CambridgeSoft Corp., Cambridge, Mass.) or ACD/Name Version 10.01 (Advanced Chemistry). A prefix of (R/S*) indicates that the compound(s) is/are single enantiomers; however the stereochemistry shown is arbitrary and the absolute stereochemistry has not been determined.

Abbreviations

Abbreviations and acronyms used herein include the following:

| Acronym | Term |
| --- | --- |
| ACN | Acetonitrile |
| aq | Aqueous |
| Au(III)Cl3 | Gold(III) chloride |
| BOP | Benzotriazol-1-yloxy-tris(dimethylamino)phosphonium hexafluorophosphate |
| br. | Broad |
| Cs2CO3 | Cesium carbonate |
| CsF | Cesium fluoride |
| CuI | Copper(I) iodide |
| DCE | 1,2-dichloroethane |
| DCM | Dichloromethane |
| dd | Doublet of doublet |
| ddd | Doublet of doublet of doublets |
| DIPEA | N,N-diisopropylethylamine |
| DMF | Dimethylformamide |
| DMSO | Dimethyl sulfoxide |
| dt | Doublet of triplets |
| ESI | Electrospray ionizationu |
| Et3N | Triethylamine |
| EtOAc | Ethyl acetate |
| g | Grams |
| HCl | Hydrogen chloride |
| H2O | Water |
| HATU | 1-[Bis(dimethylamino)methylene]-1H-1,2,3-triazolo[4,5-b]pyridinium 3-oxid hexafluorophosphate |
| HBTU | 2-(1H-Benzotriazole-1-yl)-1,1,3,3-tetramethyluronium hexafluorophosphate |

-continued

| Acronym | Term |
|---|---|
| HPLC | High-pressure liquid chromatography |
| Hz | Hertz |
| J | Coupling constant |
| K3PO4 | Tripotassium phosphate |
| LiCl | Lithium chloride |
| LiOH | Lithium hydroxide |
| M | Molar |
| m | Multiplet |
| m/z | Mass to charge ratio |
| MeOH | Methanol |
| mg | Milligrams |
| MgSO4 | Magnesium sulfate |
| MHz | Mega hertz |
| min | Minutes |
| mL | Milliliter |
| mm | Millimeter |
| mmol | Millimoles |
| MS | Mass spectrometry |
| MsCl | Methanesulfonyl chloride |
| MTBE | Methyl tert-butyl ether |
| N | Normal |
| Na2CO3 | Sodium carbonate |
| NaHCO3 | Sodium bicarbonate |
| Na2SO4 | Sodium sulfate |
| NaH | Sodium hydride |
| NBS | N-bromosuccinimide |
| NCS | N-chlorosuccinimide |
| NFBS | N-fluorobenzenesulfonimide |
| NH3 | Ammonia |
| NMR | Nuclear magnetic resonance |
| Pd(dppf)Cl2 | [1,1'-bis(diphenylphosphino)ferrocene]dichloropalladium(II) |
| Pd(dtbpf)2Cl2 | [1,1'-bis(di-tert-butylphosphino)ferrocene]dichloropalladium(II) |
| Pd(PPh3)2Cl2 | Bis(triphenylphosphine)palladium(II) dichloride |
| Pd(PPh3)4 | Tetrakis(triphenylphosphine)palladium(0) |
| PPh3 | Triphenylphosphine |
| ppm | Parts per million |
| q | Quadruplet |
| qt | Quartet of triplets |
| quint | Quintuplet |
| Rt | Retention time |
| rt | Room temperature |
| s | Singulet |
| SEMCl | 2-(Trimethylsilyl)ethoxymethyl chloride |
| t | Triplet |
| T | Temperature |
| td | Triplet of doublets |
| TBAF | Tetrabutylammonium fluoride |
| tBuLi | Teri-butyllithium |
| TFA | Trifluoroacetic acid |
| THF | Tetrahydrofuran |
| μL | Microliter |
| μm | Micrometer |
| x | Times |
| NT | Not Tested |

Chemistry

Example 1: 1-(4-Chloro-phenyl)-4-(3,5-dimethyl-[1,2,4]triazol-1-ylmethyl)-1H-[1,2,3]triazole

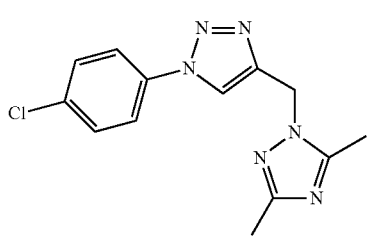 [SMILES: Cc1nc(C)n(Cc2cn(-c3ccc(Cl)cc3)nn2)n1]

Step 1: 1-Azido-4-chorobenzene

Prepared in analogy to J. Org Chem. (1989) 54:5938-5945, which is incorporated by reference herein in its entirety.

To a solution of sulfuric acid (40 mL) and trifluoroacetic acid (200 mL) 4-chloroaniline (29.3 g, 0.23 mol) were added. Then under ice-cooling a solution of sodium nitrite (20.6 g 0.3 mob) in water (200 mL) was added over 30 min at 15-18° C.

The solution was then stirred for 30 min while kept in the ice bath. A solution of sodium azide (25.42 g, 0.39 mol) in water (150 mL) was added dropwise over 30 min. Reaction mixture was stirred without cooling for 1 h, then extracted with diethyl ether.

The combined organic layers were washed with water two times. Then the combined organic layers were diluted with saturated aqueous sodium carbonate solution (500 mL) until the mixture became basic. The organic phase was separated and washed with brine, extracted again with diethyl ether. The organic layers were dried over sodium sulfate and evaporated at 40° C., minimum 50 mbar to afford the title product (34.7 g, 96 percent).

Step 2: [1-(4-Chlorophenyl)triazol-4-yl]methanol

1-Azido-4-chlorobenzene (9.6 g. 61.7 mmol) and propargyl alcohol (4.15 g, 74.0 mmol) were dissolved in ter-butanol (90 mL) and water (90 mL). Copper(II)sulphate pentahydrate (1.54 g, 6.17 mmol) and L-ascorbic acid sodium salt (1.22 g, 6.17 mmol) were added and the mixture was stirred at room temperature. After 2 hours the mixture was poured into water (700 mL) and the formed precipitate was collected by filtration (9.4 g, 70 percent)).

Step 3: 4-Chloromethyl-4-chloro-phenyl)-1H-[1,2,3]triazole

A mixture of 20 ml of thionyl chloride, 20 ml of methylene chloride and 2 g of [1-(4-chlorophenyl)triazol-4-yl] methanol were stirred over night at room temperature. The mixture was then poured into ice/water containing potassium carbonate. The organic layer was separated, dried with potassium carbonate and evaporated. The crude product was purified by flash chromatography to form 1.2 g of the title compound.

Step 4: 1-(4-Chloro-phenyl)-4-(3,5-dimethyl-[1,5,4]triazol-1-ylmethyl)-1H-[1,2,3]triazole A mixture of 1 g of 4-chloromethyl-1-(4-chloro-phenyl)-1H-[1,2,3]triazole, 0.5 g of 3,5-dimethyl-1H-[1,2,4]triazole and 1 g of potassium carbonate in 20 ml of DMF were stirred for 2 days. After filtration and evaporation of the solvent the crude product was purified by flash chromatography to form 0.6 g of the title compound (M+H⁺ 289.7, melting range 153-156° C.).

The examples in Table 1 were prepared as described in Example 1, replacing 3,5-dimethyl-1H-[1,2,4]triazole with the appropriate triazole or imidazole derivative (step 4 in Table 1). The 3- and 5-triazolyl isomers were separated by flash chromatography (methylene chloride with 5% methanol)

TABLE 1

1-[[1-(4-chlorophenyl)-1H-[1,2,3]-triazol-4-yl]methyl] derivatives

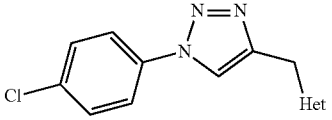

| Ex. | Step 4 | Name-Structure | [M + H]⁺ | m.p. °C. |
|---|---|---|---|---|
| 2 | 5-propyl-1H-[1,2,4]triazole | 1-(4-Chloro-phenyl)-4-(5-propyl-[1,2,4]-triazol-1-ylmethyl)-1H-[1,2,3]triazole | 303.7 | 88-92 |
| 3 | 5-propyl-1H-[1,2,4]triazole | 1-(4-Chloro-phenyl)-4-(3-propyl-[1,2,4]triazol-1-ylmethyl)-1H-[1,2,3]triazole | 303.7 | 114-117 |
| 4 | 5-isopropyl-1H-[1,2,4]triazole | 1-(4-Chloro-phenyl)-4-(3-isopropyl-[1,2,4]triazol-1-ylmethyl)-1H-[1,2,3]triazole | 303.7 | 128-129 |

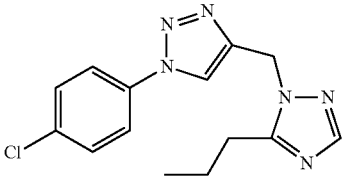 [SMILES: CCCc1ncnn1Cc1cn(-c2ccc(Cl)cc2)nn1]

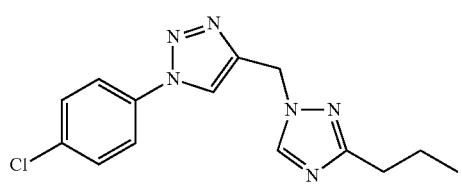 [SMILES: CCCc1ncn(Cc2cn(-c3ccc(Cl)cc3)nn2)n1]

TABLE 1-continued

1-[[1-(4-chlorophenyl)-1H-[1,2,3]-triazol-4-yl]methyl] derivatives

[Structure: 1-(4-chlorophenyl)-1H-[1,2,3]-triazole with CH2-Het at 4-position]

| Ex. | Step 4 | Name-Structure | [M + H]⁺ | m.p. °C. |
|---|---|---|---|---|
| 5 | 5-ethyl-1H-[1,2,4]triazole | 1-(4-Chloro-phenyl)-4-(5-ethyl-[1,2,4]triazol-1-ylmethyl)-1H-[1,2,3]triazole | 289.7 | 148-153 |
| 6 | 5-ethyl-1H-[1,2,4]triazole | 1-(4-Chloro-phenyl)-4-(3-ethyl-[1,2,4]triazole-1-ylmethyl)-1H-[1,2,3]triazole | 289.7 | 123-126 |
| 7 | 5-isopropyl-1H-[1,2,4]triazole | 1-(4-Chloro-phenyl)-4-(5-isopropyl[1,2,4]triazol-1-ylmethyl)-1H-[1,2,3]triazole | 303.7 | 94-98 |
| 8 | 5-methyl-1H-[1,2,4]triazole | 1-(4-Chloro-phenyl)-4-(5-methyl-[1,2,4]triazol-1-ylmethyl)-1H-[1,2,3]triazole | 275.7 | 165-166 |
| 9 | 5-methyl-1H-[1,2,4]triazole | 1-(4-Chloro-phenyl)-4-(3-methyl-[1,2,4]triazol-1-ylmethyl)-1H-[1,2,3]triazole | 275.7 | 161-163 |

TABLE 1-continued

1-[[1-(4-chlorophenyl)-1H-[1,2,3]-triazol-4-yl]methyl] derivatives

| Ex. | Step 4 | Name-Structure | [M + H]+ | m.p. °C. |
|---|---|---|---|---|
| 10 | 3,5-dicyclo propyl-1H-[1,2,4]triazole | 1-(4-Chlorophenyl)-4-(3,5-dicyclopropyl-[1,2,4]triazol-1-ylmethyl)-1-[1,2,3]triazole | 341.8 | 102-105 |
| 11 | 5-cyclobutyl-1H-[1,2,4]triazole | 1-(4-Chloro-phenyl)-4-(5-cyclobutyl-[1,2,4]triazol-1-ylmethyl)-1H-[1,2,3]triazole | 315.8 | 134-138 |
| 12 | 5-cyclobutyl-1H-[1,2,4]triazole | 1-(4-Chloro-phenyl)-4-(3-cyclobutyl-[1,2,4]triazol-1-ylmethyl)-1H-[1,2,3]triazole | 315.8 | 118-122 |
| 13 | 5-cyclopropyl-1H-[1,2,4]triazole | 1-(4-Chloro-phenyl)-4-(3-cyclopropyl-[1,2,4]triazol-1-ylmethyl)-1H-[1,2,3]triazole | 301.7 | 121-126 |
| 14 | 5-cyclopentyl-1H-[1,2,4]triazole | 1-(4-Chloro-phenyl-4-(5-cyclopentyl-[1,2,4]triazol-1-ylmethyl)-1H-[1,2,3]triazole | 329.7 | 143-147 |

TABLE 1-continued

1-[[1-(4-chlorophenyl)-1H-[1,2,3]-triazol-4-yl]methyl] derivatives

| Ex. | Step 4 | Name-Structure | [M + H]⁺ | m.p. °C. |
|---|---|---|---|---|
| 15 | 5-cyclopentyl-1H-[1,2,4] triazole | 1-(4-Chloro-phenyl)-4-(3-cyclopentyl-[1,2,4]triazol-1-ylmethyl)-1H-[1,2,3]triazole | 329.7 | 112-117 |
| 16 | 5-cyclopropyl-1H-[1,2,4] triazole | 1-(4-Chloro-phenyl)-4-(5-cyclopropyl-[1,2,4]triazol-1-ylmethyl)-1H-[1,2,3]triazole | 301.7 | 113-116 |
| 17 | 5-trifluoro methyl-1H-[1,2,4] triazole | 1-(4-Chloro-phenyl)-4-(3-triflouromethyl-[1,2,4]triazol-1-ylmethyl)-1H-[1,2,3]triazole | 329.7 | 127-130 |
| 18 | 2-propyl-1H-imidazole | 1-(4-Chloro-phenyl)-4-(2-propyl-imidazol-1-ylmethyl)-1H-[1,2,3]triazole | 302.7 | 116-121 |
| 19 | 5-tert-butyl-1H-[1,2,4] triazole | 4-(5-tert-Butyl-[1,2,4]triazol-1-ylmethyl)-1-(4-chloro-phenyl)-1H-[1,2,3]triazole | 317.7 | 134-139 |

TABLE 1-continued

1-[[1-(4-chlorophenyl)-1H-[1,2,3]-triazol-4-yl]methyl] derivatives

| Ex. | Step 4 | Name-Structure | [M + H]⁺ | m.p. °C. |
|---|---|---|---|---|
| 20 | 5-tert-butyl-1H-[1,2,4]triazole | 4-(3-tert-Butyl-[1,2,4]triazol-1-ylmethyl)-1-(4-chloro-phenyl)-1H-[1,2,3]triazole | 317.7 | 125-129 |
| 21 | 5-cyclobutyl-3-methyl-1H-[1,2,4]triazole | 1-(4-Chloro-phenyl)-4-(5-cyclobutyl-3-methyl-[1,2,4]triazole-1-ylmethyl)-1H-[1,2,3]triazole | 329.8 | 133-137 |
| 22 | 5-cyclobutyl-3-methyl-1H-[1,2,4]triazole | 1-(4-Chloro-phenyl)-4-(3-cyclobutyl-5-methyl-[1,2,4]triazol-1-ylmethyl)-1H-[1,2,3]triazole | 329.8 | 140-145 |
| 23 | 2-isopropyl-1H-imidazole | 1-(4-Chloro-phenyl)-4-(2-isopropyl-imidazol-1-ylmethyl)-1H-[1,2,3]triazole | 302.8 | 124-128 |
| 24 | 2-methyl-1H-imidazole | 1-(4-Chloro-phenyl)-4-(2-methyl-imidazol-1-ylmethyl)-1H-[1,2,3]triazole | 274.7 | 153-156 |

TABLE 1-continued

1-[[1-(4-chlorophenyl)-1H-[1,2,3]-triazol-4-yl]methyl] derivatives

| Ex. | Step 4 | Name-Structure | [M + H]⁺ | m.p. °C. |
|---|---|---|---|---|
| 25 | 2-ethyl-1H-imidazole | 1-(4-Chloro-phenyl)-4-(2-ethyl-imidazol-ylmethyl)-1H-[1,2,3]triazole | 288.7 | 178-182 |
| 26 | 2-chloro-1H-imidazole | 4-(2-Chloro-imidazol-1-ylmethyl)-1-(4-chloro-phenyl)-1H-[1,2,3]triazole | 295.1 | 142-145 |
| 27 | 2-butyl-1H-imidazole | 4-(2-Butyl-imidazol-1-ylmethyl)-1-(4-chloro-phenyl)-1H-[1,2,3]triazole | 316.8 | 119-123 |
| 28 | 2-hydroxy-methyl-1H-imidazole | 4-(2-Hydroxymethyl-imidazol-1-ylmethyl)-1-(4-chloro-phenyl)-1H-[1,2,3]triazole | 290.7 | 175-179 |
| 29 | 2-cyclopropyl-1H-imidazole | 1-(4-Chloro-phenyl)-4-(2-cyclopropyl-imidazol-1-ylmethyl)-1H-[1,2,3]triazole | 300.7 | 157-160 |

TABLE 1-continued

1-[[1-(4-chlorophenyl)-1H-[1,2,3]-triazol-4-yl]methyl] derivatives

| Ex. | Step 4 | Name-Structure | [M + H]⁺ | m.p. °C. |
|---|---|---|---|---|
| 31 | 2-tert-butyl-1H-imidazole | 4-(2-tert-Butyl-imidazol-1-ylmethyl)-1-(4-chloro-phenyl)-1H-[1,2,3]triazole | 316.8 | 130-133 |
| 31 | 2-methyl-1H-imidazole | 1-(4-Chloro-phenyl)-4-(3-methyl-[1,2,4]triazol-4-ylmethyl)-1H-[1,2,3]triazole | 274.7 | 175-179 |

The examples in Table 2 were prepared as described in example 1 replacing 4-chloroaniline with 3,4-dichloroaniline (step 1) and 3,5-dimethyl-1H-[1,2,4]triazole with the appropriate triazole or imidazole derivative (step 4). The 3- and 5-triazolyl isomers were separated by flash chromatography (methylene chloride with 5% methanol)

TABLE 2

[1-(3,4-Dichloro-phenyl)-1H-[1,2,3]triazol-4-yl]-methyl]derivatives

| Ex. | Step 4 | Name-Structure | [M + H]⁺ | m.p. ° C. |
|---|---|---|---|---|
| 32 | 2-methyl-1H-imidazole | 1-(3,4-Dichloro-phenyl)-4-(2-methyl-imidazol-1-ylmethyl)-1H-[1,2,3]triazole | 309.1 | 146-150 |
| 33 | 2-ethyl-1H-imidazole | 1-(3,4-Dichloro-phenyl)-4-(2-ethyl-imidazol-1-ylmethyl)-1H-[1,2,3]triazole | 322.1 | 161-164 |

TABLE 2-continued

[1-(3,4-Dichloro-phenyl)-1H-[1,2,3]triazol-4-yl]-methyl]derivatives

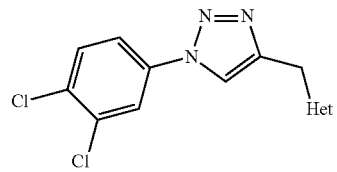

| Ex. | Step 4 | Name-Structure | [M + H]⁺ | m.p. ° C. |
|---|---|---|---|---|
| 34 | 2-propyl-1H-imidazole | 1-(3,4-Dichloro-phenyl)-4-(2-propyl-imidazol-1-ylmethyl)-1H-[1,2,3]triazole | 337.2 | 169-173 |
| 35 | 2-isopropyl-1H-imidazole | 1-(3,4-Dichloro-phenyl)-4-(2-isopropyl-imidazol-1-ylmethyl)-1H-[1,2,3]triazole | 337.2 | 144-147 |
| 36 | 2-cyclopropyl-1H-imidazole | 4-(2-Cyclopropyl-imidazol-1-ylmethyl)-1-(3,4-dichloro-phenyl)-1H-[1,2,3]triazole | 335.2 | 168-170 |
| 37 | 2-butyl-1H-imidazole | 4-(2-Butyl-imidazol-1-ylmethyl)-1-(3,4-dichloro-phenyl)-1H-[1,2,3]triazole | 351.2 | 152-155 |

TABLE 2-continued

[1-(3,4-Dichloro-phenyl)-1H-[1,2,3]triazol-4-yl]-methyl]derivatives

| Ex. | Step 4 | Name-Structure | [M + H]⁺ | m.p. ° C. |
|---|---|---|---|---|
| 38 | 2-tert-butyl-1H-imidazole | 4-(2-tert-Butyl-imidazol-1-ylmethyl)-1-(3,4-dichloro-phenyl)-1H-[1,2,3]triazole | 351.2 | 221-222 |
| 39 | 2-cyclobutyl-1H-imidazole | 4-(2-Cyclobutyl-imidazol-1-ylmethyl)-1-(3,4-dichloro-phenyl)-1H-[1,2,3]triazole | 349.2 | 178-180 |
| 40 | 2-hydroxy-ethyl-1H-imidazole | 4-[2-(2-Hydroxyethyl)-imidazol-1-ylmethyl]-1-(3,4-dichloro-phenyl)-1H-[1,2,3]triazole | 339.2 | 181-186 |
| 41 | 2-fluoro-ethyl-1H-imidazole | 1-(3,4-Dichloro-phenyl)-4-[2-(2-fluoro-ethyl)-imidazol-1-ylmethyl]-1H-[1,2,3]triazole | 341.2 | 146 |

The examples in Table 3 were prepared as described in example 1 replacing 4-chloroaniline with appropriate aniline derivative (step 1) and replacing 3,5-dimethyl-1H-[1,2,4] triazole with the appropriate triazole or imidazole derivative (step 4). The 3- and 5-triazolyl isomers were separated by flash chromatography (methylene chloride with 5% methanol)

TABLE 3

1-[[(subst. phenyl)-1H-[1,2,3]triazol-4-yl]methyl]derivatives

| Ex. | R¹ | R² | Step 4 | Name-Structure | [M + H]⁺ | m.p. ° C. |
|---|---|---|---|---|---|---|
| 42 | 3-Cl | 4-F | 2-ethyl-1H-imidazole | 1-(3-Chloro-4-fluoro-phenyl)-4-(2-ethyl-imidazol-1-ylmethyl)-1H-[1,2,3]triazole | 306.7 | 172-175 |
| 43 | 3-Cl | 4-F | 2-propyl-1H-imidazole | 1-(3-Chloro-4-fluoro-phenyl)-4-(2-propyl-imidazol-1-ylmethyl)-1H-[1,2,3]triazole | 320.7 | 162-166 |
| 44 | 4-Cl | 3-F | 2-cyclo propyl-1H-imidazoe | 1-(3-Chloro-4-fluoro-phenyl)-4-(2-cyclopropyl-imidazol-1-ylmethyl)-1H-[1,2,3]triazole | 318.7 | 177-179 |
| 45 | 3-Cl | 4-F | 2-butyl-1H-imidazole | 4-(2-Butyl-imidazol-1-ylmethyl)-1-(3-chloro-4-fluoro-phenyl)-1H-[1,2,3]triazole | 334.7 | 128-132 |
| 46 | H | H | 3,5-dimethyl-1H-[1,2,4]triazole | 4-(3,5-Dimethyl-[1,2,4]triazol-1-ylmethyl)-1-phenyl-1H-[1,2,3]triazole | 255.3 | 100-101 |

TABLE 3-continued

1-[[(subst. phenyl)-1H-[1,2,3]triazol-4-yl]methyl]derivatives

| Ex. | R¹ | R² | Step 4 | Name-Structure | [M + H]⁺ | m.p. ° C. |
|---|---|---|---|---|---|---|
| 47 | H | H | 3-methyl-5-hydroxy methyl-1H-[1,2,4]triazole | 4-(5-Hydroxymethyl-3-methyl-[1,2,4]triazol-1-ylmethyl)-1-phenyl-1H-[1,2,3]triazole 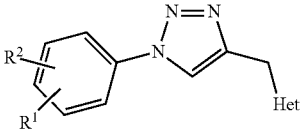 | 271.3 | 166-168 |
| 48 | H | H | 5-methyl-3-hydroxy methyl-1H-[1,2,4]triazole | 4-(3-Hydroxymethyl-5-methyl-[1,2,4]triazol-1-ylmethyl)-1-phenyl-1H-[1,2,3]triazole 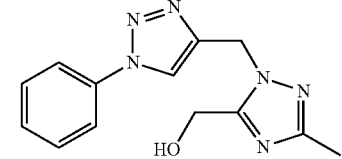 | 271.3 | 154-158 |
| 49 | 2-Cl | 4-Cl | 2-methyl-1H-imidazole | 1-(2,4-Dichloro-phenyl)-4-(2-methyl-imidazol-1-ylmethyl)-1H-[1,2,3]triazole 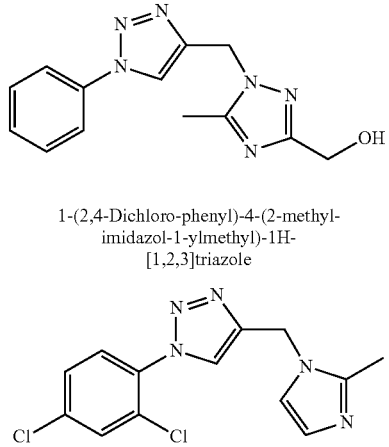 | 309.2 | 103-105 |
| 50 | 4-Cl | 3-F | 2-methyl-1H-imidazole | 1-(4-Chloro-3-fluoro-phenyl)-4-(2-methyl-imidazol-1-ylmethyl)-1H-[1,2,3]triazole 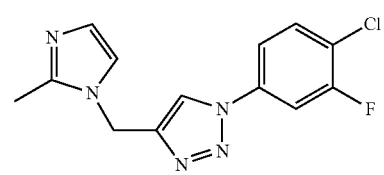 | 292.7 | 141-143 |
| 51 | 3-Cl | 4-F | 2-methyl-1H-imidazole | 1-(3-Chloro-4-fluoro-phenyl)-4-(2-methyl-imidazol-1-ylmethyl)-1H-[1,2,3]triazole 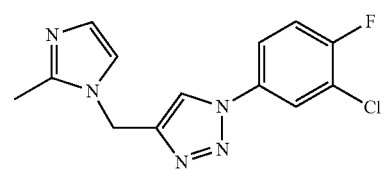 | 292.7 | 130-133 |

TABLE 3-continued

1-[[(subst. phenyl)-1H-[1,2,3]triazol-4-yl]methyl]derivatives

| Ex. | R$^1$ | R$^2$ | Step 4 | Name-Structure | [M + H]$^+$ | m.p. ° C. |
|---|---|---|---|---|---|---|
| 52 | 4-F | 2-OMe | 2-methyl-1H-imidazole | 1-(4-Fluoro-2-methoxy-phenyl)-4-(2-methyl-imidazol-1-ylmethyl)-1H-[1,2,3]triazole | 288.3 | 115 |
| 53 | 3-F | 4-Me | 2-methyl-1H-imidazole | 1-(3-Fluoro-4-methyl-phenyl)-4-(2-methyl-imidazol-1-ylmethyl)-1H-[1,2,3]triazole | 272.3 | 105-106 |
| 54 | 4-F | 3-Me | 2-methyl-1H-imidazole | 1-(4-Fluoro-3-methyl-phenyl)-4-(2-methyl-imidazol-1-ylmethyl)-1H-[1,2,3]triazole | 272.3 | 121-122 |
| 55 | 4-Cl | 3-Me | 2-methyl-1H-imidazole | 1-(4-Chloro-3-methyl-phenyl)-4-(2-methyl-imidazol-1-ylmethyl)-1H-[1,2,3]triazole | 288.7 | 116-117 |
| 56 | 4-Cl | 3-CF$_3$ | 2-methyl-1H-imidazole | 1-(4-Chloro-3-trifluoromethyl-phenyl)-4-(2-methyl-imidazol-1-ylmethyl)-1H-[1,2,3]triazole | 342.7 | 149 |

TABLE 3-continued

1-[[(subst. phenyl)-1H-[1,2,3]triazol-4-yl]methyl]derivatives

| Ex. | R¹ | R² | Step 4 | Name-Structure | [M + H]⁺ | m.p. ° C. |
|---|---|---|---|---|---|---|
| 57 | 3-OCF₃ | H | 2-methyl-1H-imidazole | 4-(2-Methyl-imidazol-1-ylmethyl)-1-(3-trifluoromethoxy-phenyl)-1H-[1,2,3]triazole | 324.3 | 98-100 |
| 58 | 3-CF₃ | H | 2-methyl-1H-imidazole | 4-(2-Methyl-imidazol-1-ylmethyl)-1-(3-trifluoromethyl-phenyl)-1H-[1,2,3]triazole | 308.3 | 110-112 |
| 59 | 4-CF₃ | H | 2-methyl-1H-imidazole | 4-(2-Methyl-imidazol-1-ylmethyl)-1-(4-trifluoromethyl-phenyl)-1H-[1,2,3]triazole | 308.3 | 168 |
| 60 | 2-Cl | 4-Cl | 2-cyclopropyl-1H-imidazole | 4-(2-Cyclopropyl-imidazol-1-ylmethyl)-1-(2,4-dichloro-phenyl)-1H-[1,2,3]triazole hydrochloride | 335.3 | 229-233 |

TABLE 3-continued

1-[[(subst. phenyl)-1H-[1,2,3]triazol-4-yl]methyl]derivatives

| Ex. | R¹ | R² | Step 4 | Name-Structure | [M + H]⁺ | m.p. ° C. |
|---|---|---|---|---|---|---|
| 61 | 4-Cl | 3-F | 2-cyclopropyl-1H-imidazole | 1-(4-Chloro-3-fluoro-phenyl)-4-(2-cyclopropyl-imidazol-1-ylmethyl)-1H-[1,2,3]triazole | 318.7 | 151 |
| 62 | 4-F | 2-OMe | 2-cyclopropyl-1H-imidazole | 4-(2-Cyclopropyl-imidazol-1-ylmethyl)-1-(4-fluoro-2-methoxy-phenyl)-1H-[1,2,3]triazole | 314.3 | 111-113 |
| 63 | 3-F | 4-Me | 2-cyclopropyl-1H-imidazole | 4-(2-Cyclopropyl-imidazol-1-ylmethyl)-1-(3-fluoro-4-methyl-phenyl)-1H-[1,2,3]triazole | 298.3 | 117-118 |
| 64 | 4-F | 3-Me | 2-cyclopropyl-1H-imidazole | 4-(2-Cyclopropyl-imidazol-1-ylmethyl)-1-(4-fluoro-3-methyl-phenyl)-1H-[1,2,3]triazole | 298.3 | 134 |
| 65 | 4-Cl | 3-Me | 2-cyclopropyl-1H-imidazole | 1-(4-Chloro-3-methyl-phenyl)-4-(2-cyclopropyl-imidazol-1-ylmethyl)-1H-[1,2,3]triazole | 314.7 | 125-128 |

TABLE 3-continued

1-[[(subst. phenyl)-1H-[1,2,3]triazol-4-yl]methyl]derivatives

| Ex. | R¹ | R² | Step 4 | Name-Structure | [M + H]⁺ | m.p. ° C. |
|---|---|---|---|---|---|---|
| 66 | 4-Cl | 3-CF₃ | 2-cyclopropyl-1H-imidazole | 1-(4-Chloro-3-trifluoromethyl-phenyl)-4-(2-cyclopropyl-imidazol-1-ylmethyl)-1H-[1,2,3]triazole | 368.7 | 173-174 |
| 67 | 3-OCF₃ | H | 2-cyclopropyl-1H-imidazole | 4-(2-Cyclopropyl-imidazol-1-ylmethyl)-1-(3-trifluoromethoxy-phenyl)-1H-[1,2,3]triazole | 350.3 | 109-111 |
| 68 | 3-CF₃ | H | 2-cyclopropyl-1H-imidazole | 4-(2-Cyclopropyl-imidazol-1-ylmethyl)-1-(3-trifluoromethyl-phenyl)-1H-[1,2,3]triazole | 334.3 | 129-132 |
| 69 | 4-CF₃ | H | 2-cyclopropyl-1H-imidazole | 4-(2-Cyclopropyl-imidazol-1-ylmethyl)-1-(4-trifluoromethyl-phenyl)-1H-[1,2,3]triazole | 334.3 | 161-164 |

TABLE 3-continued

1-[[(subst. phenyl)-1H-[1,2,3]triazol-4-yl]methyl]derivatives

| Ex. | R[1] | R[2] | Step 4 | Name-Structure | [M + H]+ | m.p. ° C. |
|---|---|---|---|---|---|---|
| 70 | 4-Cl | 3-Me | 2-ethyl-1H-imidazole | 1-(4-Chloro-3-methyl-phenyl)-4-(2-ethyl-imidazol-1-ylmethyl)-1H-[1,2,3]triazole | 302.7 | 129-130 |
| 71 | 4-Cl | 3-Me | 2-isopropyl-1H-imidazole | 1-(4-Chloro-3-methyl-phenyl)-4-(2-isopropyl-imidazol-1-ylmethyl)-1H-[1,2,3]triazole | 316.8 | 108-109 |
| 72 | 3-OCF$_3$ | H | 2-ethyl-1H-imidazole | 4-(2-Ethyl-imidazol-1-ylmethyl)-1-(3-trifluoromethoxy-phenyl)-1H-[1,2,3]triazole | 338.3 | 103 |
| 73 | 3-OCF$_3$ | H | 2-isopropyl-1H-imidazole | 4-(2-Isopropyl-imidazol-1-ylmethyl)-1-(3-trifluoromethoxy-phenyl)-1H-[1,2,3]triazole | 352.3 | 91 |
| 74 | 4-Cl | 3-Me | 2-hydroxyethyl-1H-imidazole | 1-(4-Chloro-3-methyl-phenyl)-4-[2-(2-hydroxy-ethyl)-imidazol-1-ylmethyl]-1H-[1,2,3]triazole | 318.7 | 161-162 |

TABLE 3-continued

1-[[(subst. phenyl)-1H-[1,2,3]triazol-4-yl]methyl]derivatives

| Ex. | R¹ | R² | Step 4 | Name-Structure | [M + H]⁺ | m.p. ° C. |
|---|---|---|---|---|---|---|
| 75 | 4-Cl | 3-Me | 2-fluoro ethyl-1H-imidazole | 1-(4-Chloro-3-methyl-phenyl)-4-[2-(2-fluoro-ethyl)-imidazol-1-ylmethyl]-1H-[1,2,3]triazole | 320.7 | 118-123 |
| 76 | 3-Cyclopropyl | H | 2-methyl-1H-imidazole | 1-(3-Cyclopropyl-phenyl)-4-(2-methyl-imidazol-1-ylmethyl)-1H-[1,2,3]triazole | 280.3 | 110-111 |
| 77 | 3-SO₂Me | H | 2-methyl-1H-imidazole | 1-(3-Methanesulfonyl-phenyl)-4-(2-methyl-imidazol-1-ylmethyl)-1H-[1,2,3]triazole | 318.3 | 213-214 |
| 78 | 3-Cyclopropyl | H | 2-hydroxy ethyl-1H-imidazole | 1-(3-Cyclopropyl-phenyl)-4-[2-(2-hydroxy-ethyl)-imidazol-1-ylmethyl]-1H-[1,2,3]triazole | 210.3 | 105 |

TABLE 3-continued

1-[[(subst. phenyl)-1H-[1,2,3]triazol-4-yl]methyl]derivatives

| Ex. | R¹ | R² | Step 4 | Name-Structure | [M + H]⁺ | m.p. ° C. |
|---|---|---|---|---|---|---|
| 79 | 3-SO$_2$Me | H | 2-hydroxy ethyl-1H-imidazole | 4-[2-(2-Hydroxy-ethyl)-imidazol-1-ylmethyl]-1-(3-methanesulfonyl-phenyl)-1H-[1,2,3]triazole | 348.3 | 157-160 |
| 80 | 3-SO$_2$Me | H | 2-fluoro ethyl-1H-imidazole | 4-[2-(2-Fluoro-ethyl)-imidazol-1-ylmethyl]-1-(3-methanesulfonyl-phenyl)-1H-[1,2,3]triazole | 350.3 | 176-177 |

Example 81: 1-(3-Difluoromethyl-4-fluoro-1-phenyl)-4-(2-methyl-imidazol-1-ylmethyl)-1H-[1,2,3]triazole

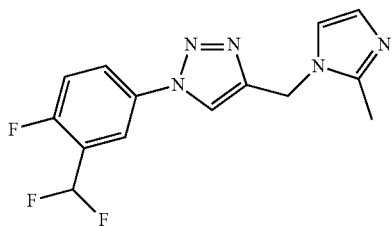 [SMILES: Cc1nccn1Cc1cn(-c2ccc(F)c(C(F)F)c2)nn1]

Step 1: 3-Difluoromethyl-4-fluoro-1-nitrobenzene

A solution of 2-fluoro-5-nitrobenzaldehyde (3.0 g, 17 mmol) in DCM (50 mL) was added DAST (3.42 g, 21 mmol) and stirred at RT for 18 h under nitrogen atmosphere. The reaction mass was quenched in ice-water and extracted with DCM. The organic layer was dried and concentrated to afford 2.5 g of desired product.

Step 2: 3-Difluoromethyl-4-fluoro-aniline

A solution of 2-(difluoromethyl)-1-fluoro-4-nitrobenzene (1.2 g, 6.2 mmol) in methanol (20 mL) was added iron powder (4.8 g, 24.8 mmol) followed by conc. HCl (5 mL) drop-wise. The reaction mass was stirred at RT for 1-2 h. The reaction mass was quenched in ice-water, basified with NaHCO$_3$ and extracted with DCM. The organic layer was dried and concentrated to afford 0.8 g of desired product.

Step 3: 1-Azido-3-difluoromethyl-4-fluoro benzene

To a solution of sulfuric acid (4 mL) and trifluoroacetic acid (20 mL) 3-difluoromethyl-4-fluoro-aniline (3.7 g, 0.023 mol: step 2) were added. Then under ice-cooling a solution of sodium nitrite (2.06 g 0.03 mol) in water (20 mL) was added over 30 main at 15° C.

The solution was then stirred for 30 min while kept in the ice bath. A solution of sodium azide (2.54 g, 0.039 mol) in water (20 mL) was added dropwise over 20 min, Reaction mixture was stirred without cooling for 2 h, then extracted with diethyl ether.

The combined organic layers were washed with water two times. Then the combined organic layers were diluted with saturated aqueous sodium carbonate solution (100 mL) until the mixture became basic. The organic phase was separated and washed with brine, extracted again with diethyl ether.

The organic layers were dried over sodium sulfate and evaporated at 40° C., minimum 50 mbar to afford the title product.

Step 4: [1-(3-Difluoromethyl-4-fluoro)-1H-[1,2,3]triazol-4-yl]methanol

1-Azido-3-difluoromethyl-4-fluoro benzene (11.5 g, 61.7 mmol; step 3) and propargyl alcohol (4.15 g, 74.0 mmol) were dissolved in tert-butanol (90 mL) and water (90 mL). Copper(II)sulphate pentahydrate (1.54 g, 6.17 mmol) and L-ascorbic acid sodium salt (1.22 g, 6.17 mmol) were added and the mixture was stirred at room temperature. After 2 hours the mixture was poured into water (700 mL) and the formed precipitate was collected by filtration.

Step 5: 4-Chloromethyl-1-(3-difluoromethyl-4-fluoro-phenyl)-1H-[1,2,3]triazole A mixture of 20 ml of thionyl chloride, 20 ml of methylene chloride and 2 g of [1-(3-difluoromethyl-4-fluoro)-1-[1,2,3]-triazol-4-yl]methanol (step 4) were stirred over night at room temperature. The mixture was then poured into ice/water containing potassium carbonate. The organic layer was separated, dried with potassium carbonate and evaporated. The crude product was purified by flash chromatography to form 1.1 g of the title compound.

Step 6: 1-[3-(difluoromethyl)-4-fluoro-phenyl]-4-[(2-methylimidazol-1-yl)methyl]-1H-[1,2,3]triazole A mixture of 1 g of 4-chloromethyl-1-(3-difluoromethyl-4-fluoro-phenyl)-1H-[1,2,3]triazole 0.5 g of 3,5-dimethyl-1H-[1,2,4]triazole and 1 g of potassium carbonate in 20 ml of DMF were stirred for 2 days. After filtration and evaporation of the solvent the crude product was purified by flash chromatography to form 0.5 g of the title compound (M+H$^+$ 308.3, melting range 122-123° C.).

The examples in Table 4 were prepared as described in example 81 replacing 2-methyl-imidazole with the appropriate imidazole derivative (step 6).

TABLE 4

[1-(3-Difluoromethyl-4-fluoro-phenyl)-1H-[1,2,3]triazol-4-yl]-methyl derivatives

| Ex. | Step 6 | Name-Structure | [M + H]$^+$ | m.p. ° C. |
|---|---|---|---|---|
| 82 | 2-cyclopropyl-1H-imidazole | 4-(2-Cyclopropyl-imidazol-1-ylmethyl)-1-(3-difluoromethyl-4-fluoro-phenyl)-1H-[1,2,3]triazole 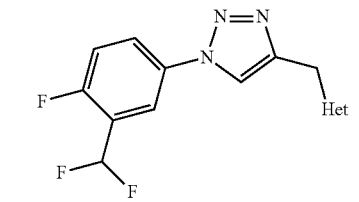 | 334.3 | 155-158 |
| 83 | 2-ethyl-1H-imidazole | 1-(3-Difluoromethyl-4-fluoro-phenyl)-4-(2-ethyl-imidazol-1-ylmethyl)-1H-[1,2,3]triazole 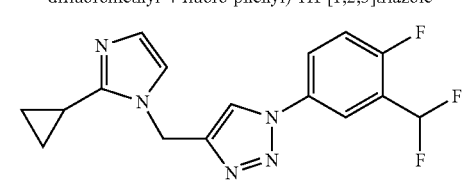 | 322.3 | 165-167 |
| 84 | 2-isopropyl-1H-imidazole | 1-(3-Difluoromethyl-4-fluoro-phenyl)-4-(2-isopropyl-imidazol-1-ylmethyl)-1H-[1,2,3]triazole 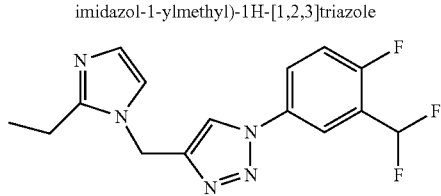 | 336.3 | 113-115 |

TABLE 4-continued

[1-(3-Difluoromethyl-4-fluoro-phenyl)-1H-[1,2,3]triazol-4-yl]-methyl derivatives

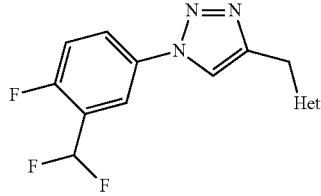

| Ex. | Step 6 | Name-Structure | [M + H]$^+$ | m.p. ° C. |
|---|---|---|---|---|
| 85 | 2-propyl-1H-imidazole | 1-(3-Difluoromethyl-4-fluoro-phenyl)-4-(2-propyl-imidazol-1-ylmethyl)-1H-[1,2,3]triazole | 336.3 | 131-133 |
| 86 | 2-butyl-1H-imidazole | 1-(3-Difluoromethyl-4-fluoro-phenyl)-4-(2-butyl-imidazol-1-ylmethyl)-1H-[1,2,3]triazole | 350.3 | 106-107 |
| 87 | 2-tert. butyl-1H-imidazole | 1-(3-Difluoromethyl-4-fluoro-phenyl)-4-(2-tert.butyl-imidazol-1-ylmethyl)-1H-[1,2,3]triazole | 350.3 | 140-146 |
| 88 | 2-(1H-Imidazol-2-yl)-ethanol | 1-(3-Difluoromethyl-4-fluoro-phenyl)-4-[2-(2-hydroxy-ethyl)-imidazol-1-ylmethyl]-1H-[1,2,3]triazole | 338.3 | 126-128 |

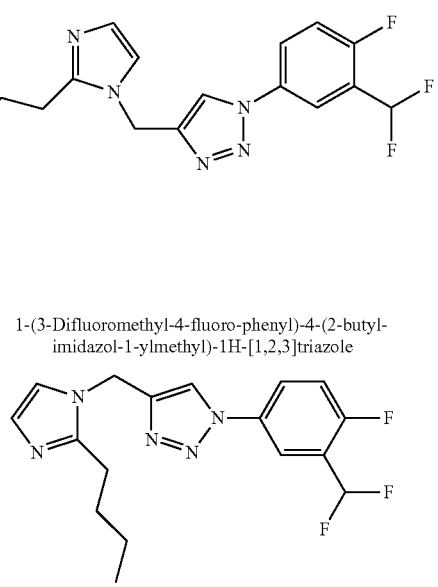

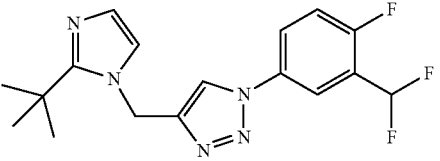

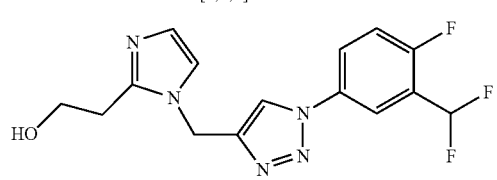

The examples in Table 5 were prepared as described in example 81 replacing 2-fluoro-5-nitrobenzaldehyde with 2-chloro-5-nitrobenzaldehyde (step 1) aid 2-methyl-imidazole with the appropriate imidazole derivative (step 6).

TABLE 5

[1-(4-Chloro-3-difluoromethyl-phenyl)-1H-[1,2,3]triazol-4-yl]-methyl derivatives

| Ex. | Step 6 | Name-Structure | [M + H]⁺ | m.p. ° C. |
|---|---|---|---|---|
| 89 | 2-methyl-1H-imidazole | 1-(4-Chloro-3-difluoromethyl-phenyl)-4-(2-methyl-imidazol-1-ylmethyl)-1H-[1,2,3]triazole | 324.7 | 114-115 |
| 90 | 2-cyclopropyl-1H-imidazole | 1-(4-Chloro-3-difluoromethyl-phenyl)-4-(2-cyclopropyl-imidazol-1-ylmethyl)-1H-[1,2,3]triazole | 350.7 | 138-140 |
| 91 | 2-ethyl-1H-imidazole | 1-(4-Chloro-3-difluoromethyl-phenyl)-4-(2-ethyl-imidazol-1-ylmethyl)-1H-[1,2,3]triazole | 338.7 | 144-145 |
| 92 | 2-isopropyl-1H-imidazole | 1-(4-Chloro-3-difluoromethyl-phenyl)-4-(2-isopropyl-imidazol-1-ylmethyl)-1H-[1,2,3]triazole | 352.8 | 129-131 |

The examples in Table 6 were prepared as described in example 1 replacing 4-chloroaniline with 4-chloro-3-difluoromethoxy-aniline (step 1) and 3,5-dimethyl-1H-[1,2,4]triazole with the appropriate imidazole derivative (step 4).

TABLE 6

[1-(4-Chloro-3-difluoromethoxy-phenyl)-1H-[1,2,3]triazol-4-yl]-methyl derivatives

| Ex. | Step 4 | Name-Structure | [M + H]⁺ | m.p. ° C. |
|---|---|---|---|---|
| 93 | 2-methyl-1H-imidazole | 1-(4-Chloro-3-difluoromethoxy-phenyl)-4-(2-methyl-imidazol-1-ylmethyl)-1H-[1,2,3]triazole | 340.7 | 167-168 |
| 94 | 2-cyclopropyl-1H-imidazole | 1-(4-Chloro-3-difluoromethoxy-phenyl)-4-(2-cyclopropyl-imidazol-1-ylmethyl)-1H-[1,2,3]triazole | 366.7 | 142-146 |
| 95 | 2-tert. butyl-1H-imidazole | 4-(2-tert-Butyl-imidazol-1-ylmethyl)-1-(4-chloro-3-difluoromethoxy-phenyl)-1H-[1,2,3]triazole | 382.8 | 159-162 |
| 96 | 2-ethyl-1H-imidazole | 1-(4-Chloro-3-difluoromethoxy-phenyl)-4-(2-ethyl-imidazol-1-ylmethyl)-1H-[1,2,3]triazole | 354.7 | 153-155 |
| 97 | 2-isopropyl-1H-imidazole | 1-(4-Chloro-3-difluoromethoxy-phenyl)-4-(2-isopropyl-imidazol-1-ylmethyl)-1H-[1,2,3]triazole | 368.7 | 99-101 |

TABLE 6-continued

[1-(4-Chloro-3-difluoromethoxy-phenyl)-1H-[1,2,3]triazol-4-yl]-methyl derivatives

| Ex. | Step 4 | Name-Structure | [M + H]+ | m.p. ° C. |
|---|---|---|---|---|
| 98 | 2-(1H-imidazol-2-yl)-ethanol | 1-(4-Chloro-3-difluoromethoxy-phenyl)-4-[2-(2-hydroxy-ethyl)-imidazol-1-ylmethyl]-1H-[1,2,3]triazole | 370.7 | 156 |
| 99 | 2-(2-Fluoro-ethyl)-1H-imidazole | 1-(4-Chloro-3-difluoromethoxy-phenyl)-4-[2-(2-fluoro-ethyl)-imidazol-1-ylmethyl]-1H-[1,2,3]triazole | 372.7 | 135-136 |

Example 100: 1-(3-Difluoromethoxy-4-fluoro-phenyl)-4-(2-methyl-imidazol-1-ylmethyl)-1H-[1,2,3]triazole

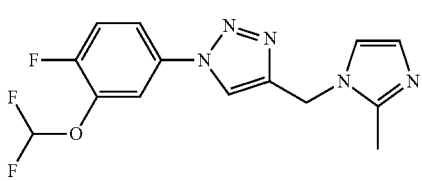 [SMILES: Cc1nccn1Cc1cn(-c2ccc(F)c(OC(F)F)c2)nn1]

Step 1: 2-Difluoromethoxy-1-fluoro-4-nitro-benzene

A mixture of 2-fluoro-5-nitro-phenol (4.3 g; 27.38 mmol), K₂CO₃ (4.541 g; 32.85 mmol), sodium chlorodifluoroacetate (8.348 g; 51.76 mmol) in DMF (90 ml), and water (2 ml) was degassed by bubbling nitrogen into the suspension for 5 min., and was then heated to 100° C., under nitrogen, for 2.5 h.

The heterogeneous mixture was allowed to cool to room temperature, and 12N HCl (8 ml; 96 mmol), and water (12 ml) were successively added, and this mixture was stirred at room temperature for 1 h. The resulting mixture was cooled to 0° C., and aqueous 1 N NaOH (100 ml) was then added portion wise. Et₂O (250 ml), and water (200 ml) were then added, and the yellow organic layer was further washed with water (150 ml), dried over anhydrous MgSO₄, filtered, and concentrated to dryness under reduced pressure.

The crude material was purified by FC (DCM/heptane=1/1 to give 4.1 g of 2-difluoromethoxy-1-fluoro-4-nitro-benzene.

Step 2 to Step 6

The synthesis was performed as described in example 81 replacing 2-difluoromethyl-1-fluoro-4-nitro-benzene with 2-difluoromethoxy-1-fluoro 4-nitro-benzene. MS[M+H]⁺= 324.4; m.p. 159° C.

Example 101: 1-(3-Difluoromethoxy-4-fluoro-phenyl)-4-[2-(2-hydroxy-ethyl)-imidazol-1-ylmethyl]-1H-[1,2,3]triazole

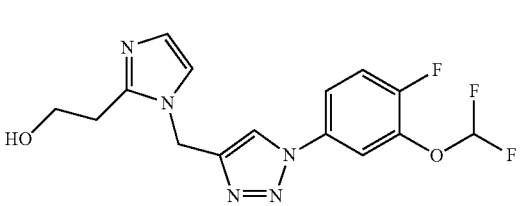 [SMILES: OCCc1nccn1Cc1cn(-c2ccc(F)c(OC(F)F)c2)nn1]

The synthesis was performed as described in example 100 replacing 2-methyl-1H-imidazole with 2-(1H-imidazol-2-yl)-ethanol (step 6). MS[M+H]⁺=354.4; m.p. 118° C.

Example 102: 1)-(3-Difluoromethyl-5-fluoro-phenyl)-4-(2-methyl-imidazol-1-ylmethyl)-1H [1,2,3]triazole

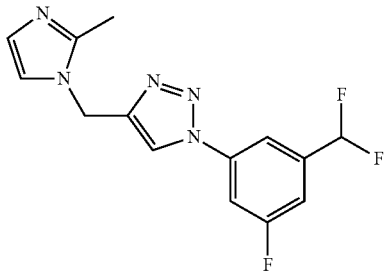 [SMILES: Cc1nccn1Cc1cn(-c2cc(F)cc(C(F)F)c2)nn1]

The synthesis was performed as described in example 81 replacing 2-fluoro-5-nitrobenzaldehyde with 3-fluoro-5-nitrobenzaldehyde (step 1). MS[M+H]$^+$=308.3: m.p. 141° C.

Example 103: 1-(3-Difluoromethyl-5-fluoro-phenyl)-4-[2-(2-hydroxy-ethyl)-imidazol-1-ylmethyl]-1H-[1,2,3]triazole

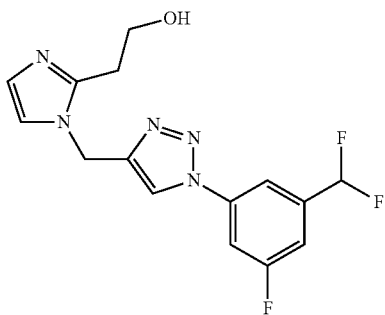 [SMILES: OCCc1nccn1Cc1cn(-c2cc(F)cc(C(F)F)c2)nn1]

The synthesis was performed as described in example 102 replacing 2-methyl-1H-imidazole with 2-(1H-imidazol-2-yl)-ethanol (step 6). MS[M++H]$^+$=338.3; melting range: 126-132° C.

Example 104: 1-(3-Difluoromethyl-5-fluoro-phenyl)-4-[2-(2-fluoro-ethyl)-imidazol-1-ylmethyl]-1H-[1,2,3]triazole

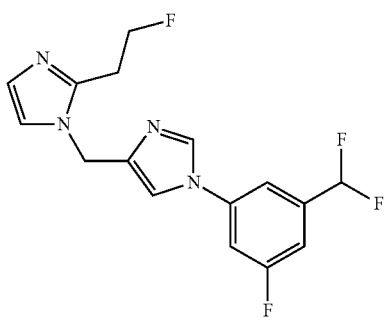 [SMILES: FCCc1nccn1Cc1cn(-c2cc(F)cc(C(F)F)c2)cn1]

A solution of 2-[1-[[1-[3-(difluoromethyl)-5-fluoro-phenyl]triazol-4-yl]methyl]imidazol-2-yl]ethanol (example 103; 3.4 g, 10 mmol) in DCM (50 mL) was added DAST (2 g, 12 mmol) and stirred at RT for 18 h under nitrogen atmosphere.

The reaction mass was quenched in ice-water and extracted with DCM. The organic layer was dried and concentrated to dryness under reduced pressure. The crude product was purified by flash chromatography. MS[M+H]$^+$=339.3; melting range: 111-112° C.

Example 105: 1-[3-(1, 1-Difluoro-ethyl)-4-fluoro-phenyl]-4-(2-methyl-imidazol-1-ylmethyl)-1H-[1,2,3]triazole

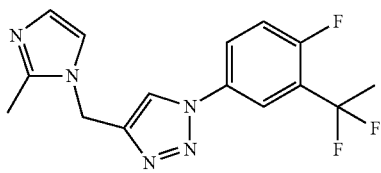 [SMILES: Cc1nccn1Cc1cn(-c2ccc(F)c(C(C)(F)F)c2)nn1]

The compound was prepared as described in example 81 replacing 2-fluoro-5-nitrobenzaldehyde with 2-fluoro-5-nitroacetophenone (step 1). MS[M+H]=$^+$322.3; m.p.: 149° C.

Example 106: 1-[3-(1,1-Difluoro-ethyl)-4-fluoro-phenyl]-4-[2-(2-hydroxy-ethyl)-imidazol-1-ylmethyl]-1H-[1,2,3]triazole

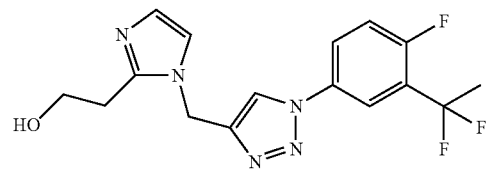 [SMILES: CC(F)(F)c1cc(-n2cc(Cn3ccnc3CCO)nn2)ccc1F]

The compound was prepared as described in example 81 replacing 2-fluoro-5-nitrobenzaldehyde with 2-fluoro-5-nitroacetophenone (step 1) and 2-methyl-imidazole with 2-(1H-imidazol-2-yl)-ethanol (step 6). MS[M+H]$^+$=352.3; m.p.: 113° C.

Example 107: 4-(2-Methyl imidazol-1-ylmethyl)-1-(4-pentafluoro-sulfane-phenyl)-1H-[1,2,3]triazole The compound was prepared as described in example 1 replacing 4-chloroaniline with 4-aminophenyl sulfur pentafluoride (step 1) and 3,5-dimethyl-1H-[1,2,4]triazole with 2-methyl-1H-imidazole (step 4). MS[M+H]$^+$=366.3; melting range: 166-167° C.

Example 108: 4-(2-hydroxy-ethyl-imidazol-1-yl methyl)-1-(4-pentafluoro-sulfane-phenyl)-1H-[1,2,3]triazole The compound was prepared as described in example 1 replacing 4-chloroaniline with 4-aminophenyl sulfur pentafluoride (step 1) and 3, 5-dimethyl-1H-[1,2,4]triazole with 2-(1H-imidazol-2-yl)-ethanol (step 4). MS[M+H]$^+$=396.3; melting range: 116-118° C.

Example 109: 1-(3-Chloro-4-fluoro-phenyl)-4-(2-methyl-2H-pyrazol-3-ylmethyl)-1H-[1,2,3]triazole

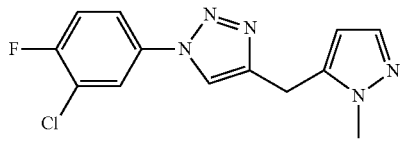 [SMILES: Cn1nccc1Cc1cn(-c2ccc(F)c(Cl)c2)nn1]

Step 1 to 3: 1-(3-Chloro-4-fluoro-phenyl)-4-chloromethyl-1H-[1,2,3]triazole

The compound was prepared as described in example 1 replacing 4-chloroaniline with 3-chloro-4-fluoroaniline (step 1).

Step 4: 1-(3-Chloro-4-fluoro-phenyl)-4-(2-methyl-2H-pyrazol-3-ylmethyl)-1-[1,2,3]triazole A mixture of 2 mmol of 1-(3-chloro-4-fluoro-phenyl)-4-chloromethyl-1H-[1,2,3]triazole (step 3), 4 mmol of 1-methyl-1H-pyrazole-5-boronic acid pinacol ester, 0.5 mmol of tetrabutyl ammonium bromide, 50 mg of tetrakis(triphenylphosphine)palladium(0), 5 mmol of sodium carbonate, 50 ml of toluene and 0.5 ml of water were refluxed under nitrogen for 3 hours.

After cooling to room temperature the solvent was concentrated to dryness under reduced pressure. The crude product was purified by flash chromatography. MS[M+H]$^+$=292.7; melting range: 85-89° C.

Example 110: 1-(4-Chloro-3-difluoromethoxy-phenyl)-4-(2-amino-imidazol-1-ylmethyl)-1H-[1,2,3]triazole hydrochloride

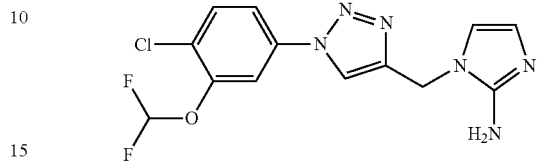

Example 110 was prepared as described in example 93 (table 6) replacing 2-methyl-1H-imidazole with 2-amino-1H-imidazole (step 4, reaction time 5 days). The crude free basic product was purified by flash chromatography (methylene chloride; 0 to 20% methanol).

The hydrochloride was prepared from the purified base with ethanolic hydrochloric acid. MS[M+H]$^+$=378.2; melting range: 214-220° C.

The examples in Table 7, specifically examples 111, 113A, 113B, and 114, were prepared as described in example 110 replacing 4-chloro-3-difluoromethoxy-aniline with the appropriate aniline derivative (step 1). Example 112 may be prepared as described in example 110 by replacing 4-chloro-3-difluoromethoxy-aniline with the appropriate aniline derivative (step 1).

TABLE 7

4-(2-amino-imidazol-1-ylmethyl)-1-phenyl-1H-[1,2,3]triazole derivatives.

| Ex. | R$^1$ | R$^2$ | Name-Structure | [M + H]$^+$ | m.p. [° C.] |
|---|---|---|---|---|---|
| 111 | 3-F | 5-CHF$_2$ | 4-(2-amino-imidazol-1-ylmethyl)-1-(3-fluoro-5-difluoromethyl-phenyl)-1H-[1,2,3]triazole | 309.3 | 166-168 |
| 112 | 3-F | 4-CHF$_2$ | 4-(2-amino-imidazol-1-ylmethyl)-1-(3-fluoro-4-difluoromethyl-phenyl)-1H-[1,2,3]triazole hydrochloride | 309.3 | 194-195 |

TABLE 7-continued 4-(2-amino-imidazol-1-ylmethyl)-1-phenyl-1H-[1,2,3]triazole derivatives.

| Ex. | R¹ | R² | Name-Structure | [M + H]⁺ | m.p. [° C.] |
|---|---|---|---|---|---|
| 113A | 4-Cl | 3-CHF₂ | 4-(2-amino-imidazol-1-ylmethyl)-1-(4-chloro-3-difluoromethyl-phenyl)-1H-[1,2,3]triazole hydrochloride | 325.7 | 235-238 |
| 113B | 4-F | 3-CHF₂ | 4-(2-amino-imidazol-1-ylmethyl)-1-(4-fluoro-3-difluoromethyl-phenyl)-1H-[1,2,3]triazole hydrochloride | 309.3 | 194-195 |
| 114 | 4-F | 3-CF₂CH₃ | 4-(2-amino-imidazol-1-ylmethyl)-1-[4-fluoro-3-(1,1-difluoroethyl)-phenyl]-1H-[1,2,3]triazole hydrochloride | 323.2 | 161-164 |

Example 115: 1-(3-difluoromethyl-4-fluoro-phenyl)-4-(1H-pyrazol-3-ylmethyl)-1H-[1,2,3]triazole

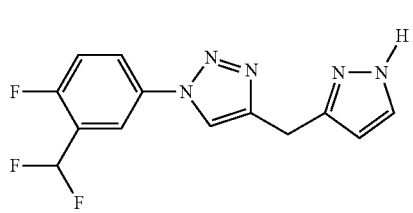 [SMILES: Fc1ccc(-n2cc(Cc3cc[nH]n3)nn2)cc1C(F)F]

The compound was prepared as described in example 109 replacing 4-chloroaniline with 3-difluoro-4-fluoro-aniline in step 1 and 1-methyl-1H-pyrazole-5-boronic acid pinacol ester with 1-THP protected 1H-pyrazole-3-boronic acid pinacol ester in step 4. MS[M+H]⁺=294.2; melting range: 102-105° C.

Example 116: [1-[[1-(4-chlorophenyl)triazol-4-yl]methyl]imidazol-2-yl]-(p-tolyl)methanone

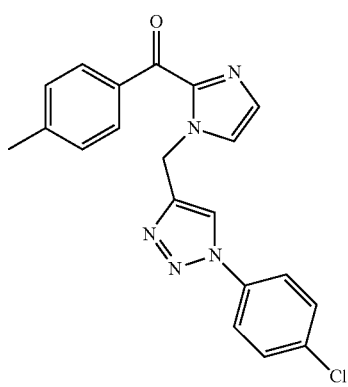 [SMILES: Cc1ccc(C(=O)c2nccn2Cc2cn(-c3ccc(Cl)cc3)nn2)cc1]

Example 116 was prepared as described in example 1 replacing 3,5-dimethyl-1H-[1,2,4]triazole with (1H-imidazol-2-yl)(p-tolyl)methanone (step 4).

Example 117: 1-[[1-(3,4-dichlorophenyl)triazol-4-yl]methyl]-2-methyl-benzimidazole

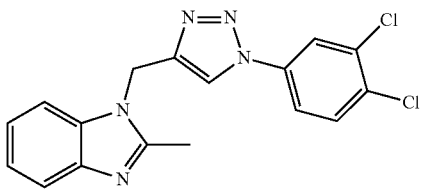 [SMILES: Cc1nc2ccccc2n1Cc1cn(-c2ccc(Cl)c(Cl)c2)nn1]

Example 117 was prepared as described in example 1 replacing 4-chloroaniline with 3,4-dichloroaniline (step 1) and 3,5-dimethyl-1H-[1,2,4]triazole with 2-methylbenzimidazole (step 4).

Example 118: 2-(1-((1-(4-(pentafluoro-l6-sulfanyl)phenyl)-1H-1,2,3-triazol-4-yl)methyl)-1H-imidazol-2-yl)ethan-1-ol

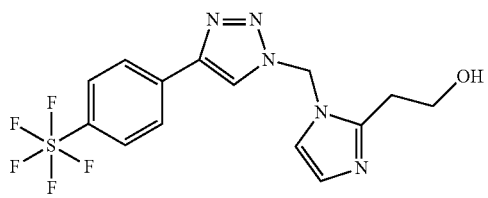 [SMILES: OCCc1nccn1Cn1cc(-c2ccc(S(F)(F)(F)(F)F)cc2)nn1]

Example 118 was prepared was prepared as described in example 1 replacing 4-chloroaniline with 4-pentafluorosulfonylaniline (step 1) and 3,5-dimethyl-1H-[1,2,4]triazole with 2-(1H-imidazol-2-yl)ethanol (step 4).

Biological Assays

Inhibition of Specific Binding to the Rat NR1/NR2B Receptor

Male Wistar rats (180 to 200 g) were killed by suffocation in a $CO_2$ chamber for two minutes. Whole brains without cerebellum were removed and dissected on ice, placed into closed vials and stored at −70° C.

Membrane fractions were prepared and tested using standard techniques. At the time of the assay, 1 g of the brains was placed into 25 ml of 50 mM Tris/10 mM EDTA buffer, pH 7.1, (25 vol. per g of original tissue) and homogenized for 30 sec at 20000 rpm with an Ultraturrax T25 (Jahnke & Kunkel, IKA-Labortechnik, Staufen, Germany). The homogenate was centrifuged at 4° C. for 10 min at 48000 g (OPTIMA L-70, Beckman, Palo Alto, Calif. 94304, USA).

The supernatant was discarded and the pellet was homogenized on ice for 30 sec at 20000 rpm with an Ultraturrax and again centrifuged at 48000 g for 30 minutes at 4° C. The resulted pellet was resuspended in 25 ml of 50 mM Tris/10 mM EDTA buffer, homogenized for 30 sec with an Ultraturrax, aliquoted, frozen at −70° C. and stored until use.

After thawing on the day of the assay, a 5 ml membrane aliquot was centrifuged at 48000 g for 30 min at 4° C. The pellet was resuspended in 5 ml of 5 mM Tris/1 mM EDTA buffer, pH 7.4, homogenized for 30 sec at 20000 rpm with an Ultraturrax and centrifuged at 48000 g for 30 min at 4° C. This was repeated twice. The final pellet was homogenized in 5 ml of 5 mM Tris/1 mM EDTA buffer at 4° C. with an Ultraturrax and used for the Ifenprodil-binding assay as described in the following.

The incubation mixture of 200 µl contained 5 nmol/l [$^3$H]-Ifenprodil, an optimised amount of membrane preparation, 5 mM Tris/1 mM EDTA (pH 7.4, 100 µM R(+)-3-PPP, 1 µM GBR-12909, 1 µM GBR-12935) and test compound in 1% DMSO. Nonspecific binding was estimated in the presence of 10M CP101.606. The samples were incubated for 60 min. at 4° C.

The incubation was terminated by filtration of the membrane preparations using Filtermat B (Pharmacia, Uppsala Sweden) and a Micro Cell Harvester (Skatron, Lier, Norway). The Filtermat B had been presoaked with 1% polyethylene imine and carefully washed with 50 mM Tris/HCl-buffer pH 7.7 after the filtration to separate free and bound radioactivity. The filters were counted in a scintillation counter (Betaplate 1205, Berthold, Wildbad, Germany) in order to determine the specific binding of [$^3$H]-Ifenprodil.

The optimal amount of membrane preparation in the assay had been determined and optimized for each membrane preparation separately before the test.

Test compounds were either screened at 6 to 10 increasing concentrations for the determination of $IC_{50}$ and Ki or at 2-4 concentrations for the determination of the percent inhibition. For pipetting of the incubation mixture we routinely used the robot Biomek2000 (Fa. Beckman).

For determination of $IC_{50}$ values the Hill-plot, 2-parameter-model was used. In the NR1/NR2B binding assay a dissociation constant ($K_D$) of [$^3$H]-Ifenprodil of 9 nM was determined.

NR2B Inhibition, $IC_{50}$ Values

| | NR2B binding assay | | |
|---|---|---|---|
| Example | IC50 [nM] | % INH @ 1 µM | % INH @ 10 µM |
| 1 | NT | 12.4 | 31.5 |
| 2 | NT | 23.9 | 43 |
| 3 | NT | 18.3 | 4.5 |
| 4 | NT | 21.6 | 2.0 |
| 5 | NT | 1.2 | 30.1 |
| 6 | NT | 11.8 | 21.6 |
| 7 | NT | 2.3 | 40.9 |
| 8 | 14300 | 8.3 | 38.7 |
| 9 | NT | 6.6 | 17.9 |
| 10 | NT | −6.0 | 3.5 |
| 11 | NT | 8.7 | 41.5 |
| 12 | NT | −0.66 | 11.0 |
| 13 | NT | 7.5 | 16.2 |
| 14 | 12500 | NT | 49.6 |
| 15 | NT | 6.4 | 22.2 |
| 16 | NT | 3.6 | 32.6 |
| 17 | NT | 19.9 | 12.5 |
| 18 | 46.6 | NT | NT |
| 19 | NT | 8.2 | 14.5 |
| 20 | NT | 27 | 15.3 |
| 21 | NT | −1.6 | 6.8 |
| 22 | NT | 14.5 | −2.2 |
| 23 | 77.4 | NT | NT |
| 24 | 38.4 | NT | NT |
| 25 | 25.8 | NT | NT |
| 26 | 9930 | 28.7 | 51.4 |
| 27 | 38.9 | NT | NT |
| 28 | 573 | NT | NT |
| 29 | 95.8 | NT | NT |
| 30 | 7200 | 12.7 | 53.2 |
| 31 | NT | 3.7 | 2.2 |

-continued

| | NR2B binding assay | | |
|---|---|---|---|
| Example | IC50 [nM] | % INH @ 1 μM | % INH @ 10 μM |
| 32 | 4.92 | NT | NT |
| 33 | 4.65 | NT | NT |
| 34 | 7.67 | NT | NT |
| 35 | 7.40 | NT | NT |
| 36 | 17.9 | NT | NT |
| 37 | 6.84 | NT | NT |
| 38 | 526 | NT | NT |
| 39 | 7.58 | NT | NT |
| 40 | 17.2 | NT | NT |
| 41 | 26.2 | NT | NT |
| 42 | 5.02 | NT | NT |
| 43 | 9.84 | NT | NT |
| 44 | 28.3 | NT | NT |
| 45 | 7.68 | NT | NT |
| 46 | NT | 9.3 | 7.4 |
| 47 | NT | 33.8 | −8.4 |
| 48 | NT | 29.6 | −17.1 |
| 49 | 778 | NT | NT |
| 50 | 21.2 | NT | NT |
| 51 | 7.01 | NT | NT |
| 52 | 1180 | NT | NT |
| 53 | 26.5 | NT | NT |
| 54 | 5.32 | NT | NT |
| 55 | 1.64 | NT | NT |
| 56 | 11.9 | NT | NT |
| 57 | 7.21 | NT | NT |
| 58 | 17.4 | NT | NT |
| 59 | 46.0 | NT | NT |
| 60 | 1620 | NT | NT |
| 61 | 31.7 | NT | NT |
| 62 | 3320 | NT | NT |
| 63 | 87.1 | NT | NT |
| 64 | 15.1 | NT | NT |
| 65 | 12.4 | NT | NT |
| 66 | 38.0 | NT | NT |
| 67 | 34.5 | NT | NT |
| 68 | 91.6 | NT | NT |
| 69 | 173 | NT | NT |
| 70 | 1.84 | NT | NT |
| 71 | 4.47 | NT | NT |
| 72 | 11.4 | NT | NT |
| 73 | 32.7 | NT | NT |
| 74 | 6.90 | NT | NT |
| 75 | 13.5 | NT | NT |
| 76 | 15.9 | NT | NT |
| 77 | 615 | NT | NT |
| 78 | 41.1 | NT | NT |
| 79 | 1400 | NT | NT |
| 80 | 2680 | NT | NT |
| 81 | 3.83 | NT | NT |
| 82 | 16.2 | NT | NT |
| 83 | 4.11 | NT | NT |
| 84 | 11.0 | NT | NT |
| 85 | 3.40 | NT | NT |
| 86 | 4.29 | NT | NT |
| 87 | 131 | NT | NT |
| 88 | 14.5 | NT | NT |
| 89 | 3.37 | NT | NT |
| 90 | 15.4 | NT | NT |
| 91 | 2.43 | NT | NT |
| 92 | 5.24 | NT | NT |
| 93 | 1.20 | NT | NT |
| 94 | 3.91 | NT | NT |
| 95 | 72.9 | NT | NT |
| 96 | 1.60 | NT | NT |
| 97 | 3.12 | NT | NT |
| 98 | 2.26 | NT | NT |
| 99 | 6.02 | NT | NT |
| 100 | 1.90 | NT | NT |
| 101 | 4.26 | NT | NT |
| 102 | 25.9 | NT | NT |
| 103 | 136 | NT | NT |
| 104 | 186 | NT | NT |
| 105 | 4.05 | NT | NT |
| 106 | 8.08 | NT | NT |
| 109 | 4320 | NT | NT |
| 110 | 0.52 | NT | NT |
| 111 | 2.13 | NT | NT |
| 113A | 0.65 | NT | NT |
| 113B | 0.48 | NT | NT |
| 114 | 0.51 | NT | NT |
| 115 | 236 | NT | NT |
| 116 | NT | −4.9 | NT |
| 117 | 141 | NT | NT |
| 118 | 263 | NT | NT |

HNR2BC: Effects of Test Articles on Cloned Human NR1/NR2B Ion Channels Expressed in Mammalian Cells The ability of test compounds to act as an antagonist of NR1/NR2B were evaluated with a calcium influx assay (Calcium 5 Assay Kit, Molecular Devices).

For the antagonist assessment, NR1/NR2B was activated with the positive control agonist ($Mg^{2+}$-free HBPS+100 μM glutamic acid+100 μM glycine). The effect of each test article to inhibit the signal was examined after agonist stimulation and compared to the positive control antagonist (MK-801). The signal elicited in the presence of the positive agonist ($Mg^{2+}$-free HBPS+100 μM glutamic acid+100 μM glycine) was set to 100 (0% inhibition) and the signal from the positive antagonist ($Mg^{2+}$-free HBPS+100 μM glutamic acid+100 μM glycine+100 μM MK-801) was set to 0 (100% inhibition).

Cell Culture:

A HEK cell line, stable transfected with hNR1/NR2B was used. This tetracycline inducible cell line is transfected with GRIN1 (GeneBank accession number NM 007327.2) and GRIN2B (GeneBank accession number NM_000834.3.). The cells were cultured in cell culture flasks with DMEM/F12 supplemented with 10% FCS, 1% PenStrep and a selection of additional antibiotics.

Forty-Eight (48) hours before the assay the cells were plated into 96-well black well, flat clear bottom microtiter plates at a density of 50000 cells/well. Twenty-Four (24) hours later the receptor expression was induced by the addition of 1 μg/ml tetracycline in the presence of 2 mM ketamine and 200 μM 7-CKA. After 24 h of receptor induction the plates were used for the assay.

Assay:

The medium was removed and the cells were loaded with 200 μl loading buffer (Molecular Devices) in Mg2+-free HBPS containing 100 μM 7-CKA at 37° C. for one (1) hour.

The test compounds were then solubilized in 100% DMSO and diluted to yield eight (8) different concentrations in 100% DMSO. A 96 well drug plate was prepared by diluting with water and glycine/glutamate to a 5-fold of final test concentration. Fluorescence intensity of the cells in the plate was measured in a FlexStation using an excitation wavelength of 485 nm and an emission wavelength of 525 nm. Twenty (20) seconds after starting the recordings the compounds together with the agonists glycine (100 μM) and glutamate (100 μM) were added into the wells and the fluorescence measured for ninety (90) seconds in summary.

The IC50 values provided in the paragraph below were determined using a 3 parameter plot.

| Example | IC50 [µM] |
|---|---|
| 23 | 17.5 |
| 42 | 3.17 |
| 81 | 3.79 |
| 82 | 4.89 |
| 84 | 4.2 |
| 93 | 0.41 |
| 97 | 0.58 |
| 101 | 1.65 |
| 109 | 109 |
| 110 | 0.077 |
| 111 | 3.42 |
| 113A | 0.84 |
| 113B | 0.66 |
| 114 | 2.34 |
| 115 | 10.5 |
| 116 | 22.35 |

Inhibition of Specific Binding to the hERG-Receptor (HERGBD)

A HEK cell line with stable transfected human ERG receptor was used for the assay. The cells were grown adherently and maintained in DULBECCOS' MEM medium with 10% FBS, 1% non-essential amino acids, 1% Penicillin/Streptomycin and 400 µg/ml G418 (Calbiochem).

Cells were split 2-3 times weekly between 1:3 and 1:4. For binding assays and membrane preparations the cell culture medium was removed, cells were washed with PBS. Crude membranes for radioligand binding experiments were prepared by scraping the cells off the dishes in ice cold 20 mM HEPES/0.1 mM KCl/pH 7.2. The cell suspension was homogenized on ice (Ultra turrax, 3×20 sec.) and the homogenate was spun for 10 min (1° C., 1000 g, OPTIMA, SW28, 2800 U/min). The supernatant was than centrifuged for 40 min at 100000 g (1° C., OPTIMA, SW28, 23000 U/min). The membrane pellet was resuspended in 20 mM HEPES/0.1 mM KCl/pH 7.2, frozen and stored at −80° C.

After thawing on the day of the assay, the membrane suspension was diluted further with 20 mM HEPES/0.1 mM KCl/pH 7.2.

The incubation mixture of 200 µl contained 1.5 nmol/l 3H-Dofetilide, optimized amount of membrane preparation, 20 mM HEPES/0.1 mM KCl/(pH 7.2) and inhibitor in 1% DMSO. Nonspecific binding was estimated in the presence of 10 M Dofetilide. The samples were incubated for 90 min. at RT.

Binding was terminated by filtration of the incubated membrane preparations using Filtermat B (Pharmacia, Uppsala Sweden) and a Micro Cell Harvester (Skatron, Lier, Norway). The Filtermat B had been presoaked with 1% polyethylenimine and carefully washed with 0.05 M Tris/HCl-buffer pH=7.7 after the filtration to separate free and bound radioactivity. The filters were counted in a scintillation counter (Betaplate 1205, Berthold, Wildbad, Germany) in order to determine the specific binding of [$^3$H]-Dofetilide.

The optimal amount of membrane preparation in the assay was determined and optimized for each membrane preparation separately in front of using the membranes in compound testing.

Test compounds were either screened at 6 to 10 increasing concentrations for the determination of IC50 and Ki or at 2-4 concentrations for the determination of the percent inhibition. For pipetting of the incubation mixture we routinely use the robot Biomek2000 (Fa. Beckman).

The IC50 values in the table below were determined using the Hill-plot, 2-parameter-model.

| Example | IC50 [µM] |
|---|---|
| 1 | 419 |
| 2 | 0.032 |
| 3 | 0.305 |
| 5 | 194 |
| 6 | 54.9 |
| 7 | >100 |
| 8 | 48.9 |
| 9 | 46.9 |
| 10 | 0.0039 |
| 11 | >100 |
| 12 | 11.8 |
| 13 | 45.1 |
| 14 | 30.5 |
| 15 | 87.9 |
| 16 | >100 |
| 17 | 25.6 |
| 18 | 2.23 |
| 19 | 33.8 |
| 20 | 35.6 |
| 21 | 3.52 |
| 23 | 7.94 |
| 24 | 5.64 |
| 25 | 2.68 |
| 26 | 12.1 |
| 27 | 0.57 |
| 28 | 11.2 |
| 29 | 2.53 |
| 30 | 3.58 |
| 31 | 22.35 |
| 32 | 3.93 |
| 33 | 2.23 |
| 34 | 1.12 |
| 35 | 5.88 |
| 36 | 1.16 |
| 37 | 0.585 |
| 38 | 5.68 |
| 39 | 1.74 |
| 40 | 14.7 |
| 41 | 13.7 |
| 42 | 2.99 |
| 43 | 2.72 |
| 44 | 3.57 |
| 45 | 0.539 |
| 46 | 7.58 |
| 49 | 4.53 |
| 50 | 3.39 |
| 51 | 4.97 |
| 52 | 41.7 |
| 53 | 6.41 |
| 54 | 6.21 |
| 55 | 4.71 |
| 56 | 6.46 |
| 57 | 8.59 |
| 58 | 15 |
| 59 | 6.27 |
| 60 | 6.63 |
| 61 | 3.62 |
| 62 | 45.9 |
| 63 | 11.2 |
| 64 | 7.82 |
| 65 | 3.87 |
| 66 | 3.54 |
| 67 | 2.55 |
| 68 | 5.12 |
| 69 | 4.41 |
| 70 | 3.92 |
| 71 | 10 |
| 72 | 4.6 |
| 73 | 13 |
| 74 | 33.8 |
| 75 | 32.8 |
| 76 | 10.3 |
| 77 | 150 |
| 78 | 26 |
| 79 | >100 |
| 80 | >100 |
| 81 | 14.3 |
| 82 | 15.7 |
| 83 | 16.7 |

-continued

| Example | IC50 [µM] |
|---|---|
| 84 | 25.1 |
| 85 | 6.46 |
| 86 | 3.24 |
| 87 | 7.52 |
| 88 | 93.4 |
| 89 | 8.52 |
| 90 | 5.35 |
| 91 | 7.19 |
| 92 | 11.3 |
| 93 | 9.6 |
| 94 | 3.02 |
| 95 | 5.84 |
| 96 | 4.41 |
| 97 | 11 |
| 98 | 17.1 |
| 99 | 23.8 |
| 100 | 12.8 |
| 101 | 36.7 |
| 102 | 16.8 |
| 103 | 26 |
| 104 | 30.6 |
| 105 | 73.1 |
| 109 | >100 |
| 110 | 3.6 |
| 111 | 3.29 |
| 113A | 3.09 |
| 113B | 11.04 |
| 114 | 4.31 |
| 115 | >100 |
| 117 | 3.09 |
| 118 | 12.3 |

RRNR2BB—Inhibition of Specific Binding to the Rat NR1/NR2B Receptor

Male Wistar rats (180 to 200 g) were killed by suffocation in a $CO_2$ chamber for two minutes. Whole brains without cerebellum were removed and dissected on ice, placed into closed vials and stored at −70° C.

Membrane fractions were prepared and tested using standard techniques. At the time of the assay, 1 g of the brains were placed into 25 ml of 50 mM Tris/10 mM EDTA buffer, pH=7.1, (25 vol. per g of original tissue) and was homogenized for 30 sec at 20000 U/min with an Ultraturrax T25 (Jahnke & Kunkel, IKA-Labortechnik, Staufen, Germany). The homogenate was centrifuged at 4° C. for 10 min at 48000 g (OPTIMA L-70, Beckman, Palo Alto, Calif. 94304, USA). The supernatant was discarded and the pellet was homogenized on ice for 30 sec at 20000 U/min with an Ultraturrax and again centrifuged at 48000 g for 30 minutes at 4° C. The resultant pellet was resuspended in 25 ml of 50 mM Tris/10 mM EDTA buffer, homogenized for 30 sec with an Ultraturrax, aliquoted, frozen at −70° C. and stored until use After thawing on the day of the assay, a 5 ml membrane aliquote was centrifuged at 48000 g for 30 min at 4° C. The pellet was resuspended in 5 ml of 5 mM Tris/1 mM EDTA buffer, pH=7.4, homogenized for 30 sec at 20000 U/min with an Ultraturrax and centrifuged at 48000 g for 30 min at 4° C. This step was repeated twice. The final pellet was homogenized in 5 ml of 5 mM Tris/mM EDTA buffer at 4° C. with an Ultraturrax and used for the Ifenprodil-binding assay.

The incubation mixture of 200 µl contained 5 nmol/l [$^3$H]-Ifenprodil, optimised amount of membrane preparation, 5 mM Tris/1 mM EDTA (pH 7.4, 100 µM R(+)-3-PPP, 1 µM GBR-12909, 1 µM GBR-12935) and inhibitor in 1% DMSO. Nonspecific binding was estimated in the presence of 10 M CP101.606. The samples were incubated for 60 min. at 4° C.

Binding was terminated by filtration of the incubated membrane preparations using Filtermat B (Pharmacia, Uppsala Sweden) and a Micro Cell Harvester (Skatron, Lier, Norway). The Filtermat B had been presoaked with 1% polyethylenimine and carefully washed with 50 nM Tris/HCl-buffer pH=7.7 after the filtration to separate free and bound radioactivity. The filters were counted in a scintillation counter (Betaplate 1205, Berthold, Wildbad, Germany) in order to determine the specific binding of [$^3$H]-Ifenprodil.

The optimal amount of membrane preparation in the assay has been determined and optimised for each membrane preparation separately in front of using the membranes in compound testing.

Test compounds were either screened at 6 to 10 increasing concentrations for the determination of IC50 and Ki or at 2-4 concentrations for the determination of the percent inhibition. For pipetting of the incubation mixture the robot Biomek2000 (Fa. Beckman) was used.

The IC50 values in the tables below were determined using the Hill-plot, 2-parameter-model. In the NR1/NR2B binding assay a dissociation constant (KD) of [$^3$H]-Ifenprodil was determined to be 9 nM. The specific binding in this assay was about 80%.

Reference compounds and their IC50 values tested in the hERG receptor binding assay are provided below.

| Example | IC50 [nM] |
|---|---|
| 1 | >10000 |
| 2 | >1000 |
| 3 | >10000 |
| 4 | >10000 |
| 5 | >10000 |
| 6 | >10000 |
| 7 | >10000 |
| 8 | 14300 |
| 9 | >10000 |
| 10 | >10000 |
| 11 | >1000 |
| 12 | >10000 |
| 13 | >10000 |
| 14 | 12500 |
| 15 | >10000 |
| 16 | >10000 |
| 17 | >10000 |
| 18 | 46.6 |
| 19 | >10000 |
| 20 | >10000 |
| 21 | >10000 |
| 22 | >10000 |
| 23 | 77.4 |
| 24 | 38.4 |
| 25 | 25.8 |
| 26 | 9930 |
| 27 | 38.9 |
| 28 | 573 |
| 29 | 95.8 |
| 30 | 7200 |
| 31 | >10000 |
| 32 | 4.92 |
| 33 | 4.65 |
| 34 | 7.67 |
| 35 | 7.4 |
| 36 | 17.9 |
| 37 | 6.84 |
| 38 | 526 |
| 39 | 7.58 |
| 40 | 17.2 |
| 41 | 26.2 |
| 42 | 5.02 |
| 43 | 9.84 |
| 44 | 28.3 |
| 45 | 7.68 |
| 46 | >10000 |

-continued

| Example | IC50 [nM] |
|---|---|
| 47 | >10000 |
| 48 | >10000 |
| 49 | 778 |
| 50 | 21.2 |
| 51 | 7.01 |
| 52 | 1180 |
| 53 | 26.5 |
| 54 | 5.32 |
| 55 | 1.64 |
| 56 | 11.9 |
| 57 | 7.21 |
| 58 | 17.4 |
| 59 | 46 |
| 60 | 1620 |
| 61 | 31.7 |
| 62 | 3320 |
| 63 | 87.1 |
| 64 | 15.1 |
| 65 | 12.4 |
| 66 | 38 |
| 67 | 34.5 |
| 68 | 91.6 |
| 69 | 173 |
| 70 | 1.84 |
| 71 | 4.47 |
| 72 | 11.4 |
| 73 | 32.7 |
| 74 | 6.9 |
| 75 | 13.5 |
| 76 | 15.9 |
| 77 | 615 |
| 78 | 41.1 |
| 79 | 1400 |
| 80 | 2680 |
| 81 | 3.83 |
| 82 | 16.2 |
| 83 | 4.11 |
| 84 | 11 |
| 85 | 3.4 |
| 86 | 4.29 |
| 87 | 131 |
| 88 | 14.5 |
| 89 | 3.37 |
| 90 | 15.4 |
| 91 | 2.43 |
| 92 | 5.24 |
| 93 | 1.2 |
| 94 | 3.91 |
| 95 | 72.9 |
| 96 | 1.6 |
| 97 | 3.12 |
| 98 | 2.26 |
| 99 | 6.02 |
| 100 | 1.9 |
| 101 | 4.26 |
| 102 | 25.9 |
| 103 | 136 |
| 104 | 186 |
| 105 | 4.05 |
| 106 | 8.08 |
| 109 | 4320 |
| 110 | 0.52 |
| 111 | 2.13 |
| 113A | 0.65 |
| 113B | 0.48 |
| 114 | 0.51 |
| 115 | 236 |
| 116 | >5000 |
| 117 | 141 |
| 118 | 263 |

Forced Swim Test in Mice

The compounds of the invention show significant antidepressive effects in the forced swim test in mice, an animal model of depression at doses of 100 mg/kg or below.

The method, which detects antidepressant activity, follows that described by Porsolt et al (*Arch. Int. Pharmacodyn.*, 229, 327-336, 1977), which is incorporated by reference herein in its entirety.

Mice forced to swim in a situation from which they cannot escape rapidly become immobile. Antidepressants decrease the duration of immobility.

Male NMRI mice (Janvier, France), weighing 20-30 g, were individually placed in a cylinder (height=24 cm; diameter=13 cm) containing 10 cm water (22° C.) from which they cannot escape.

The mice were placed in the water for 6 minutes and the duration of immobility during the last 4 minutes was measured. The latency to the first bout of immobility was also recorded starting from the beginning of the test. 10 mice were studied per group. The test substance was administered p.o. 30 minutes before the test and compared with vehicle control group. The test was performed blind. The results are shown in the table below.

| Example | Minimum effective dose (mg/kg p.o.) |
|---|---|
| 82 | 60 |
| 101 | >30 |

All patents, patent applications, publications and presentations referred to herein are incorporated by reference in their entirety.

Any combination of the groups described above for the various variables is contemplated herein. Throughout the specification, groups and substituents thereof are chosen by one skilled in the field to provide stable moieties and compounds.

While the foregoing specification teaches the principles of the present invention, and specific embodiments of the invention have been described for the purposes of illustration, and examples have been provided for the purposes of illustration, it will be understood that various modifications may be made without deviating from the spirit and scope of the invention as come within the scope of the following claims and their equivalents.

The invention claimed is:

1. A compound of Formula (I):

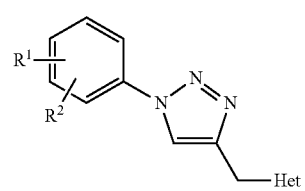

(I)

or a pharmaceutically acceptable salt, solvate, or N-oxide thereof; wherein:

Het is a heterocyclic ring selected from:

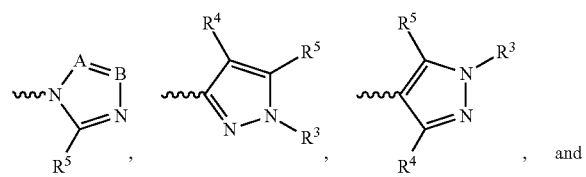

, , , and

-continued

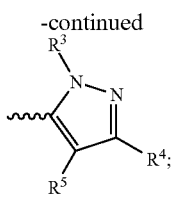

wherein
- A and B are each independently selected from N or C—R$^4$, provided that at least one of A and B is C—R$^4$;
- Each R$^1$ and R$^2$ are independently selected from hydrogen; halogen; C$_{1-6}$ alkyl, straight or branched, optionally substituted with at least one substituent selected from hydroxy, halogen, C$_{1-3}$ (halo)alkoxy and C$_{3-6}$ (halo)cycloalkyl; C$_{3-6}$ cycloalkyl, optionally substituted with at least one substituent selected from hydroxy, halogen, C$_{1-3}$ (halo)alkyl and C$_{1-3}$ (halo)alkoxy; C$_{1-3}$ alkoxy, optionally substituted with at least one substituent selected from hydroxy, halogen, C$_{1-3}$ (halo)alkoxy and C$_{3-6}$ (halo)cycloalkyl; —O—C$_{3-6}$ cycloalkyl, optionally substituted with at least one substituent selected from hydroxy, halogen, C$_{1-3}$ (halo)alkyl and C$_{1-3}$ (halo)alkoxy; —S—C$_{1-3}$ alkyl, optionally substituted with at least one halogen atom; —SO$_2$—C$_{1-3}$ alkyl, optionally substituted with at least one halogen atom; and —SF$_5$; or
- R$^1$ and R$^2$ together form a 5 to 7 member carbocycle, optionally substituted with at least one substituent selected from hydroxy, halogen, C$_{1-3}$ (halo)alkyl and C$_{1-3}$ (halo)alkoxy; or a 5 to 7 member heterocycle containing one to three heteroatoms selected from O, S or N, optionally substituted with at least one substituent selected from hydroxy, halogen, C$_{1-3}$ (halo)alkyl and C$_{1-3}$ (halo)alkoxy;
- R$^3$ is selected from hydrogen; C$_{1-5}$ alkyl, optionally substituted with at least one substituent, selected from halogen, hydroxy, C$_{1-3}$ (halo)alkoxy, and C$_{3-6}$ (halo)cycloalkyl; C$_{3-6}$ cycloalkyl, optionally substituted with at least one substituent, selected from hydroxy, halogen, C$_{1-3}$ (halo)alkyl, and C$_{1-3}$ (halo)alkoxy; —O—C$_{3-6}$ cycloalkyl, optionally substituted with at least one substituent, selected from hydroxy, halogen, C$_{1-3}$ (halo)alkyl, and C$_{1-3}$ (halo)alkoxy; and
- each R$^4$ and, R$^5$ group is independently selected from hydrogen; amino; halogen; C$_{1-5}$ alkyl, optionally substituted with at least one substituent selected from halogen, hydroxy, C$_{1-3}$ (halo)alkoxy, and C$_{3-6}$ (halo)cycloalkyl; C$_{1-5}$ alkoxy, optionally substituted with at least one substituent selected from hydroxy, halogen, C$_{1-3}$ (halo)alkoxy and C$_{3-6}$ (halo)cycloalkyl; C$_{3-6}$ cycloalkyl, optionally substituted with at least one substituent selected from hydroxy, halogen, C$_{1-3}$ (halo)alkyl and C$_{1-3}$ (halo)alkoxy; and —O—C$_{3-6}$ cycloalkyl optionally substituted with at least one substituent selected from hydroxy, halogen, C$_{1-3}$ (halo)alkyl and C$_{1-3}$ (halo)alkoxy.

2. The compound of claim 1, wherein at least one of R$^1$ and R$^2$ are not hydrogen.

3. The compound of claim 2, wherein R$^1$ and R$^2$ are not hydrogen.

4. The compound of claim 3, wherein any R$^1$ and R$^2$ are at a meta-position or a para-position of the phenyl ring.

5. The compound of claim 1, wherein at least one of R$^1$ and R$^2$ is F, Cl, Br, C$_{1-4}$ (halo)alkyl, C$_{3-6}$ (halo)cycloalkyl, C$_{1-3}$ (halo)alkoxy, C$_{1-3}$ (halo)alkoxy-C$_{1-3}$ (halo)alkyl, C$_{3-6}$ (halo)cycloalkyl-C$_{1-3}$ (halo)alkyl, or C$_{3-6}$ (halo)cycloalkyl-C$_{1-3}$ (halo)alkoxy.

6. The compound of claim 2, wherein at least one of R$^1$ and R$^2$ is F, Cl, Br, C$_{1-4}$ (halo)alkyl, C$_{3-6}$ (halo)cycloalkyl, C$_{1-3}$ (halo)alkoxy, C$_{1-3}$ (halo)alkoxy-C$_{1-3}$ (halo)alkyl, C$_{3-6}$ (halo)cycloalkyl-C$_{1-3}$ (halo)alkyl, or C$_{3-6}$ (halo)cycloalkyl-C$_{1-3}$ (halo)alkoxy.

7. The compound of claim 1, wherein Het is:

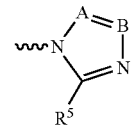

wherein A is N or C—R$^4$; B is C—R$^4$, and each R$^4$ and R$^5$ group is independently selected from hydrogen; amino; F; Cl; C$_{1-3}$ alkyl, optionally substituted with at least one group selected from halogen, hydroxy, and C$_{1-3}$ (halo)alkoxy; C$_{1-3}$ (halo)alkoxy; C$_{3-6}$ (halo)cycloalkyl; and C$_{3-6}$ (halo)cycloalkyl-C$_{1-3}$ (halo)alkyl.

8. The compound of claim 3, wherein Het is:

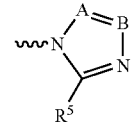

wherein A is N or C—R$^4$; B is C—R$^4$, and each R$^4$ and R$^5$ group is independently selected from hydrogen; amino; F; C$_{1-3}$ alkyl, optionally substituted with at least one group selected from halogen, hydroxy, and C$_{1-3}$ (halo)alkoxy; C$_{1-3}$ (halo)alkoxy; C$_{3-6}$ (halo)cycloalkyl; and C$_{3-6}$ (halo)cycloalkyl-C$_{1-3}$ (halo)alkyl.

9. The compound of claim 1, wherein Het is selected from:

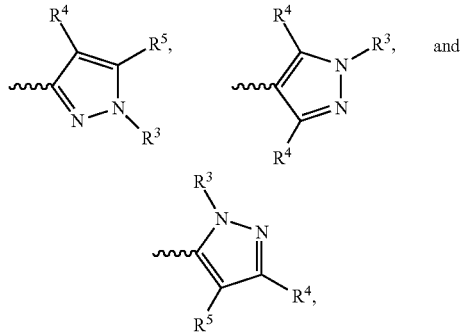

wherein
- Each R$^3$ is independently selected from hydrogen; C$_{1-3}$ alkyl, optionally substituted with at least one substituent selected from halogen, hydroxy, and/or C$_{1-3}$ (halo)alkoxy; C$_{3-6}$ (halo)cycloalkyl; and C$_{3-6}$ (halo)cycloalkyl-C$_{1-3}$ (halo)alkyl; and
- Each R$^4$ and R$^5$ group is independently selected from hydrogen; amino; F; Cl; C$_{1-3}$ alkyl, optionally substituted with at least one substituent, selected from halogen, hydroxy, and C$_{1-3}$ (halo)alkoxy; C$_{1-3}$ (halo)alkoxy; C$_{3-6}$ (halo)cycloalkyl; and C$_{3-6}$ (halo)cycloalkyl-C$_{1-3}$ (halo)alkyl.

10. The compound of claim 3, wherein Het is selected from:

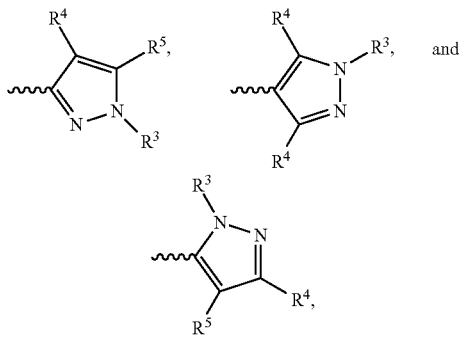

and wherein
Each $R^3$ is independently selected from hydrogen; $C_{1-3}$ alkyl, optionally substituted with at least one substituent selected from halogen, hydroxy, and $C_{1-3}$ (halo)alkoxy; $C_{3-6}$ (halo)cycloalkyl; and $C_{3-6}$ (halo)cycloalkyl-$C_{1-3}$ (halo)alkyl; and
Each $R^4$ and $R^5$ group is independently selected from hydrogen; amino; a halogen selected from F and Cl; $C_{1-3}$ alkyl, optionally substituted with at least one substituent, selected from halogen, hydroxy, and $C_{1-3}$ (halo)alkoxy; $C_{1-3}$ (halo)alkoxy; $C_{3-6}$ (halo)cycloalkyl; and $C_{3-6}$ (halo)cycloalkyl-$C_{1-3}$ (halo)alkyl.

11. The Compound of claim 1 selected from the group consisting of:
1-(4-Chloro-phenyl)-4-(3, 5-dimethyl-[1,2,4]triazol-1-ylmethyl)-1H-[1,2,3]triazole;
1-(4-Chloro-phenyl)-4-(5-propyl-[1,2,4]triazol-1-ylmethyl)-1H-[1,2,3]triazole;
1-(4-Chloro-phenyl)-4-(3-propyl-[1,2,4]triazol-1-ylmethyl)-1H-[1,2,3]triazole;
1-(4-Chloro-phenyl)-4-(3-isopropyl-[1,2,4]triazol-1-ylmethyl)-1H-[1,2,3]triazole;
1-(4-Chloro-phenyl)-4-(5-ethyl-[1,2,4]triazol-1-ylmethyl)-1H-[1,2,3]triazole;
1-(4-Chloro-phenyl)-4-(3-ethyl-[1,2,4]triazol-1-ylmethyl)-1H-[1,2,3]triazole;
1-(4-Chloro-phenyl)-4-(5-isopropyl-[1,2,4]triazol-1-ylmethyl)-1H-[1,2,3]triazole;
1-(4-Chloro-phenyl)-4-(5-methyl-[1,2,4]triazol-1-ylmethyl)-1H-[1,2,3]triazole;
1-(4-Chloro-phenyl)-4-(3-methyl-[1,2,4]triazol-1-ylmethyl)-1H-[1,2,3]triazole;
1-(4-Chloro-phenyl)-4-(3, 5-dicyclopropyl-[1,2,4]triazol-1-ylmethyl)-1H-[1,2,3]triazole;
1-(4-Chloro-phenyl)-4-(5-cyclobutyl-[1,2,4]triazol-1-ylmethyl)-1H-[1,2,3]triazole;
1-(4-Chloro-phenyl)-4-(3-cyclobutyl-[1,2,4]triazol-1-ylmethyl)-1H-[1,2,3]triazole;
1-(4-Chloro-phenyl)-4-(3-cyclopropyl-[1,2,4]triazol-1-ylmethyl)-1H-[1,2,3]triazole;
1-(4-Chloro-phenyl)-4-(5-cyclopentyl-[1,2,4]triazol-1-ylmethyl)-1H-[1,2,3]triazole;
1-(4-Chloro-phenyl)-4-(3-cyclopentyl-[1,2,4]triazol-1-ylmethyl)-1H-[1,2,3]triazole;
1-(4-Chloro-phenyl)-4-(5-cyclopropyl-[1,2,4]triazol-1-ylmethyl)-1H-[1,2,3]triazole;
1-(4-Chloro-phenyl)-4-(3-trifluoromethyl-[1,2,4]triazol-1-ylmethyl)-1H-[1,2,3]triazole;
1-(4-Chloro-phenyl)-4-(2-propyl-imidazol-1-ylmethyl)-1H-[1,2,3]triazole;
4-(5-tert-Butyl-[1,2,4]triazol-1-ylmethyl)-1-(4-chloro-phenyl)-1H-[1,2,3]triazole;
4-(3-tert-Butyl-[1,2,4]triazol-1-ylmethyl)-1-(4-chloro-phenyl)-1H-[1,2,3]triazole;
1-(4-Chloro-phenyl)-4-(5-cyclobutyl-3-methyl-[1,2,4]triazol-1-ylmethyl)-1H-[1,2,3]triazole;
1-(4-Chloro-phenyl)-4-(3-cyclobutyl-5-methyl-[1,2,4]triazol-1-ylmethyl)-1H-[1,2,3]triazole;
1-(4-Chloro-phenyl)-4-(2-isopropyl-imidazol-1-ylmethyl)-1H-[1,2,3]triazole;
1-(4-Chloro-phenyl)-4-(2-methyl-imidazol-1-ylmethyl)-1H-[1,2,3]triazole;
1-(4-Chloro-phenyl)-4-(2-ethyl-imidazol-1-ylmethyl)-1H-[1,2,3]triazole;
4-(2-Chloro-imidazol-1-ylmethyl)-1-(4-chloro-phenyl)-1H-[1,2,3]triazole;
4-(2-Butyl-imidazol-1-ylmethyl)-1-(4-chloro-phenyl)-1H-[1,2,3]triazole;
4-(2-Hydroxymethyl-imidazol-1-ylmethyl)-1-(4-chloro-phenyl)-1H-[1,2,3]triazole;
1-(4-Chloro-phenyl)-4-(2-cyclopropyl-imidazol-1-ylmethyl)-1H-[1,2,3]triazole;
4-(2-tert-Butyl-imidazol-1-ylmethyl)-1-(4-chloro-phenyl)-1H-[1,2,3]triazole;
1-(4-Chloro-phenyl)-4-(3-methyl-[1,2,4]triazol-4-ylmethyl)-1H-[1,2,3]triazole;
1-(3,4-Dichloro-phenyl)-4-(2-methyl-imidazol-1-ylmethyl)-1H-[1,2,3]triazole;
1-(3,4-Dichloro-phenyl)-4-(2-ethyl-imidazol-1-ylmethyl)-1H-[1,2,3]triazole;
1-(3,4-Dichloro-phenyl)-4-(2-propyl-imidazol-1-ylmethyl)-1H-[1,2,3]triazole;
1-(3,4-Dichloro-phenyl)-4-(2-isopropyl-imidazol-1-ylmethyl)-1H-[1,2,3]triazole;
4-(2-Cyclopropyl-imidazol-1-ylmethyl)-1-(3,4-dichloro-phenyl)-1H-[1,2,3]triazole;
4-(2-Butyl-imidazol-1-ylmethyl)-1-(3,4-dichloro-phenyl)-1H-[1,2,3]triazole;
4-(2-tert-Butyl-imidazol-1-ylmethyl)-1-(3,4-dichloro-phenyl)-1H-[1,2,3]triazole;
4-(2-Cyclobutyl-imidazol-1-ylmethyl)-1-(3,4-dichloro-phenyl)-1H-[1,2,3]triazole;
4-[2-(2-Hydroxyethyl)-imidazol-1-ylmethyl]-1-(3,4-dichloro-phenyl)-1H-[1,2,3]triazole;
1-(3,4-Dichloro-phenyl)-4-[2-(2-fluoro-ethyl)-imidazol-1-ylmethyl]-1H-[1,2,3]triazole;
1-(3-Chloro-4-fluoro-phenyl)-4-(2-ethyl-imidazol-1-ylmethyl)-1H-[1,2,3]triazole;
1-(3-Chloro-4-fluoro-phenyl)-4-(2-propyl-imidazol-1-ylmethyl)-1H-[1,2,3]triazole;
1-(3-Chloro-4-fluoro-phenyl)-4-(2-cyclopropyl-imidazol-1-ylmethyl)-1H-[1,2,3]triazole;
4-(2-Butyl-imidazol-1-ylmethyl)-1-(3-chloro-4-fluoro-phenyl)-1H-[1,2,3]triazole;
4-(3,5-Dimethyl-[1,2,4]triazol-1-ylmethyl)-1-phenyl-1H-[1,2,3]triazole;
4-(5-Hydroxymethyl-3-methyl-[1,2,4]triazol-1-ylmethyl)-1-phenyl-1H-[1,2,3]triazole;
4-(3-Hydroxymethyl-5-methyl-[1,2,4]triazol-1-ylmethyl)-1-phenyl-1H-[1,2,3]triazole;
1-(2,4-Dichloro-phenyl)-4-(2-methyl-imidazol-1-ylmethyl)-1H-[1,2,3]triazole;
1-(4-Chloro-3-fluoro-phenyl)-4-(2-methyl-imidazol-1-ylmethyl)-1H-[1,2,3]triazole;

1-(3-Chloro-4-fluoro-phenyl)-4-(2-methyl-imidazol-1-yl-methyl)-1H-[1,2,3]triazole;
1-(4-Fluoro-2-methoxy-phenyl)-4-(2-methyl-imidazol-1-ylmethyl)-1H-[1,2,3]triazole;
1-(3-Fluoro-4-methyl-phenyl)-4-(2-methyl-imidazol-1-ylmethyl)-1H-[1,2,3]triazole;
1-(4-Fluoro-3-methyl-phenyl)-4-(2-methyl-imidazol-1-ylmethyl)-1H-[1,2,3]triazole;
1-(4-Chloro-3-methyl-phenyl)-4-(2-methyl-imidazol-1-ylmethyl)-1H-[1,2,3]triazole;
1-(4-Chloro-3-trifluoromethyl-phenyl)-4-(2-methyl-imidazol-1-ylmethyl)-1H-[1,2,3]triazole;
4-(2-Methyl-imidazol-1-ylmethyl)-1-(3-trifluoromethoxy-phenyl)-1H-[1,2,3]triazole;
4-(2-Methyl-imidazol-1-ylmethyl)-1-(3-trifluoromethyl-phenyl)-1H-[1,2,3]triazole;
4-(2-Methyl-imidazol-1-ylmethyl)-1-(4-trifluoromethyl-phenyl)-1H-[1,2,3]triazole;
4-(2-Cyclopropyl-imidazol-1-ylmethyl)-1-(2,4-dichloro-phenyl)-1H-[1,2,3]triazole;
1-(4-Chloro-3-fluoro-phenyl)-4-(2-cyclopropyl-imidazol-1-ylmethyl)-1H-[1,2,3]triazole;
4-(2-Cyclopropyl-imidazol-1-ylmethyl)-1-(4-fluoro-2-methoxy-phenyl)-1H-[1,2,3]triazole;
4-(2-Cyclopropyl-imidazol-1-ylmethyl)-1-(3-fluoro-4-methyl-phenyl)-1H-[1,2,3]triazole;
4-(2-Cyclopropyl-imidazol-1-ylmethyl)-1-(4-fluoro-3-methyl-phenyl)-1H-[1,2,3]triazole;
1-(4-Chloro-3-methyl-phenyl)-4-(2-cyclopropyl-imidazol-1-ylmethyl)-1H-[1,2,3]triazole;
1-(4-Chloro-3-trifluoromethyl-phenyl)-4-(2-cyclopropyl-imidazol-1-ylmethyl)-1H-[1,2,3]triazole;
4-(2-Cyclopropyl-imidazol-1-ylmethyl)-1-(3-trifluoromethoxy-phenyl)-1H-[1,2,3]triazole;
4-(2-Cyclopropyl-imidazol-1-ylmethyl)-1-(3-trifluoromethyl-phenyl)-1H-[1,2,3]triazole;
4-(2-Cyclopropyl-imidazol-1-ylmethyl)-1-(4-trifluoromethyl-phenyl)-1H-[1,2,3]triazole;
1-(4-Chloro-3-methyl-phenyl)-4-(2-ethyl-imidazol-1-ylmethyl)-1H-[1,2,3]triazole;
1-(4-Chloro-3-methyl-phenyl)-4-(2-isopropyl-imidazol-1-ylmethyl)-1H-[1,2,3]triazole;
4-(2-Ethyl-imidazol-1-ylmethyl)-1-(3-trifluoromethoxy-phenyl)-1H-[1,2,3]triazole;
4-(2-Isopropyl-imidazol-1-ylmethyl)-1-(3-trifluoromethoxy-phenyl)-1H-[1,2,3]triazole;
1-(4-Chloro-3-methyl-phenyl)-4-[2-(2-hydroxy-ethyl)-imidazol-1-ylmethyl]-1H-[1,2,3]triazole;
1-(4-Chloro-3-methyl-phenyl)-4-[2-(2-fluoro-ethyl)-imidazol-1-ylmethyl]-1H-[1,2,3]triazole;
1-(3-Cyclopropyl-phenyl)-4-(2-methyl-imidazol-1-ylmethyl)-1H-[1,2,3]triazole;
1-(3-Methanesulfonyl-phenyl)-4-(2-methyl-imidazol-1-ylmethyl)-1H-[1,2,3]triazole;
1-(3-Cyclopropyl-phenyl)-4-[2-(2-hydroxy-ethyl)-imidazol-1-ylmethyl]-1H-[1,2,3]triazole;
4-[2-(2-Hydroxy-ethyl)-imidazol-1-ylmethyl]-1-(3-methanesulfonyl-phenyl)-1H-[1,2,3]triazole;
4-[2-(2-Fluoro-ethyl)-imidazol-1-ylmethyl]-1-(3-methanesulfonyl-phenyl)-1H-[1,2,3]triazole;
1-(3-Difluoromethyl-4-fluoro-phenyl)-4-(2-methyl-imidazol-1-ylmethyl)-1H-[1,2,3]triazole;
4-(2-Cyclopropyl-imidazol-1-ylmethyl)-1-(3-difluoromethyl-4-fluoro-phenyl)-1H-[1,2,3]triazole;
1-(3-Difluoromethyl-4-fluoro-phenyl)-4-(2-ethyl-imidazol-1-ylmethyl)-1H-[1,2,3]triazole;
1-(3-Difluoromethyl-4-fluoro-phenyl)-4-(2-isopropyl-imidazol-1-ylmethyl)-1H-[1,2,3]triazole;
1-(3-Difluoromethyl-4-fluoro-phenyl)-4-(2-propyl-imidazol-1-ylmethyl)-1H-[1,2,3]triazole;
1-(3-Difluoromethyl-4-fluoro-phenyl)-4-(2-butyl-imidazol-1-ylmethyl)-1H-[1,2,3]triazole;
1-(3-Difluoromethyl-4-fluoro-phenyl)-4-(2-tert.butyl-imidazol-1-ylmethyl)-1H-[1,2,3]triazole;
1-(3-Difluoromethyl-4-fluoro-phenyl)-4-[2-(2-hydroxy-ethyl)-imidazol-1-ylmethyl]-1H-[1,2,3]triazole;
1-(4-Chloro-3-difluoromethyl-phenyl)-4-(2-methyl-imidazol-1-ylmethyl)-1H-[1,2,3]triazole;
1-(4-Chloro-3-difluoromethyl-phenyl)-4-(2-cyclopropyl-imidazol-1-ylmethyl)-1H-[1,2,3]triazole;
1-(4-Chloro-3-difluoromethyl-phenyl)-4-(2-ethyl-imidazol-1-ylmethyl)-1H-[1,2,3]triazole;
1-(4-Chloro-3-difluoromethyl-phenyl)-4-(2-isopropyl-imidazol-1-ylmethyl)-1H-[1,2,3]triazole;
1-(4-Chloro-3-difluoromethoxy-phenyl)-4-(2-methyl-imidazol-1-ylmethyl)-1H-[1,2,3]triazole;
1-(4-Chloro-3-difluoromethoxy-phenyl)-4-(2-cyclopropyl-imidazol-1-ylmethyl)-1H-[1,2,3]triazole;
4-(2-tert-Butyl-imidazol-1-ylmethyl)-1-(4-chloro-3-difluoromethoxy-phenyl)-1H-[1,2,3]triazole;
1-(4-Chloro-3-difluoromethoxy-phenyl)-4-(2-ethyl-imidazol-1-ylmethyl)-1H-[1,2,3]triazole;
1-(4-Chloro-3-difluoromethoxy-phenyl)-4-(2-isopropyl-imidazol-1-ylmethyl)-1H-[1,2,3]triazole;
1-(4-Chloro-3-difluoromethoxy-phenyl)-4-[2-(2-hydroxy-ethyl)-imidazol-1-ylmethyl]-1H-[1,2,3]triazole;
1-(4-Chloro-3-difluoromethoxy-phenyl)-4-[2-(2-fluoro-ethyl)-imidazol-1-ylmethyl]-1H-[1,2,3]triazole;
1-(3-Difluoromethoxy-4-fluoro-phenyl)-4-(2-methyl-imidazol-1-ylmethyl)-1H-[1,2,3]triazole;
1-(3-Difluoromethoxy-4-fluoro-phenyl)-4-[2-(2-hydroxy-ethyl)-imidazol-1-ylmethyl]-1H-[1,2,3]triazole;
1-(3-Difluoromethyl-5-fluoro-phenyl)-4-(2-methyl-imidazol-1-ylmethyl)-1H-[1,2,3]triazole;
1-(3-Difluoromethyl-5-fluoro-phenyl)-4-[2-(2-hydroxy-ethyl)-imidazol-1-ylmethyl]-1H-[1,2,3]triazole;
1-(3-Difluoromethyl-5-fluoro-phenyl)-4-[2-(2-fluoro-ethyl)-imidazol-1-ylmethyl]-1H-[1,2,3]triazole;
1-[3-(1,1-Difluoro-ethyl)-4-fluoro-phenyl]-4-(2-methyl-imidazol-1-ylmethyl)-1H-[1,2,3]triazole;
1-[3-(1,1-Difluoro-ethyl)-4-fluoro-phenyl]-4-[2-(2-hydroxy-ethyl)-imidazol-1-ylmethyl]-1H-[1,2,3]triazole;
4-(2-Methyl-imidazol-1-ylmethyl)-1-(4-pentafluoro-sulfane-phenyl)-1H-[1,2,3]triazole;
4-(2-hydroxy-ethyl-imidazol-1-ylmethyl)-1-(4-pentafluoro-sulfane-phenyl)-1H-[1,2,3]triazole;
1-(3-Chloro-4-fluoro-phenyl)-4-(2-methyl-2H-pyrazol-3-ylmethyl)-1H-[1,2,3]triazole; and
1-(4-Chloro-3-difluoromethoxy-phenyl)-4-(2-amino-imidazol-1-ylmethyl)-1H-[1,2,3]triazole; and
pharmaceutically acceptable salts, solvates, or N-oxides thereof.

12. The compound of claim 1 selected from the group consisting of:
4-(2-amino-imidazol-1-ylmethyl)-1-(3-fluoro-5-difluoromethyl-phenyl)-1H-[1,2,3]triazole;
4-(2-amino-imidazol-1-ylmethyl)-1-(3-fluoro-4-difluoromethyl-phenyl)-1H-[1,2,3]triazole;
4-(2-amino-imidazol-1-ylmethyl)-1-(4-chloro-3-difluoromethyl-phenyl)-1H-[1,2,3]triazole;
4-(2-amino-imidazol-1-ylmethyl)-1-[4-fluoro-3-(1,1-difluoroethyl)-phenyl]-1H-[1,2,3]triazole; and 1-(3-difluoromethyl-4-fluoro-phenyl)-4-(1H-pyrazol-3-ylmethyl)-1H-[1,2,3]triazole; and
pharmaceutically acceptable salts, solvates, or N-oxides thereof.

13. The compound of claim 1 selected from the group consisting of:
2-(1-((1-(4-(pentafluoro-l6-sulfanyl)phenyl)-1H-1,2,3-triazol-4-yl)methyl)-1H-imidazol-2-yl)ethan-1-ol; and
pharmaceutically acceptable salts, solvates, or N-oxides thereof.

14. A pharmaceutical composition comprising a therapeutically effective amount of a compound of claim 1 or a pharmaceutically acceptable salt, solvate, or N-oxide thereof, and at least one pharmaceutically acceptable excipient.

15. The pharmaceutical composition of claim 14, further comprising a second active ingredient.

16. A compound of Formula (I), having the structure of Formula (IA):

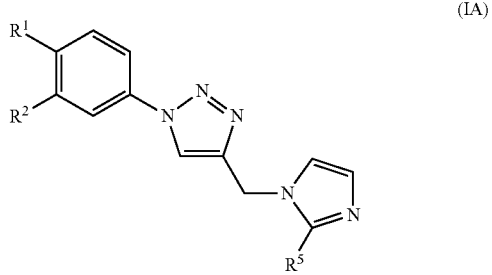

(IA)

wherein:
Each $R^1$ and $R^2$ are independently selected from halogen; $C_{1-6}$ alkyl, straight or branched, optionally substituted with at least one substituent selected from hydroxy, halogen, $C_{1-3}$ (halo)alkoxy and $C_{3-6}$ (halo)cycloalkyl; $C_{3-6}$ cycloalkyl, optionally substituted with at least one substituent selected from hydroxy, halogen, $C_{1-3}$ (halo)alkyl and $C_{1-3}$ (halo)alkoxy; $C_{1-3}$ alkoxy, optionally substituted with at least one substituent selected from hydroxy, halogen, $C_{1-3}$ (halo)alkoxy and $C_{3-6}$ (halo)cycloalkyl; —O—$C_{3-6}$ cycloalkyl, optionally substituted with at least one substituent selected from hydroxy, halogen, $C_{1-3}$ (halo)alkyl and $C_{1-3}$ (halo)alkoxy; —S—$C_{1-3}$ alkyl, optionally substituted with at least one halogen atom; —$SO_2$—$C_{1-3}$ alkyl, optionally substituted with at least one halogen atom; and —$SF_5$; or
$R^1$ and $R^2$ together form a 5 to 7 member carbocycle, optionally substituted with at least one substituent selected from hydroxy, halogen, $C_{1-3}$ (halo)alkyl and $C_{1-3}$ (halo)alkoxy; or a 5 to 7 member heterocycle containing one to three heteroatoms selected from O, S or N, optionally substituted with at least one substituent selected from hydroxy, halogen, $C_{1-3}$ (halo)alkyl and $C_{1-3}$ (halo)alkoxy; and
$R^5$ is independently selected from hydrogen; amino; halogen; $C_{1-5}$ alkyl, optionally substituted with at least one substituent selected from halogen, hydroxy, $C_{1-3}$ (halo)alkoxy, and $C_{3-6}$ (halo)cycloalkyl; $C_{1-5}$ alkoxy, optionally substituted with at least one substituent selected from hydroxy, halogen, $C_{1-3}$ (halo)alkoxy and $C_{3-6}$ (halo)cycloalkyl; $C_{3-6}$ cycloalkyl, optionally substituted with at least one substituent selected from hydroxy, halogen, $C_{1-3}$ (halo)alkyl and $C_{1-3}$ (halo)alkoxy; and —O—$C_{3-6}$ cycloalkyl optionally substituted with at least one substituent selected from hydroxy, halogen, $C_{1-3}$ (halo)alkyl and $C_{1-3}$ (halo)alkoxy;
and pharmaceutically acceptable salts thereof.

17. A compound selected from the group consisting of:
1-(3,4-Dichloro-phenyl)-4-(2-methyl-imidazol-1-ylmethyl)-1H-[1,2,3]triazolo;
1-(3,4-Dichloro-phenyl)-4-(2-ethyl-imidazol-1-ylmethyl)-1H-[1,2,3]triazolo;
1-(3,4-Dichloro-phenyl)-4-(2-propyl-imidazol-1-ylmethyl)-1H-[1,2,3]triazolo;
1-(3,4-Dichloro-phenyl)-4-(2-isopropyl-imidazol-1-ylmethyl)-1H-[1,2,3]triazole;
4-(2-Cyclopropyl-imidazol-1-ylmethyl)-1-(3,4-dichlorophenyl)-1H-[1,2,3]triazole;
4-(2-Butyl-imidazol-1-ylmethyl)-1-(3,4-dichloro-phenyl)-1H-[1,2,3]triazole;
4-(2-tert-Butyl-imidazol-1-ylmethyl)-1-(3,4-dichlorophenyl)-1H-[1,2,3]triazole;
4-(2-Cyclobutyl-imidazol-1-ylmethyl)-1-(3,4-dichlorophenyl)-1H-[1,2,3]triazole;
4-[2-(2-Hydroxyethyl)-imidazol-1-ylmethyl]-1-(3,4-dichloro-phenyl)-1H-[1,2,3]triazole;
1-(3,4-Dichloro-phenyl)-4-[2-(2-fluoro-ethyl)-imidazol-1-ylmethyl]-1H-[1,2,3]triazole;
1-(3-Chloro-4-fluoro-phenyl)-4-(2-ethyl-imidazol-1-ylmethyl)-1H-[1,2,3]triazole;
1-(3-Chloro-4-fluoro-phenyl)-4-(2-propyl-imidazol-1-ylmethyl)-1H-[1,2,3]triazole;
1-(3-Chloro-4-fluoro-phenyl)-4-(2-cyclopropyl-imidazol-1-ylmethyl)-1H-[1,2,3]triazole;
4-(2-Butyl-imidazol-1-ylmethyl)-1-(3-chloro-4-fluorophenyl)-1H-[1,2,3]triazole;
1-(4-Chloro-3-fluoro-phenyl)-4-(2-methyl-imidazol-1-ylmethyl)-1H-[1,2,3]triazole;
1-(3-Chloro-4-fluoro-phenyl)-4-(2-methyl-imidazol-1-ylmethyl)-1H-[1,2,3]triazole;
1-(3-Fluoro-4-methyl-phenyl)-4-(2-methyl-imidazol-1-ylmethyl)-1H-[1,2,3]triazole;
1-(4-Fluoro-3-methyl-phenyl)-4-(2-methyl-imidazol-1-ylmethyl)-1H-[1,2,3]triazole;
1-(4-Chloro-3-methyl-phenyl)-4-(2-methyl-imidazol-1-ylmethyl)-1H-[1,2,3]triazole;
1-(4-Chloro-3-trifluoromethyl-phenyl)-4-(2-methyl-imidazol-1-ylmethyl)-1H-[1,2,3]triazole;
1-(4-Chloro-3-fluoro-phenyl)-4-(2-cyclopropyl-imidazol-1-ylmethyl)-1H-[1,2,3]triazole;
4-(2-Cyclopropyl-imidazol-1-ylmethyl)-1-(3-fluoro-4-methyl-phenyl)-1H-[1,2,3]triazole;
4-(2-Cyclopropyl-imidazol-1-ylmethyl)-1-(4-fluoro-3-methyl-phenyl)-1H-[1,2,3]triazole;
1-(4-Chloro-3-methyl-phenyl)-4-(2-cyclopropyl-imidazol-1-ylmethyl)-1H-[1,2,3]triazole;
1-(4-Chloro-3-trifluoromethyl-phenyl)-4-(2-cyclopropyl-imidazol-1-ylmethyl)-1H-[1,2,3]triazole;
1-(4-Chloro-3-methyl-phenyl)-4-(2-ethyl-imidazol-1-ylmethyl)-1H-[1,2,3]triazole;
1-(4-Chloro-3-methyl-phenyl)-4-(2-isopropyl-imidazol-1-ylmethyl)-1H-[1,2,3]triazole;
1-(4-Chloro-3-methyl-phenyl)-4-[2-(2-hydroxy-ethyl)-imidazol-1-ylmethyl]-1H-[1,2,3]triazole;
1-(4-Chloro-3-methyl-phenyl)-4-[2-(2-fluoro-ethyl)-imidazol-1-ylmethyl]-1H-[1,2,3]triazole;
1-(3-Difluoromethyl-4-fluoro-phenyl)-4-(2-methyl-imidazol-1-ylmethyl)-1H-[1,2,3]triazole;

4-(2-Cyclopropyl-imidazol-1-ylmethyl)-1-(3-difluoromethyl-4-fluoro-phenyl)-1H-[1,2,3]triazole;
1-(3-Difluoromethyl-4-fluoro-phenyl)-4-(2-ethyl-imidazol-1-ylmethyl)-1H-[1,2,3]triazole;
1-(3-Difluoromethyl-4-fluoro-phenyl)-4-(2-isopropyl-imidazol-1-ylmethyl)-1H-[1,2,3]triazole;
1-(3-Difluoromethyl-4-fluoro-phenyl)-4-(2-propyl-imidazol-1-ylmethyl)-1H-[1,2,3]triazole;
1-(3-Difluoromethyl-4-fluoro-phenyl)-4-(2-butyl-imidazol-1-ylmethyl)-1H-[1,2,3]triazole;
1-(3-Difluoromethyl-4-fluoro-phenyl)-4-(2-tert.butyl-imidazol-1-ylmethyl)-1H-[1,2,3]triazole;
1-(3-Difluoromethyl-4-fluoro-phenyl)-4-[2-(2-hydroxy-ethyl)-imidazol-1-ylmethyl]-1H-[1,2,3]triazole;
1-(4-Chloro-3-difluoromethyl-phenyl)-4-(2-methyl-imidazol-1-ylmethyl)-1H-[1,2,3]triazole;
1-(4-Chloro-3-difluoromethyl-phenyl)-4-(2-cyclopropyl-imidazol-1-ylmethyl)-1H-[1,2,3]triazole;
1-(4-Chloro-3-difluoromethyl-phenyl)-4-(2-ethyl-imidazol-1-ylmethyl)-1H-[1,2,3]triazole;
1-(4-Chloro-3-difluoromethyl-phenyl)-4-(2-isopropyl-imidazol-1-ylmethyl)-1H-[1,2,3]triazole;
1-(4-Chloro-3-difluoromethoxy-phenyl)-4-(2-methyl-imidazol-1-ylmethyl)-1H-[1,2,3]triazole;
1-(4-Chloro-3-difluoromethoxy-phenyl)-4-(2-cyclopropyl-imidazol-1-ylmethyl)-1H-[1,2,3]triazole;
4-(2-tert-Butyl-imidazol-1-ylmethyl)-1-(4-chloro-3-difluoromethoxy-phenyl)-1H-[1,2,3]triazole;
1-(4-Chloro-3-difluoromethoxy-phenyl)-4-(2-ethyl-imidazol-1-ylmethyl)-1H-[1,2,3]triazole;
1-(4-Chloro-3-difluoromethoxy-phenyl)-4-(2-isopropyl-imidazol-1-ylmethyl)-1H-[1,2,3]triazole;
1-(4-Chloro-3-difluoromethoxy-phenyl)-4-[2-(2-hydroxy-ethyl)-imidazol-1-ylmethyl]-1H-[1,2,3]triazole;
1-(4-Chloro-3-difluoromethoxy-phenyl)-4-[2-(2-fluoro-ethyl)-imidazol-1-ylmethyl]-1H-[1,2,3]triazole;
1-(3-Difluoromethoxy-4-fluoro-phenyl)-4-(2-methyl-imidazol-1-ylmethyl)-1H-[1,2,3]triazole;
1-(3-Difluoromethoxy-4-fluoro-phenyl)-4-[2-(2-hydroxy-ethyl)-imidazol-1-ylmethyl]-1H-[1,2,3]triazole;
1-[3-(1,1-Difluoro-ethyl)-4-fluoro-phenyl]-4-(2-methyl-imidazol-1-ylmethyl)-1H-[1,2,3]triazole;
1-[3-(1,1-Difluoro-ethyl)-4-fluoro-phenyl]-4-[2-(2-hydroxy-ethyl)-imidazol-1-ylmethyl]-1H-[1,2,3]triazole;
1-(4-Chloro-3-difluoromethoxy-phenyl)-4-(2-amino-imidazol-1-ylmethyl)-1H-[1,2,3]triazole;
4-(2-Amino-imidazol-1-ylmethyl)-1-(4-chloro-3-difluoromethyl-phenyl)-1H-[1,2,3]triazole;
4-(2-Amino-imidazol-1-ylmethyl)-1-(4-fluoro-3-difluoromethyl-phenyl)-1H-[1,2,3]triazole; and
4-(2-amino-imidazol-1-ylmethyl)-1-[4-fluoro-3-(1,1-difluoroethyl)-phenyl]-1H-[1,2,3]triazole;
and pharmaceutically acceptable salts thereof.

18. A pharmaceutical composition comprising a therapeutically effective amount of a compound of claim 17 or a pharmaceutically acceptable salt, solvate, or N-oxide thereof, and at least one pharmaceutically acceptable excipient.

19. A compound selected from the group consisting of:
1-(4-Chloro-3-methyl-phenyl)-4-(2-methyl-imidazol-1-ylmethyl)-1H-[1,2,3]triazolo;
1-(4-Chloro-3-difluoromethoxy-phenyl)-4-(2-methyl-imidazol-1-ylmethyl)-1H-[1,2,3]triazole;
1-(4-Chloro-3-difluoromethoxy-phenyl)-4-(2-ethyl-imidazol-1-ylmethyl)-1H-[1,2,3]triazole;
1-(4-Chloro-3-difluoromethoxy-phenyl)-4-(2-isopropyl-imidazol-1-ylmethyl)-1H-[1,2,3]triazole;
1-(3-Difluoromethoxy-4-fluoro-phenyl)-4-(2-methyl-imidazol-1-ylmethyl)-1H-[1,2,3]triazole; and
1-(4-Chloro-3-difluoromethoxy-phenyl)-4-(2-amino-imidazol-1-ylmethyl)-1H-[1,2,3]triazole;
and pharmaceutically acceptable salts thereof.

20. A compound of claim 19, wherein the compound is 1-(4-Chloro-3-methyl-phenyl)-4-(2-methyl-imidazol-1-ylmethyl)-1H-[1,2,3]triazolo;
and pharmaceutically acceptable salts thereof.

21. A compound of claim 19, wherein the compound is 1-(4-Chloro-3-difluoromethoxy-phenyl)-4-(2-methyl-imidazol-1-ylmethyl)-1H-[1,2,3]triazole;
and pharmaceutically acceptable salts thereof.

22. A compound of claim 19, wherein the compound is 1-(4-Chloro-3-difluoromethoxy-phenyl)-4-(2-ethyl-imidazol-1-ylmethyl)-1H-[1,2,3]triazole;
and pharmaceutically acceptable salts thereof.

23. A compound of claim 19, wherein the compound is 1-(4-Chloro-3-difluoromethoxy-phenyl)-4-(2-isopropyl-imidazol-1-ylmethyl)-1H-[1,2,3]triazole;
and pharmaceutically acceptable salts thereof.

24. A compound of claim 19, wherein the compound is 1-(3-Difluoromethoxy-4-fluoro-phenyl)-4-(2-methyl-imidazol-1-ylmethyl)-1H-[1,2,3]triazole; and
and pharmaceutically acceptable salts thereof.

25. A compound of claim 19, wherein the compound is 1-(4-Chloro-3-difluoromethoxy-phenyl)-4-(2-amino-imidazol-1-ylmethyl)-1H-[1,2,3]triazole;
and pharmaceutically acceptable salts thereof.

26. A compound of Formula (I), having the structure of Formula (IB):

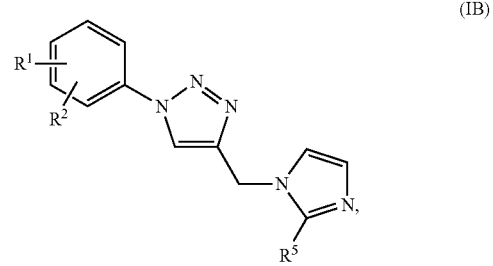

(IB)

wherein:
Each $R^1$ and $R^2$ are independently selected from hydrogen; halogen; $C_{1-6}$ alkyl, straight or branched, optionally substituted with at least one substituent selected from hydroxy, halogen, $C_{1-3}$ (halo)alkoxy and $C_{3-6}$ (halo)cycloalkyl; $C_{3-6}$ cycloalkyl, optionally substituted with at least one substituent selected from hydroxy, halogen, $C_{1-3}$ (halo)alkyl and $C_{1-3}$ (halo)alkoxy; $C_{1-3}$ alkoxy, optionally substituted with at least one substituent selected from hydroxy, halogen, $C_{1-3}$ (halo)alkoxy and $C_{3-6}$ (halo)cycloalkyl; —O—$C_{3-6}$ cycloalkyl, optionally substituted with at least one substituent selected from hydroxy, halogen, $C_{1-3}$ (halo)alkyl and $C_{1-3}$ (halo)alkoxy; —S—$C_{1-3}$ alkyl, optionally substituted with at least one halogen atom; —$SO_2$—$C_{1-3}$ alkyl, optionally substituted with at least one halogen atom; and —$SF_5$; or
$R^1$ and $R^2$ together form a 5 to 7 member carbocycle, optionally substituted with at least one substituent selected from hydroxy, halogen, $C_{1-3}$ (halo)alkyl and $C_{1-3}$ (halo)alkoxy; or a 5 to 7 member heterocycle containing one to three heteroatoms selected from O, S or N, optionally substituted with at least one substituent selected from hydroxy, halogen, $C_{1-3}$ (halo)alkyl and $C_{1-3}$ (halo)alkoxy; and $R^5$ is independently selected from hydrogen; amino; halogen; $C_{1-5}$ alkyl, optionally substituted with at least one substituent selected from halogen, hydroxy, $C_{1-3}$ (halo)alkoxy, and $C_{3-6}$ (halo)cycloalkyl; $C_{1-5}$ alkoxy, optionally substituted with at least one substituent selected from hydroxy, halogen, $C_{1-3}$ (halo)alkoxy and $C_{3-6}$ (halo)cycloalkyl; $C_{3-6}$ cycloalkyl, optionally substituted with at least one substituent selected from hydroxy, halogen, $C_{1-3}$ (halo)alkyl and $C_{1-3}$ (halo)alkoxy; and —O—$C_{3-6}$ cycloalkyl optionally substituted with at least one substituent selected from hydroxy, halogen, $C_{1-3}$ (halo)alkyl and $C_{1-3}$ (halo)alkoxy;

and pharmaceutically acceptable salts thereof.

27. A compound selected from the group consisting of:
1-(4-Chloro-phenyl)-4-(2-propyl-imidazol-1-ylmethyl)-1H-[1,2,3]triazole;
1-(4-Chloro-phenyl)-4-(2-isopropyl-imidazol-1-ylmethyl)-1H-[1,2,3]triazole;
1-(4-Chloro-phenyl)-4-(2-methyl-imidazol-1-ylmethyl)-1H-[1,2,3]triazole;
1-(4-Chloro-phenyl)-4-(2-ethyl-imidazol-1-ylmethyl)-1H-[1,2,3]triazole;
4-(2-Chloro-imidazol-1-ylmethyl)-1-(4-chloro-phenyl)-1H-[1,2,3]triazole;
4-(2-Butyl-imidazol-1-ylmethyl)-1-(4-chloro-phenyl)-1H-[1,2,3]triazole;
4-(2-Hydroxymethyl-imidazol-1-ylmethyl)-1-(4-chloro-phenyl)-1H-[1,2,3]triazole;
1-(4-Chloro-phenyl)-4-(2-cyclopropyl-imidazol-1-ylmethyl)-1H-[1,2,3]triazole;
4-(2-tert-Butyl-imidazol-1-ylmethyl)-1-(4-chloro-phenyl)-1H-[1,2,3]triazole;
1-(2,4-Dichloro-phenyl)-4-(2-methyl-imidazol-1-ylmethyl)-1H-[1,2,3]triazole;
1-(4-Fluoro-2-methoxy-phenyl)-4-(2-methyl-imidazol-1-ylmethyl)-1H-[1,2,3]triazole;
4-(2-Methyl-imidazol-1-ylmethyl)-1-(3-trifluoromethoxy-phenyl)-1H-[1,2,3]triazole;
4-(2-Methyl-imidazol-1-ylmethyl)-1-(3-trifluoromethyl-phenyl)-1H-[1,2,3]triazole;
4-(2-Methyl-imidazol-1-ylmethyl)-1-(4-trifluoromethyl-phenyl)-1H-[1,2,3]triazole;
4-(2-Cyclopropyl-imidazol-1-ylmethyl)-1-(2,4-dichloro-phenyl)-1H-[1,2,3]triazole;
4-(2-Cyclopropyl-imidazol-1-ylmethyl)-1-(4-fluoro-2-methoxy-phenyl)-1H-[1,2,3]triazole;
4-(2-Cyclopropyl-imidazol-1-ylmethyl)-1-(3-trifluoromethoxy-phenyl)-1H-[1,2,3]triazole;
4-(2-Cyclopropyl-imidazol-1-ylmethyl)-1-(3-trifluoromethyl-phenyl)-1H-[1,2,3]triazole;
4-(2-Cyclopropyl-imidazol-1-ylmethyl)-1-(4-trifluoromethyl-phenyl)-1H-[1,2,3]triazole;
4-(2-Ethyl-imidazol-1-ylmethyl)-1-(3-trifluoromethoxy-phenyl)-1H-[1,2,3]triazole;
4-(2-Isopropyl-imidazol-1-ylmethyl)-1-(3-trifluoromethoxy-phenyl)-1H-[1,2,3]triazole;
1-(3-Cyclopropyl-phenyl)-4-(2-methyl-imidazol-1-ylmethyl)-1H-[1,2,3]triazole;
1-(3-Methanesulfonyl-phenyl)-4-(2-methyl-imidazol-1-ylmethyl)-1H-[1,2,3]triazole;
1-(3-Cyclopropyl-phenyl)-4-[2-(2-hydroxy-ethyl)-imidazol-1-ylmethyl]-1H-[1,2,3]triazole;
4-[2-(2-Hydroxy-ethyl)-imidazol-1-ylmethyl]-1-(3-methanesulfonyl-phenyl)-1H-[1,2,3]triazole;
4-[2-(2-Fluoro-ethyl)-imidazol-1-ylmethyl]-1-(3-methanesulfonyl-phenyl)-1H-[1,2,3]triazole;
1-(3-Difluoromethyl-5-fluoro-phenyl)-4-(2-methyl-imidazol-1-ylmethyl)-1H-[1,2,3]triazole;
1-(3-Difluoromethyl-5-fluoro-phenyl)-4-[2-(2-hydroxy-ethyl)-imidazol-1-ylmethyl]-1H-[1,2,3]triazole;
1-(3-Difluoromethyl-5-fluoro-phenyl)-4-[2-(2-fluoro-ethyl)-imidazol-1-ylmethyl]-1H-[1,2,3]triazole;
4-(2-Methyl-imidazol-1-ylmethyl)-1-(4-pentafluoro-sulfane-phenyl)-1H-[1,2,3]triazole;
4-(2-Amino-imidazol-1-ylmethyl)-1-(3-fluoro-5-difluoromethyl-phenyl)-1H-[1,2,3]triazole
[1-[[1-(4-Chlorophenyl)triazol-4-yl]methyl]imidazol-2-yl]-(p-tolyl)methanone; and
2-(1-((1-(4-(Pentafluoro-l6-sulfanyl)phenyl)-1H-1,2,3-triazol-4-yl)methyl)-1H-imidazol-2-yl)ethan-1-ol;

and pharmaceutically acceptable salts thereof.

28. A compound selected from the group consisting of:
[1-[[1-(4-chlorophenyl)triazol-4-yl]methyl]imidazol-2-yl]-(p-tolyl)methanone; and
1-[[1-(3,4-dichlorophenyl)triazol-4-yl]methyl]-2-methyl-benzimidazole;

and pharmaceutically acceptable salt, solvate, or N-oxide thereof.

* * * * *